United States Patent
Plank et al.

(10) Patent No.: US 11,352,638 B2
(45) Date of Patent: Jun. 7, 2022

(54) MINIMAL UTR SEQUENCES

(71) Applicant: ethris GmbH, Planegg (DE)

(72) Inventors: Christian Plank, Wessling (DE);
Carsten Rudolph, Krailling (DE);
Manish Kumar Aneja, Munich (DE);
Ludwig Weiss, Kissing (DE)

(73) Assignee: ethris GmbH, Planegg (DE)

( * ) Notice: Subject to any disclaimer, the term of this patent is extended or adjusted under 35 U.S.C. 154(b) by 340 days.

(21) Appl. No.: 16/090,588

(22) PCT Filed: Mar. 30, 2017

(86) PCT No.: PCT/EP2017/057592
§ 371 (c)(1),
(2) Date: Oct. 1, 2018

(87) PCT Pub. No.: WO2017/167910
PCT Pub. Date: Oct. 5, 2017

(65) Prior Publication Data
US 2019/0144883 A1 May 16, 2019

(30) Foreign Application Priority Data

Mar. 31, 2016 (EP) .................................... 16163264
Jun. 30, 2016 (EP) .................................... 16177094

(51) Int. Cl.
*C12N 15/113* (2010.01)
*C12N 15/85* (2006.01)
*C12N 15/67* (2006.01)
*C12N 5/071* (2010.01)

(52) U.S. Cl.
CPC ........... *C12N 15/85* (2013.01); *C12N 5/0688* (2013.01); *C12N 15/113* (2013.01); *C12N 15/67* (2013.01); *C12N 2015/859* (2013.01); *C12N 2015/8572* (2013.01); *C12N 2800/107* (2013.01); *C12N 2800/22* (2013.01); *C12N 2830/34* (2013.01); *C12N 2840/105* (2013.01)

(58) Field of Classification Search
None
See application file for complete search history.

(56) References Cited

U.S. PATENT DOCUMENTS

2011/0244519 A1   10/2011   McGarrity et al.

FOREIGN PATENT DOCUMENTS

| CN | 104032031 A | 9/2014 |
| RU | 2321634 C2 | 4/2008 |
| WO | WO 2002/074961 A1 | 9/2002 |
| WO | WO 2005/095632 A2 | 10/2005 |
| WO | WO 2012/081271 A1 | 6/2012 |

OTHER PUBLICATIONS

Rees et al (Nature 347:685-9) (Year: 1990).*
STN Registry No. 133924-88-6 (Year: 1991).*
Gen Bank accession No. AZ301211 (Year: 2010).*
Gen Bank accession No. CG663293 (Year: 2010).*
Database Nucleotide NCBI; Aug. 21, 2008, Anonymous: "Taeniopygia guttata clone 0058P0019G12 putative mitochrondrial ATP synthase gamma chain mRNA, complete cds; nuclear gene for mitochrondrial product," XP002764154, Database accession No. DQ215956 sequence.
Database Nucleotide NCBI; Aug. 21, 2008, Anonymous: "Taeniopgyia guttata clone 0058P0019C09 putative mitochondrial ATP synthase gamma chain mRNA, complete cds; nuclear gene for mitochrondrial product," XP002764155, Database accession No. DQ215955 sequence.
Database Nucleotide NCBI; Apr. 21, 2015, Anonymous: "Foot-and-mouth disease virus—type O isolate PAK/44/2008, complete genome," XP002764156, Database accession No. GU384682 sequence.
Database Nucleotide NCIB; Apr. 21, 2015, Anonymous: "Foot-and-mouth disease virus—type O isolate PAK/45/2008, complete genome," XP002764157, Database accession No. GU384683 sequence.
Database Nucleotide NCBI; Apr. 23, 2015, Anonymous: "Foot-and-mouth disease virus—type SAT 2 isolate SAT2/SEN/7/83 P2/P3 polyportein gene, partial cds," XP002764158, Database accession No. KJ144916 sequence.
Database Nucleotide NCBI; Sep. 1, 2006, Anonmyous: "Mus musculus integrator complex subunit 1, mNRA (cDNA clone MGC: 67612 IMAGE: 6409930), complete cds," XP002764159, Database accession No. BC063266 sequence.
Database Nucleotide NCBI; Dec. 9, 2005, Anonymous: "*Homo sapiens* integrator complex subunit 1, mRNA (cDNA clone IMAGE:3618123), partial cds," XP002764160, Database accession No. BC004286 sequence.
Database GenBank Sep. 1, 2005, Anonymous: "JGI_XZT32793. fwd NIH_XGC_tropTad5 Xenopus tropicalis cDNA clone IMAGE: 7608881 5-, mRNA sequence," XP002764161, Database accession No. CX410129 sequence.
Database Nucleotide NCBI; Jan. 11, 2012, Anonymous: "Aedes albopictus cell-line C6/36 Dicer 2 (Dcr-2) mRNA, complete cds," XP002764162, Database accession No. JF819822 sequence.
Database Nucleotide NCBI; May 2, 2001, Anonymous: "Mus musculus TRH4 mRNA, complete cds," XP002764163, Database accession No. AY029533 sequence.

(Continued)

*Primary Examiner* — Christopher M Gross
(74) *Attorney, Agent, or Firm* — Morse, Barnes-Brown & Pendleton, P.C.; Lisa M. Warren, Esq.; Erin E. Bryan, Esq.

(57) ABSTRACT

Described are DNA molecules which can be transcribed into an mRNA harbouring novel UTR sequences combining the advantages of being extremely short and at the same time allowing for high translation efficiencies of RNA molecules containing them. Further, described are vectors comprising such a DNA molecule and to host cells comprising such a vector. Moreover, described are corresponding RNA molecules containing such UTRs. Further, described in a pharmaceutical composition comprising the described RNA molecule are optionally a pharmaceutically acceptable carrier as well as to the use of the described UTRs for translating a coding region of an RNA molecule into a polypeptide or a protein encoded by said coding region.

12 Claims, 20 Drawing Sheets

Figure 2A:
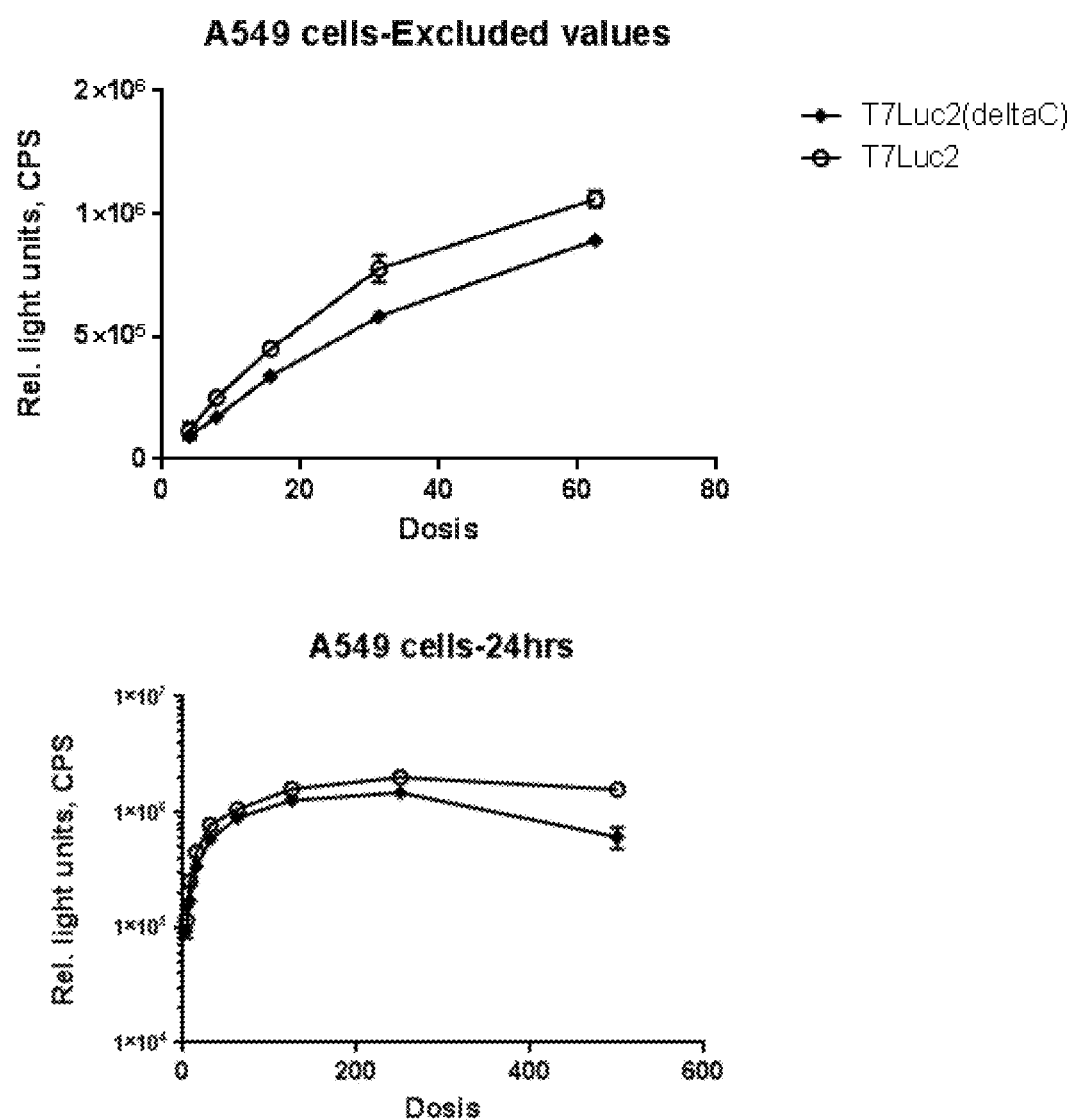

Specification includes a Sequence Listing.

(56) References Cited

OTHER PUBLICATIONS

Database GenBank, Jan. 29, 2011, Anonymous: "BJ302563 Y. Ogihara unpublished cDNA library, Wh_yd Triticum aestivum cDNA clone whyd15n04 5-, mRNA sequence," XP002764164, Database accession No. BJ302563 sequence.
Database GenBank NCBI, Jan. 29, 2011, Anonymous: "RST8012 Athersys RAGE Library *Homo sapiens* cDNA, mRNA sequence," XP002764165, Database accession No. BG188977 sequence.
Database Nucleotide NCBI; Aug. 11, 2006, Anonymous: "Danio rerio heat shock cognate 70-kd protein, mRNA (cDNA clone MGC: 65778 Image:6789418), complete cds," XP002764166, database accession No. BC056709 sequence.
Database GenBank NCBI; Mar. 14, 2005, Anonymous: "AU247853 FL Lolium multiflorum cDNA clone FL038H04-5, mRNA sequence," XP002764167, Database accession No. AU247853 sequence.
R. Elfakess, et al.: "Unique Translation Initiation of mRNAs-containing TISU element," Nucleic Acids Research, vol. 39, No. 17, Sep. 1, 2011, pp. 7598-7609, XP055316852, GB.
R. elfakees, et al.: "A Translation Initiation Element Specific to mRNAs with Very Short 5'UTR that Also Regulates Transcription," PLOS One, vol. 3, No. 8, Aug. 28, 2008, p. e3094, XP055318491.
L. Li, et al., "Capped mRNA with a Single Nucleotide Leader Is Optimally Translated in a Primitive Eukaryote, *Giardia lamblia*," Journal of Biological Chemistry, vol. 279, No. 15, Apr. 9, 2004, pp. 14656-14664., XP055316900, US.
Marilyn Kozak, "An analysis of 5'-noncoding sequences from 699 vertebrate messenger RNAs," Nucleic Acids Research, vol. 15, No. 20, Jan. 1, 1987, pp. 8125-8148, XP055318604.
Michael S.D. Kormann, et al., "Expression of therapeutic proteins after delivery of chemically modified mRNA in mice," Nature Biotechnology, vol. 29., No. 2, Feb. 1, 2011, pp. 154-157, XP055040839.
International Search Report for International Application No. PCT/EP2017/057592, dated Jul. 4, 2017.
Extended European Search Report for Application No. EP 16163264.1, dated Dec. 6, 2016.
Wada, Kazuhiro, et al. "A molecular neuroethological approach for identifying and characterizing a cascade of behaviorally regulated genes." *Proceedings of the National Academy of Sciences* 103.41 (2006): 15212-15217.
OST448298 Mus musculus 129Sv/Ev Mus musculus cDNA clone OST448298, genomic survey sequence, GenBank: CG663293.1, Gen Bank, 1.
UP 296-8P T7 RPCI11 Human Male BAC Library *Homo Sapiens* genomic clone RP11-296P8, genomic survey sequence, GenBank: Az301211.2, GenBank, 1-2.

\* cited by examiner

1.) ...TATAGGGAGACGCCACCATG     T7Luc2 (SEQ ID NO:37)

2.) ...TATAGGGAGAGCCACCATG     T7Luc2 (ΔC) (SEQ ID NO:38)

3.) ...TATAGGGAGACAGCCACCATG     T7Luc2 (+8+A) (SEQ ID NO:39)

4.) ...TATAGGGAGACTGCCACCATG     T7Luc2 (+8+T) (SEQ ID NO:40)

5.) ...TATAGGGAGACGGCCACCATG     T7Luc2 (+8+G) (SEQ ID NO:41)

6.) ...TATAGGGAGACCGCCACCATG     T7Luc2 (+8+C) (SEQ ID NO:42)

7.) ...TATAGGGAGACSp30GCCACCATG     T7Luc2 (+8+Sp30) (SEQ ID NO:43)

8.) ... TATAGGGAGAC<u>TCTTCTGGTCCCCACAGACTCAGAGAAC</u>GCCACCATG     T7Luc2 (+8+hAg) (SEQ ID NO:44)

9.) ...TATAGGGAGACTGCCAAGATG     T7Luc2 (+8+T)+TISU (SEQ ID NO:45)

Sp30: a random sequence of 30 nucleotides

<u>underlined</u> in sequence No. 8): 5'UTR from human alpha globin (hAg) (30 nucleotides in length)

Figure 1

MINIMAL UTR SEQUENCES

RELATED APPLICATIONS

This application is a national stage filing under 35 U.S.C. 371 of International Application No.: PCT/EP2017/057592, filed Mar. 30, 2017, which claims priority to European Application No. 16163264.1 filed Mar. 31, 2016, and European Application No. 16177094.6 filed Jun. 30, 2016, the entire teachings of which are incorporated herein by reference. International Application No.: PCT/EP2017/057592 was published under PCT Article 21(2) in English.

The present invention relates to DNA molecules which can be transcribed into an mRNA harbouring novel UTR sequences combining the advantages of being extremely short and at the same time allowing for high translation efficiencies of RNA molecules containing them. Further, the present invention relates to vectors comprising such a DNA molecule and to host cells comprising such a vector. Moreover, the present invention relates to corresponding RNA molecules containing such UTRs. Further, the present invention relates to a pharmaceutical composition comprising the described RNA molecule and optionally a pharmaceutically acceptable carrier as well as to the use of the described UTRs for translating a coding region of an RNA molecule into a polypeptide or a protein encoded by said coding region.

In recent years, messenger RNA (mRNA) has become increasingly relevant as a new drug entity. As opposed to DNA-based gene therapeutics, mRNA does not need to be transported into the nucleus but is directly translated into protein in the cytoplasm (J Control Release, 2011, 150:238-247, and Eur J Pharm Biopharm, 2009, 71:484-489). This makes mRNA safer in avoiding potential insertional mutagenesis, an unlikely but existent risk of DNA gene medicines. As a consequence, mRNA therapeutics are emerging as promising alternatives for gene and protein replacement therapies in a broad variety of medical indications (J Control Release, 2011, 150:238-247; Eur J Pharm Biopharm, 2009, 71:484-489; Nat Biotech, 2011, 29:154-157, and Nat Rev Genet, 2011, 12:861-874). However, the strong immunogenicity as well as the limited stability of conventional mRNA has to be overcome to further establish its clinical applicability. With respect to this, mRNA stability and in particular the translation rate of the mRNA is an essential parameter for envisaged medical applications because it determines, for example, dosing and the dosing intervals of mRNA drugs.

Several strategies have proven successful both at increasing the stability and reducing the immunogenic response triggered by mRNA administered to cells or organisms. Amongst these is the inclusion of chemically modified nucleotides; Current Opinion in Drug Discovery and Development, 2007, 10:523. Kormann et al. have shown that the replacement of only 25% of uridine and cytidine residues by 2-thiouridine and 5-methyl-cytidine suffices to increase mRNA stability as well as to reduce the activation of innate immunity triggered by externally administered mRNA in vitro (WO2012/0195936 A1; WO2007024708 A2).

Also, untranslated regions (UTRs) in mRNAs have been reported to play a pivotal role in regulating both mRNA stability and mRNA translation. UTRs are known to influence translational initiation, elongation, and termination, as well as mRNA stabilization and intracellular localization through their interaction with RNA binding proteins (Briefings in Bioinformatics, 2000, 1:236-249 and Cold Spring Harbor Monograph Archive, 2007, 48:87-128). Depending on the specific motives within the UTR, it can either enhance or decrease mRNA turnover (Cell. Mol. Life Sci., 2012, 69:3613-3634; Nucleic Acids Research, 2005, 33:D141-D146; Science, 2005, 309:1514-1518 and Current Protein & Peptide Science, 2012, 13:294-304). Recently, data on mRNA half-lives and the corresponding UTR sequences have been published (Nucleic Acids Research, 2011, 39:556-566 and Nucleic acids research, 37, e115).

UTRs are sections of an mRNA molecule upstream the start codon and downstream of the stop codon of an mRNA, i.e., sequences which are not translated. These regions are transcribed with the coding region and, thus, are exonic as they are present in the mature mRNA. The UTR upstream of the start codon of an mRNA is called 5' UTR and, once transcribed, harbours, inter alia, sequences which correspond to (residual 3') parts of the promoter as well as a so-called Kozak sequence.

The Kozak consensus sequence, Kozak consensus or Kozak sequence, is a sequence which is known to occur in eukaryotic mRNA and has the consensus (gcc)gccRccAUGG. The Kozak consensus sequence plays a major role in the initiation of the translation process. The sequence was named after the person who brought it to prominence, Marilyn Kozak. This sequence in an mRNA molecule is recognized by the ribosome at the translational start site, from which a protein is coded by that mRNA molecule. The ribosome requires this sequence, or a possible variation thereof to initiate translation. The sequence is identified by the notation (gcc)gccRccAUGG, which summarizes data analysed by Kozak from a wide variety of sources (about 699 in all) as follows: a lower case letter denotes the most common base at a position where the base can nevertheless vary; upper case letters indicate highly conserved bases, i.e. the "AUGG" sequence is constant or rarely, if ever, changes, "R" which indicates that a purine (adenine or guanine) is always observed at this position (with adenine being claimed by Kozak to be more frequent); and the sequence in brackets ((gcc)) is of uncertain significance.

The Kozak consensus sequence was originally defined as ACCAUGG due to an analysis of point mutations around the initiation codon (AUG, with A defining in this context the position +1) on translation of the preproinsulin gene. More detailed mutagenesis of 699 vertebrate mRNAs resulted in the consensus sequence GCCGCCACCAUGG, where the A upstream the AUG start codon at position −3 could also be a G (Nucleic Acids Res., 1987, 15 (20):8125-8148). Studies on preproinsulin and alpha-globin translation in eukaryotic cells revealed that a purine (usually A) at position −3 is essential for efficient translation initiation and if this purine is missing a G at position +4 is essential (J. Cell Biol., 1989, 108:229-41). The amount of protein synthesized from an mRNA molecule strongly depends on the sequence of the Kozak element: the AUG start codon, encoding the N-terminal methionine of the protein, is most important. For a strong consensus, the nucleotides at positions +4 (G) and −3 (A or G) must both match the consensus. An adequate consensus sequence has only one of these two sites, while a weak consensus sequence does neither fulfill the requirements at positions +4 nor on −3. The two cytidine residues at −1 and −2 are not that much conserved (Cell, 1986, 44 (2):283-92), while the G at position −6 is important for the initiation of translation (Br. J. Haematol., 2004, 124 (2): 224-31).

Although in the prior art there are already described means and methods for increasing the stability of mRNA, reducing the immunogenic response triggered by mRNA administered to cells or organisms and increasing the expression efficiency (i.e., the transcription and/or translation efficiency) there is still a need for improvements, in particular as regards further or alternate means to increase the expression efficiency (i.e., the transcription and/or translation efficiency) since the expression efficiency is an essential parameter for envisaged medical applications because it determines, for example, dosing and the dosing intervals of mRNA drugs and, ultimately, determines the bioavailability of the final product, i.e., the encoded peptide or protein. At the same time, there is a constant need for further decreasing the costs for the production of mRNA drugs, increasing the yield of the produced mRNA molecules and increasing the available space in the produced mRNA molecule for the actual transgene, i.e., for the coding region coding for a desired polypeptide.

The present application addresses this need by providing the embodiments as defined in the claims.

In particular, the present application surprisingly found that it is possible to reduce the size of the UTR sequence to a "minimal UTR" sequence, thereby decreasing the costs for the production of mRNA drugs, increasing the yield of the produced mRNA molecules and increasing the available space in the produced mRNA molecule for the actual transgene, i.e., for the coding region coding for a desired polypeptide. Moreover, at the same time, this minimal UTR sequence surprisingly retains or even improves the expression rate over conventional UTR sequences while it has been found that modifications in this minimal UTR sequence even increase the expression rate of the mRNA molecule.

This finding leads to the provision of the embodiments as characterized in the claims, in particular to the provision of DNA molecules which allow the production of RNA molecules harbouring such a "minimal UTR" sequence as well as the provision of the corresponding RNA molecules.

In a first aspect, corresponding molecules are described on the DNA-level while further below, in a second aspect, corresponding molecules are described on the RNA-level.

Thus, in a first aspect, the present invention relates to a DNA molecule, which can be transcribed into an mRNA, wherein said DNA molecule comprises one strand with the following elements:
(a) a coding region, including a start codon at its 5' end, coding for a polypeptide; and
(b) directly upstream of said coding sequence a sequence selected from the group consisting of:
(b1)

$R_1$-CGCCACC; (SEQ ID NO: 1)

or a sequence wherein in said sequence the C at position 6 of SEQ ID NO:1 is substituted by an A and the C at position 7 of SEQ ID NO:1 is substituted by a G; and/or the A at position 5 of SEQ ID NO:1 is substituted by a G; and (b2) $R_1$-CNGCCACC (SEQ ID NO:2), wherein the nucleotide N at position 2 of SEQ ID NO:2 is a nucleotide selected from the group consisting of T, G, C or A;

or a sequence wherein in said sequence the C at position 7 of SEQ ID NO:2 is substituted by an A and the C at position 8 of SEQ ID NO:2 is substituted by a G; and/or the A at position 6 of SEQ ID NO:2 is substituted by a G, wherein $R_1$ is a promoter which is recognized by a DNA-dependent RNA-polymerase;
or comprising the complementary strand.

A DNA sequence is called "sense" if its sequence is the same as that of a messenger RNA copy that is translated into a protein. The sequence on the opposite, complementary, strand is called the "antisense" sequence. The DNA molecule of the present invention is defined in (a) and (b), above, by reference to the sense strand while the corresponding complementary, antisense-strand can easily be determined by the skilled person given the base pairing rules.

The DNA molecule of the present invention is a DNA molecule which can be transcribed into an mRNA molecule. Transcription is the first step of gene expression, in which a particular segment of a DNA molecule is copied into an mRNA molecule by the enzyme RNA polymerase. During transcription, a DNA sequence is read by an RNA polymerase, which produces a complementary, anti-parallel RNA strand called a primary transcript.

Only one of the two DNA strands serves as a template for transcription. The antisense strand of DNA is read by a DNA-dependent RNA polymerase from the 3' end to the 5' end during transcription (3'→5'). The complementary RNA is created in the opposite direction, in the 5'→3' direction, matching the sequence of the sense strand with the exception of switching uracil for thymine. This directionality is because RNA polymerase can only add nucleotides to the 3' end of the growing mRNA chain. The non-template sense strand of DNA is called the coding strand, because its sequence is the same as the newly created RNA transcript (except for the substitution of uracil for thymine). This is the strand that is used by convention and in the context of the present invention when presenting a DNA sequence.

The DNA molecule of the present invention can be double-stranded or single-stranded or partly double-stranded and partly single-stranded.

A DNA molecule of the present invention comprises two main modules (also referred to as "items"), i.e., (a) a coding region coding for a polypeptide and which includes a start codon at its 5'-end, and (b) directly upstream of said coding region a sequence as defined in (b1) or (b2) herein-above. Such a DNA molecule, when transcribed, leads to an mRNA with an extremely short UTR sequence conferring the above described advantages.

In addition, the DNA molecule of the present invention preferably comprises a sequence which, when transcribed into mRNA, results in a UTR downstream of the coding region. Thus, the DNA molecule of the present invention preferably harbours a coding region as well as sequences which, upon transcription, result in (5' and 3') untranslated regions (UTRs) in the produced mRNA molecule.

The term "coding region including a start codon at its 5' end" as used in accordance with the present invention relates to a DNA sequence which is composed of codons, which are transcribed into an mRNA molecule by a DNA-dependent RNA-polymerase wherein a corresponding mRNA molecule may be decoded and translated into proteins by the ribosome in accordance with the information provided by the "genetic code". Coding regions commonly begin with a start codon at their 5' end and end with a stop codon. In general, the start codon is an ATG triplet (corresponding to an AUG triplet on the RNA level) and the stop codon is TAA, TAG or TGA (corresponding to UAA, UAG, or UGA on the RNA level). In addition to being protein-coding, portions of coding regions may serve as regulatory sequences in the pre-mRNA as exonic splicing enhancers or exonic splicing silencers. The coding region of a gene coding for a polypeptide or a protein as used in accordance with the present invention is also known as the coding sequence or CDS (from coding DNA sequence) and is that portion of a gene's DNA or RNA, composed of exons, that codes for a polypeptide or protein. The coding region in mRNA is flanked by the 5'-untranslated region (5' UTR) and the 3'-untranslated region (3' UTR) which are also parts of the exons. Moreover, mRNA molecules may further comprise a so-called 5' cap and a poly-A tail. The 5' cap, the 5' UTR, the 3' UTR and the poly-A tail are regions of an mRNA molecule which are not translated into protein.

The term "untranslated region" or "UTR" as used in accordance with the present invention relates to sections of an mRNA upstream of the start codon and downstream of the stop codon that are not translated, and are, therefore, termed the five prime untranslated region (5' UTR) and three prime untranslated region (3' UTR), respectively. These regions are transcribed with the coding region and thus are exonic as they are present in the mature mRNA.

As used in the present invention, the 3' untranslated region (3'-UTR) relates to the section of messenger RNA (mRNA) that immediately follows the translation termination codon. The 3' UTR may comprise regulatory regions within the 3'-untranslated region which are known to influence polyadenylation and stability of the mRNA. Many 3'-UTRs also contain AU-rich elements (AREs). Furthermore, the 3'-UTR may preferably contain the sequence AAUAAA that directs addition of several hundred adenine residues called the poly(A) tail to the end of the mRNA transcript. The 5' untranslated region (5' UTR) (also known as a Leader Sequence or Leader RNA) is the region of an mRNA that is directly upstream of the start codon. The 5' UTR begins at the transcription start site and ends one nucleotide (nt) before the start codon (usually AUG in the mRNA) of the coding region. In eukaryotes the length of the 5' UTR is generally from 100 to several thousand nucleotides long but sometimes also shorter UTRs occur in eukaryotes.

In the present invention, the sequence between the promoter and the coding region (as defined in (b1) or (b2), above), is extremely short and leads, upon transcription, to an mRNA molecule with a very short "minimal" UTR sequence.

One module of the DNA molecule, i.e., "a coding region including a start codon at its 5' end coding for a polypeptide" (module (a)) is not particularly limited and may be any desired coding region which is to be expressed in a given cell. Thus, this module may be a coding region coding for a desired polypeptide, i.e., the desired final product. The present invention is not limited with respect to the "coding region including a start codon at its 5' end coding for a polypeptide" since the nature of the coding region depends on the desired product which is to be produced in the cell. Such coding region can also be a nucleotide sequence which differs from a known natural sequence and contains mutations (i.e. point mutations, insertion mutation, deletions and combinations thereof). Moreover, such a coding region may partly or to the full extent be a codon optimized sequence derived from the natural sequence to be used as module (a). Codon optimization is a technique to maximize the protein expression by increasing the translational efficiency of the mRNA derived from a gene of interest. It is known that natural genes do not use the available codons randomly, but show a certain preference for particular codons for the same amino acid. Thus, because of the degeneracy of the genetic code—one amino acid can be encoded by several codons—transforming the nucleotide sequence of a gene of interest into a set of preferred codons of the same or another species.

As mentioned, module (a) is not particularly limited and may be any desired coding region which is to be expressed in a given cell. Thus, in the context of the present invention, "coding region" should be understood to mean any polydesoxyribonucleotide molecule which, if introduced into a cell, can be transcribed into an mRNA molecule which is translatable to a polypeptide/protein or fragment thereof. The terms "polypeptide" and "protein" here encompass any kind of amino acid sequence, i.e., chains of two or more amino acids which are each linked via peptide bonds and also includes peptides and fusion proteins.

In a preferred embodiment, the "coding region including a start codon at its 5' end coding for a polypeptide" contains a desoxyribonucleotide sequence which encodes a polypeptide/protein or fragment thereof whose function in the cell or in the vicinity of the cell is needed or beneficial, e.g., a protein the lack or defective form of which is a trigger for a disease or an illness, the provision of which can moderate or prevent a disease or an illness, or a protein which can promote a process which is beneficial for the body, in a cell or its vicinity. The coding region may contain the sequence for the complete protein or a functional variant thereof. Further, the desoxyribonucleotide sequence of the coding region can encode a protein which acts as a factor, inducer, regulator, stimulator or enzyme, or a functional fragment thereof, where this protein is one whose function is necessary in order to remedy a disorder, in particular a metabolic disorder or in order to initiate processes in vivo such as the formation of new blood vessels, tissues, etc. Here, functional variant is understood to mean a fragment which in the cell can undertake the function of the protein whose function in the cell is needed or the lack or defective form whereof is pathogenic.

In a preferred embodiment, the "coding region including a start codon at its 5' end coding for a polypeptide" encodes a therapeutically or pharmaceutically active polypeptide or protein having a therapeutic or preventive effect. As such, the DNA molecule of the present invention which can be transcribed into an mRNA comprising said "coding region including a start codon at its 5' end coding for a polypeptide" may be used in nucleic acid therapy and related applications. In this context, in accordance with the invention, the transcription and translation of a DNA molecule of the present invention into an mRNA and further into a polypeptide or a protein may be intended to compensate or complement endogenous gene expression, in particular in cases where an endogenous gene is defective or silent, leading to no, insufficient or a defective or a dysfunctional product of gene expression such as is the case with many metabolic and hereditary diseases like cystic fibrosis, hemophilia or muscular dystrophy to name a few. The transcription and translation of a DNA molecule of the present invention into an mRNA and further into a polypeptide or a protein may also be intended to have the product of the expression interact or interfere with any endogenous cellular process such as the regulation of gene expression, signal transduction and other cellular processes. The transcription and translation of a DNA molecule of the present invention into an mRNA and further into a polypeptide or a protein may also be intended to give rise to an immune response in context of the organism in which a transfected or transduced cell resides or is made to reside. Examples are the genetic modification of antigen-presenting cells such as dendritic cells in order to have them present an antigen for vaccination purposes. Another example is the transcription and translation of a DNA molecule of the present invention into an mRNA and further into a polypeptide or a protein wherein said coding region encodes cytokines. This may, e.g., be desirable in tumors in order to elicit a tumor-specific immune response.

Furthermore, transcription and translation of a DNA molecule of the present invention into an mRNA and further into a polypeptide or a protein may also be intended to generate in vivo or ex vivo transiently genetically modified cells for cellular therapies such as modified T-cells or precursor or stem or other cells for regenerative medicine.

In other preferred embodiments, the "coding region including a start codon at its 5' end coding for a polypeptide" may encode a protein which plays a part in growth processes and angiogenesis, which are for example necessary in controlled regeneration and can then be formed specifically by introduction of the RNA molecule according to the invention. This can for example be useful in growth processes or for the treatment of bone defects, tissue defects and in the context of implantation and transplantation.

As mentioned, the DNA molecule and, in particular the correspondingly transcribed RNA molecule of the present invention comprising a "coding region including a start codon at its 5' end coding for a polypeptide" can appropriately be used in any case where a polypeptide or a protein, which would naturally be present in the body but is not present or is present in deficient form or in too small a quantity because of gene defects or diseases, is to be provided to the body. Proteins and the genes encoding them, the deficiency or defect whereof are linked with a disease, are known. The respective intact version of the coding region coding for the intact polypeptide or protein can be used in accordance with the present invention.

Numerous genetic disorders, caused by the mutation of a single gene are known and candidates for mRNA therapeutic approaches. Disorders caused by single-gene mutations, like cystic fibrosis, hemophilia and many others, can be dominant or recessive with respect to the likelihood that a certain trait will appear in the offspring. While a dominant allele manifests a phenotype in individuals who have only one copy of the allele, for a recessive allele the individual must have two copies, one from each parent to become manifest. In contrast, polygenic disorders are caused by two or more genes and the manifestation of the respective disease is often fluent and associated to environmental factors. Examples for polygenic disorders are hypertension, elevated cholesterol level, cancer, neurodegenerative disorders, mental illness and others. Also in these cases therapeutic mRNA representing one or more of these genes may be beneficial to those patients. Furthermore, a genetic disorder must not have been passed down from the parents' genes, but can also be caused by new mutations. Also in these cases therapeutic mRNA representing the correct gene sequence may be beneficial to the patients.

An online catalog with presently 22,993 entries of Human Genes and Genetic Disorders together with their respective genes and a description of their phenotypes are available at the ONIM (Online Mendelian Inheritance in Man) webpage (http://onim.org); sequences of each are available from the Uniprot database (http://www.uniprot.org). As non-limiting examples, the following Table 1 lists some congenital diseases, and the corresponding gene(s). Due to the high degree of interaction of cellular signaling pathways, the mutation of a certain gene causes a multiply of pathogenic symptoms, of which only a characteristic one is listed in Table 1.

In some embodiments of the present invention, the therapeutic protein is chosen from the cellular proteins listed in Table 1. Thus, the DNA molecule of the invention may encode a therapeutic cellular protein, wherein the encoded therapeutic protein is one listed in Table 1 or a homolog thereof.

In another embodiment of the present invention, the therapeutic protein is chosen from the secreted proteins listed in Table 1. Thus, the DNA molecule of the invention may encode a therapeutic fusion protein, wherein the encoded therapeutic protein or a homolog thereof is one listed in Table 1 and the second protein is a signal peptide that allows the secretion of the therapeutic protein. A signal peptide is a short, typically 5-30 amino acids long, amino acids sequence present at the N-terminus of said therapeutic protein and that leads the fusion protein towards the cell's secretory pathway via certain organelles (i.e. the endoplasmic reticulum, the golgi-apparatus or the endosomes). Thus, such fusion protein is secreted from the cell or from a cellular organelle or inserted into a cellular membrane (e.g. multi-spanning trans-membrane proteins) at a cellular compartment or at the cell's surface.

Thus, in preferred embodiments of the present invention the "coding region including a start codon at its 5' end coding for a polypeptide" (module (a)) may encode, but is not limited to, the following genes that cause, predispose or protect from diseases. Non-limiting examples of such disorders that may be treated (or prevented) include those wherein said polypeptide, protein or peptide is selected from the group consisting of the ones as outlined in the following Table 1.

In some embodiments, the "coding region including a start codon at its 5' end coding for a polypeptide" may be transcribed and translated into a partial or full length protein comprising cellular activity at a level equal to or greater than that of the native protein. In some embodiments, the "coding region including a start codon at its 5' end coding for a polypeptide" encodes a therapeutically or pharmaceutically active polypeptide, protein or peptide having a therapeutic or preventive effect, wherein said polypeptide, protein or peptide is selected from the group consisting of the ones as outlined in the following Table 1. The "coding region including a start codon at its 5' end coding for a polypeptide" may be used to express a partial or full length protein with cellular activity at a level equal to or less than that of the native protein. This may allow the treatment of diseases for which the administration of an RNA molecule can be indicated.

TABLE 1

| Non-limiting examples of human genes and genetic disorders | | |
|---|---|---|
| Disease | Pathology | Gene, heredity |
| Blood diseases | | |
| Fanconi Anemia | Anemia and neutropenia, evidence that a DNA repair mechanism is affected | FANCA, autosomal recessive |
| Hemophilia-A | Abnormal bleeding | Coagulation Factor VIII, X-chromosomal recessive |

TABLE 1-continued

Non-limiting examples of human genes and genetic disorders

| Disease | Pathology | Gene, heredity |
|---|---|---|
| Hemophilia-B | Abnormal bleeding | Coagulation Factor IX, X-chromosomal recessive |
| Hereditary Spherocytosis (various types) | spherical-shaped erythrocytes (spherocytes) | Ankyrin (ANK1) |
| Paroxysmal nocturnal hemoglobinuria | Anemia and presence of blood in the urine | PIG-A, X-chromosomal |
| Porphyria cutanea tarda | Overproduction of heme, iron overload | Uroporphyrinogen decarboxylase (UROD), autosomal recessive |
| Severe combined immune deficiency (SCID) | Due to impaired DNA synthesis severe immune deficiency in humoral and cellular immunity | Adenosine deaminase, autosomal recessive, IL-2R-$\gamma$, JAK3, (IL-7R-$\alpha$, RAG1/2, Artemis, CD3$\delta$, CD3$\varepsilon$ |
| Sickle-cell anemia | Abnormal hemoglobin (HbS) | $\beta$-Hemoglobin (HB), autosomal recessive |
| Thalassemia ($\alpha$- and $\beta$ form) | Lack of $\alpha$- or $\beta$ hemoglobin resulting in anemia | Deletion of HBA1 and/or HBA2, |
| Von Willebrand disease (three types known, Type-III is most severe) | Abnormal bleeding, hemorrhage similar to hemophilia A and B | Autosomal dominant and recessive forms |

Cancer

| Disease | Pathology | Gene, heredity |
|---|---|---|
| Malignant melanoma | P16 mutation leads to uncontrolled proliferation of fibroblasts | Cyclie dependant kinase inhibitor 2 (CDKN2) |
| Neurofibromatosis (2 types) | Benign tumors on auditory nerves leads to deafness | NF1, NF2, autosomal dominant |

Deafness (Ear)

| Disease | Pathology | Gene, heredity |
|---|---|---|
| Deafness | Hearing loss | Deafness-1A (DFNB1), autosomal recessive |
| Pendred syndrome | Hearing loss | Pendrin (PDS), autosomal recessive |

Heart

| Disease | Pathology | Gene, heredity |
|---|---|---|
| Ataxia telangiectasia | DNA damage repair disturbed, | ATM, |
| Atherosclerosis | Increase of blood cholesterol | apoE, |
| LQT Syndrome (Long QT) | Potassium channel defect | LQT1 and other genes |
| Von-Hippel Lindau Syndrome | Abnormal growth of blood vessels, can lead to cancer | VHL, autosomal dominant |
| William's Beuren Syndrome | Deletion of elastin results in vascular defects, supravalvular aortic stenosis | Deletion of elastin and LIM kinase genes |

Metabolic disorders and glycogen storage diseases

| Disease | Pathology | Gene, heredity |
|---|---|---|
| Adrenoleukodystrophy | Disturbed fatty acid transport and metabolism | ABCD1, X-chromosomal |
| Alkaptonuria | Nitrogen metabolism defect, Urine turns dark when exposed to oxygen | Homogentisic Oxidase, autosomal recessive |
| Diabetes type I | Disturbed insulin production | IDDM1, IDDM2, GCK, . . . |
| Galactosemia | disorder of galactose metabolism | Galactose-1-phosphate uridyltransferase gene (GALT), autosomal recessive |
| Gauche disease | Disturbance of fat metabolism | Glucocerebrosidase |
| Glucose Galactosidase Malabsorption | Disturbed glucose and galactose transport out of the intestinal lumen resulting in diarrhea | SGLT1, autosomal recessive |

TABLE 1-continued

Non-limiting examples of human genes and genetic disorders

| Disease | Pathology | Gene, heredity |
| --- | --- | --- |
| Glycogen storage disease Type I, Von-Gierke's disease | Accumulation of glucose in liver and kidney | Glucose-6-Phosphatase, autosomal recessive |
| Glycogen storage disease Type II, Pompe's disease | Accumulation of glycogen in liver, heart, skeletal muscle, cardiomegaly | α-1-Glucosidase, autosomal recessive |
| Glycogen storage disease Type III, Cori's disease | Accumulation of glycogen in liver, heart, skeletal muscle, hepatoomegaly | Debranching enzyme, autosomal recessive |
| Glycogen storage disease Type V, McArdle's disease | Cannot untilize glycogen in muscle cells | Muscle phosphorylase, autosomal recessive |
| Glucose-6-Phosphate Dehydrogenase | Inability to maintain glutathione leads to hemolytic anemia | G6PD, X-chromosomal recessive |
| Hereditary Hemochromatosis (4 types) | Excess of iron in the body (esp. liver) due to excessive iron absorption in the gut | Hemochromatosis (HFE) |
| Homocystinuria | Nitrogen metabolism defect | Cystathione synthetase defect, autosomal recessive |
| Lesh Nyhan Syndrome | Accumulation of uric acid leading to gout, ureate stones and muscle loss | HPRT1, X-chromosomal |
| Maple Syrup Urine Disease | Amino acid metabolism defect leads to the accumulation of α-Ketoacides and death in the first months if untreated | Branched-chain-alpha-dehydrogenase (BCKDH) |
| Menkes' Syndrome | Reduced ability to absorb copper, leads to death in infancy if untreated | ATP7A, X-chromosomal recessive |
| Obesity | Elevated body weight | Polygenic, elevated leptin levels may play a role |
| Phenylketonuria | Inability to break down Phenylalanine into tyrosine leads to mental retardation | Phenylalanine hydroxylase (PAH), autosomal recessive |
| Tangier disease | reduced levels of plasma high density lipoproteins | ATP-binding cassette-1 gene (ABCA1) |
| Zellweger Syndrome (leads to death in infants) | High levels of iron and copper in the blood | PXR1 (receptor on the surface of peroxisomes) |
| Wilsons Disease | Copper accumulation in brain and liver | ATP7B (P-type ATPase), autosomal recessive |
| | Musculoskeletal system | |
| Achondroplasis | Short stature with a large head due to slow proliferation of chondrocytes | Fibroblast growth factor receptor 3 (FGF3R), |
| Charcot-Marie-Tooth Syndrome and its more severe form Dejerine-Sottas Syndrome | Degeneration of the muscles in limbs | Different forms caused by different gene mutations, autosomal recessive and X-chromosomal |
| Cockayne syndrome (2 types) | Premature aging and short stature, loss of "on the fly" DNA repair | group 8 excision repair cross-complementing protein (ERCC8) |
| Chondroectodermal dysplasia | Malformation of bones and polydactyly | EVC, autosomal recessive |
| Diastrophic dysplasia (DTD) | Malformed hands, sulfate transporter defect | DTDST gene |
| Duchenne muscular dystrophy | Enlargement of muscle tissue with subsequent loss of function | DMD, X-chromosomal recessive |

TABLE 1-continued

Non-limiting examples of human genes and genetic disorders

| Disease | Pathology | Gene, heredity |
|---|---|---|
| Fibrodysplasia Ossificans Progressiva | Heterotopic bone formation | NOG, BMP, Autosomal dominant |
| Friedreich's ataxia | Heart enlargement and progressive loss of muscular coordination | Frataxin, autosomal recessive |
| Hypophosphatasia | Production of an abnormal version of alkaline phosphatase affecting the mineralization process | ALPL, autosomal recessive |
| Marfan Syndrome | Connective tissue disorder due fibrillin deficiency | Fibrillin 1 (FBN), autosomal dominant |
| Myotonic dystrophy (onset during young adulthood) | Protein kinase defect in skeletal muscle cells | Dystrophia myotonica protein kinase (DMPK), autosomal dominant |
| Osteogenesis imperfect (various types) | Defect in type-I collagen formation leads to multiple fractures after birth | COL1A1, COL1A2 |
| Prader-Willi Syndrome | Decreased muscle tone and mental retardation | SNRPN (small ribinucleoprotein N) deleted due to a deletion on chromosome 15 |
| Neurons and Brain ||| 
| Alzheimer disease | Increased amyloid production, progressive inability to remember facts | Polygenic, PS1, PS2, . . . |
| Amyotrophic lateral sclerosis (ALS) (various forms) | Progressive degeneration of motor neuron cells (defect in elimination superoxide radicals) | Superoxide dismutase 1 (SOD1), various genes involved |
| Angelman syndrome | Mental retardation with inadequate laughing | Genomic imprinting on chromosome 15 |
| Pyruvat dehydrogenase | Neurological defects if untreated | Pyruvat dehydrogenase, autosomal recessive |
| Refsum disease | Accumulation of phytanic acid leads to peripheral neuropathy | Phytanoyl-CoA hydroxylase (PHYH), autosomal recessive |
| Rett's syndrome | Mental retardation with arrested development between 6 and 18 months of age | Methyl-CpG-binding protein-2 (MECP2), X-chromosomal dominant |
| Tay-Sachs disease (various forms of severity) | Disturbed break down of GM2 ganglioside leads to neurological damage | HEXA (β-hexosaminidas A), autosomal recessive |
| LaFora Disease | Aggressive form of epilepsy | EPM2A, autosomal recessive |
| Essential tremor (variable forms) | Uncontrollable shaking | ETM1, ETM2, autosomal dominant |
| Fragile X syndrome | Lack of FMR1 RNA binding protein, mental retardation | FMR1 gene is not expressed due to an CGG amplification in the 5'UTR region |
| Huntington's disease | Progressive dementia with onset in adulthood | HTT (huntingtin), autosomal dominant |
| Intestine ||| 
| Bartter's syndrome (3 types) | Renal disease | Kidney chloride channel B gene (CLCNKB), autosomal recessive |
| Polycystic kidney disease (2 types) | renal disease | PDK1, PDK2, autosomal dominant, there is also a autosomal recessive form known (ARPKD) |

TABLE 1-continued

Non-limiting examples of human genes and genetic disorders

| Disease | Pathology | Gene, heredity |
| --- | --- | --- |
| Lung | | |
| Alpha-1-antitrypsin | Defect alveoli due to uncontrolled release of elastase | SERPINA1, autosomal codominant |
| Asthma | Chronic inflammatory disorder of the airways | Polygenic |
| Cystic fibrosis | Excessively viscous mucous due to defective $Cl^-$ ion transport | CFTR (cystic fibrosis conductance transmembrane regulator), autosomal recessive |
| Surfactant metabolism dysfunction (various types) | Newborns are of normal body weight, but all fail to inflate | ATP-binding cassette transporter (ABCA3) |
| Primary ciliary dyskinesia | Excessively viscous mucous due to defective/missing cilia function | DNAI1, CCNO, CCDC40 among others |
| Lysosomal storage diseases | | |
| Fabry's disease | Beyond others, skin lesions due to the accumulation of ceramide trihexoside | α-Galactosidase A, X-chromosomal recessive |
| Gaucher's Disease Type-I: adult form (normal lifespan under treatment) Type-II: infantile form (death before age 1) Type-III: juvenile form (onset in early childhood, less severe than Type-II) | Accumulation of glucocerebrosides (gangliosides, sphingolipids) | Glucocerebrosidase, autosomal recessive, |
| Hunter's Syndrome | Accumulation of mucopolysaccharides | L-iduronosulfat sulfatase, X-chromosomal recessive |
| Hurler's Syndrome (death by age of 10) | Accumulation of mucopolysaccharides | α-L-iduronidase, autosomal recessive |
| Niemann-Pick Disease (three distinct forms A, B, C) | Defect in releasing Cholesterol from lysosomes, accumulation of Sphingomyelin | Sphingomyelinase, autosomal recessive |
| Tay-Sachs disease (death by age of 4) | Accumulation of $G_{M2}$ ganglioside in neuronal cells | Hexosaminidase A, autosomal recessive |
| Skin | | |
| Albinism | Nitrogen metabolism defect | Tyrosinase deficiency, autosomal recessive |
| Albinism, oculocutaneous, type II | Reduced biosynthesis of melanin pigment | OCA2, autosomal recessive |
| Ehlers-Danlos Syndrome (various types) | Diaphragmatic hernia. common, retinal detachment | Various defects in collagen synthesis |
| Epidermolysis bullosa (various types including EB simplex, Junctional EB, Dystrophic EB and Kindler syndrome) | Defects in maintenance of keratinocyte structural stability or adhesion of the keratinocyte to the underlying dermis | Epidermolysis bullosa macular type (EBM), Epidermolysis bullosa 3 progressiva (EBR3), Epidermolysis bullosa 4 pseudojunctual (EBR4), Desmoplakin (DSP), Plakophilin-1 (PKP1), kreatin (KRT5, KRT14), plectin (PLEC), ITGA6, integrin subunit (ITGB4), laminin subunits (LAMA3, LAMP3, LAMB3, LAMC2), collagen (COL17A1, COL7A1 (autosomal dominant), FERMT1, autosomal recessive |

TABLE 1-continued

Non-limiting examples of human genes and genetic disorders

| Disease | Pathology | Gene, heredity |
|---|---|---|
| Hartnup's disease | Defect in tryptophan uptake in the gastrointestinal tract, light-sensitive skin | SLC6A19, autosomal recessive |
| Hereditary Hemorrhagic Telangiectasia, Osler-Weber-Rendu Syndrome | Telangiectasia of the skin and mucous membranes | Endoglin (ENG), autosomal dominant |
| Hypercholesterolemia, familial | elevation of serum cholesterol bound to low density lipoprotein, accumulation in skin and arteriosclerosis | Low-density lipoprotein receptor (LDLR), apolipoprotein B (APOB), autosomal dominant |
| Xeroderma pigmentosa | skin defect and melanoma due to UV exposure | DNA repair defect, autosomal recessive |
| Male pattern baldness | Disturbed conversion of testosterone into dihydrotestosterone in the skin | 5-α-reductase |
| Genetic liver diseases | | |
| Amino acid metabolism disorders | Disruptions in the multistep process that breaks down the amino acid tyrosine and phenylalanine | FAH, TAT, HPD, autosomal recessive |
| Beta-thalassemia intermedia | Shortage of mature red blood cells | HBB, autosomal recessive |
| Crigler-Najjar syndrome | Deficiency in glucuronidation in which bilirubin gets dissolvable in water | UGT1A1, autosomal recessive |
| Fatty acid oxidation disorders | Deficiency in processing of long-chain fatty acids and very long-chain fatty acids resulting in lethargy and hypoglycemia | HADHA, ACADVL autosomal recessive |
| Fructose metabolism disorders | Impaired gluconeogenesis causing hypoglycemia | FBP1, ALDOB, autosomal recessive |
| Galactosemia | Deficiency in processing galactose | GALT, GALK1, GALE, autosomal recessive |
| Glycogen storage diseases | Disturbed breakdown of glucose 6-phosphate and glycogen leads to accumulation of glycogen as well as abnormal glycogen molecules causing cell damage | G6PC, SLC37A4, AGL, GBE1, autosomal recessive |
| Heme biosynthesis disorder | Decrease of uroporphyrinogen decarboxylase resulting in accumulation of compounds called porphyrins causing toxic levels in liver | UROD autosomal dominant, ALAS2 X-limked dominant, ALAD autosomal recessive |
| Lipid metabolism (transport) disorders | Shortage of functional protein, which prevents movement of cholesterol and other lipids, leading to their accumulation in cells | NPC1, NPC2 autosomal recessive, LDLR, autosomal dominant |
| Metal metabolism disorders | Disorders in the storage and transport of iron and copper resulting in accumulation in tissues and organs | ATP7B, HAMP, HFE, HFE2, autosomal recessive |

TABLE 1-continued

Non-limiting examples of human genes and genetic disorders

| Disease | Pathology | Gene, heredity |
|---|---|---|
| Organic acid disorders (Acidurias/Acidemias) | Disrupted break down of several protein building blocks (amino acids), certain lipids, and cholesterol | BCKDHA, BCKDHB, and DBT, POCA and PCCB, MUT, MMAA, MMAB, MMADHC, MCEE, IVD, MCCC1 or MCCC2, autosomal recessive |
| Primary hyperoxaluria type 1 | Disrupted breakdown of glyoxylate leading to renal damage | AGXT, GRHPR, autosomal recessive |
| Progressive familial intrahepatic cholestasis | Buildup of bile acids in liver cells causing liver damage | ATP8B1, autosomal recessive |
| Thrombocyte activity disorder | Lack of enzyme activity disrupts the usual balance between bleeding and clotting | ADAMTS13, autosomal recessive |
| Urea cycle disorders | Disorder of the urea cycle which causes a form of hyperammonemia | OTC (X-linked disorder), CPS1, ASS1 and SLC25A13, ASL, autosomal recessive |

The above Table 1 shows examples of genes in which a defect leads to a disease which can be treated with the RNA molecule transcribed from the DNA molecule of the present invention wherein the DNA molecule (and the correspondingly transcribed RNA molecule) comprises a "coding region including a start codon at its 5' end coding for a polypeptide" which encodes an intact version of the protein or a functional fragment thereof of the above disclosed defective gene. In particularly preferred embodiments, hereditary diseases can be mentioned which for example affect the lungs, such as SPB (surfactant protein B) deficiency, ABCA3 deficiency, cystic fibrosis and α1-antitrypsin deficiency, or which affect plasma proteins (e.g. congenital hemochromatosis (hepcidin deficiency), thrompotic thrombocytopenic purpura (TPP, ADAMTS 13 deficiency) and cause clotting defects (e.g. haemophilia a and b) and complement defects (e.g. protein C deficiency), immune defects such as for example SCID (caused my mutations in different genes such as: RAG1, RAG2, JAK3, IL7R, CD45, CD3δ, CD3ε) or by deficiencies due to lack of adenosine desaminase for example (ADA-SCID), septic granulomatosis (e.g. caused by mutations of the gp-91-phox gene, the p47-phox gene, the p67-phox gene or the p33-phox gene) and storage diseases like Gaucher's disease, Fabry's disease, Krabbe's disease, MPS I, MPS II (Hunter syndrome), MPS VI, Glycogen storage disease type II or muccopolysacchaidoses.

Other disorders for which the present invention comprising a "coding region including a start codon at its 5' end coding for a peptide" can be useful include disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; Fabry disease; and Wilson's disease.

In all these diseases, a protein, e.g. an enzyme, is defective, which can be treated by treatment with the RNA transcribed from the DNA molecule of the present invention, which makes the protein encoded by the defective gene or a functional fragment thereof available. Transcript replacement therapies/enzyme replacement therapies do not affect the underlying genetic defect, but increase the concentration of the enzyme in which the patient is deficient. As an example, in Pompe's disease, the transcript replacement therapy/enzyme replacement therapy replaces the deficient Lysosomal enzyme acid alpha-glucosidase (GAA).

Thus, non-limiting examples of proteins which can be encoded by the "coding region including a start codon at its 5' end coding for a polypeptide" of module (a) according to the invention are erythropoietin (EPO), growth hormone (somatotropin, hGH), cystic fibrosis transmembrane conductance regulator (CFTR), growth factors such as GM-SCF, G-CSF, MPS, protein C, hepcidin, ABCA3 and surfactant protein B. Further examples of diseases which can be treated with the RNA according to the invention are hemophilia A/B, Fabry's disease, CGD, ADAMTS13, Hurler's disease, X chromosome-mediated A-γ-globulinemia, adenosine deaminase-related immunodeficiency and respiratory distress syndrome in the newborn, which is linked with SP-B. Particularly preferably, the "coding region including a start codon at its 5' end coding for a polypeptide" of the DNA molecule according to the invention contains the sequence for surfactant protein B (SP-B) or for erythropoietin. Further examples of proteins which can be encoded by the "coding region including a start codon at its 5' end coding for a polypeptide" of the DNA molecule according to the invention are growth factors such as human growth hormone hGH, BMP-2 or angiogenesis factors.

Alternatively the nucleic acids may encode full length antibodies or smaller antibodies (e.g., both heavy and light chains) to confer immunity to a subject. In another embodiment, the "coding region including a start codon at its 5' end coding for a polypeptide" may encode a functional monoclonal or polyclonal antibody, which may be useful for targeting and/or inactivating a biological target (e.g., a stimulatory cytokine such as tumor necrosis factor). Similarly, the "coding region including a start codon at its 5' end coding for a polypeptide" may encode, for example, functional anti-nephrotic factor antibodies useful for the treatment of membranoproliferative glomerulonephritis type II or acute hemolytic uremic syndrome, or alternatively may encode anti-vascular endothelial growth factor (VEGF) antibodies useful for the treatment of VEGF-mediated diseases, such as cancer.

Module (a), i.e., the "coding region including a start codon at its 5' end coding for a polypeptide", may be a coding region encoding a polypeptide or a protein which can be used in genome editing technologies. Genome editing is a type of genetic engineering in which DNA is inserted, deleted or replaced in the genome of an organism using nucleases. These nucleases create site-specific double-strand breaks (DSBs) at desired locations in the genome. The induced double-strand breaks are repaired by non-homologous end-joining or homologous recombination, resulting in targeted mutations in the genome, thereby "editing" the genome. Numerous genome editing systems utilizing different polypeptides or proteins are known in the art, i.e., e.g., the CRISPR-Cas system, meganucleases, zinc finger nucleases (ZFNs) and transcription activator-like effector-based nucleases (TALEN). Methods for genome engineering are reviewed in Trends in Biotechnology, 2013, 31 (7), 397-405.

Thus, in a preferred embodiment, the "coding region including a start codon at its 5' end coding for a polypeptide" contains a desoxyribonucleotide sequence which encodes a polypeptide or protein of the Cas (CRISPR associated protein) protein family, preferably Cas9 (CRISPR associated protein 9). Proteins of the Cas protein family, preferably Cas9, may be used in CRISPR/Cas9 based methods and/or CRISPR/Cas9 genome editing technologies. CRISPR-Cas systems for genome editing, regulation and targeting are reviewed in Nat. Biotechnol., 2014, 32(4):347-355.

In another preferred embodiment, the "coding region including a start codon at its 5' end coding for a polypeptide" contains a desoxyribonucleotide sequence which encodes a meganuclease. Meganucleases are endodeoxyribonucleases which, in contrast to "conventional" endodeoxyribonucleases, recognize a large recognition site (e.g., a double-stranded DNA sequence of 12 to 40 base pairs). As a result, the respective site occurs only few times, preferably only once, in any given genome. Meganucleases are therefore considered to be the most specific naturally occurring restriction enzymes and, accordingly, are suitable tools in genome editing technologies.

In another preferred embodiment, the "coding region including a start codon at its 5' end coding for a polypeptide" contains a desoxyribonucleotide sequence which encodes a zinc finger nuclease (ZFN). ZFNs are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of the endogenous DNA repair machinery, ZFNs can be used to precisely alter the genome of higher organisms and are, therefore, suitable tools in genome editing technologies.

In another preferred embodiment, the "coding region including a start codon at its 5' end coding for a polypeptide" contains a desoxyribonucleotide sequence which encodes a transcription activator-like effector nuclease (TALEN). TALENs are restriction enzymes that can be engineered to cut specific sequences of DNA. TALENs are fusion proteins wherein a TAL effector DNA-binding domain is fused to a DNA cleavage domain of a nuclease. Transcription activator-like effectors (TALEs) can be engineered to bind practically any desired DNA sequence. Thus, when combined with a nuclease, DNA can be cut at specific desired locations.

The DNA molecule of the present invention comprises as a second module (b) a sequence which is located directly upstream of the coding sequence.

More specifically, the DNA molecule of the present invention comprises a module (b) directly upstream of said coding sequence, wherein said module (b) is a sequence selected from the group consisting of:

(b1)

$$R_1\text{-CGCCACC;} \quad \text{(SEQ ID NO: 1)}$$

or a sequence wherein in said sequence the C at position 6 of SEQ ID NO:1 is substituted by an A and the C at position 7 of SEQ ID NO:1 is substituted by a G; and/or the A at position 5 of SEQ ID NO:1 is substituted by a G; and (b2) $R_1$-CNGCCACC (SEQ ID NO:2), wherein the nucleotide N at position 2 of SEQ ID NO:2 is a nucleotide selected from the group consisting of T, G, C or A;

or a sequence wherein in said sequence the C at position 7 of SEQ ID NO:2 is substituted by an A and the C at position 8 of SEQ ID NO:2 is substituted by a G; and/or the A at position 6 of SEQ ID NO:2 is substituted by a G, wherein $R_1$ is a promoter which is recognized by a DNA-dependent RNA-polymerase.

The sequences as defined in item (b) herein-above is/are not particularly limited to the above specific sequences but may also relate to (a) sequence(s) which show(s) (a) nucleotide(s) addition(s) in comparison to such sequences, wherein the additional nucleotide(s) may be added at the 5'-end of $R_1$ in the above described sequence(s). The additional nucleotide(s) comprise polynucleotide chains of up to 0 (no changes), 1, 2, 3, 4, 5, 6, 7, 8, 9 or 10 nucleotides, preferably of up to 20 nucleotides. More preferably, 11, 12, 13, 14, 15, 16, 18, or 19 nucleotides are added at the 5'-end. Even more preferably of up to 30 nucleotides are added at the 5'-end.

Since the addition of nucleotides upstream of the promoter $R_1$ will not change the above functional properties of the UTR(s) of the invention the addition of the nucleotides may also have a length of up to 40, 50, 60, 70, 80, 90, or even 100 nucleotides or even more, up to 200, 300, 400 or 500 nucleotides.

As mentioned above, a double-stranded DNA molecule comprises two anti-parallel strands wherein one strand is called the "sense" strand if its sequence is the same as that of a messenger RNA copy that is translated into a protein. The sequence on the opposite, complementary, strand is called the "antisense" sequence. Thus, the DNA molecule of the present invention not only relates to the above DNA molecule which corresponds to an mRNA comprising one strand with the above elements (a) and (b) but also to a DNA molecule comprising the complementary strand, i.e., antisense strand which can be transcribed into mRNA. This complementary strand of the DNA molecule of the present invention is defined by reference to the antisense strand which can easily be determined given the base pairing rules.

The DNA molecule of the present invention also comprises in module (b) a promoter $R_1$ which is recognized by a DNA-dependent RNA-polymerase. Preferably, said promoter $R_1$ is directly linked to the remaining sequence defined in item (b1) or (b2), i.e., without the occurrence of any intervening nucleotides.

The nature of the promoter $R_1$ which is recognized by a DNA-dependent RNA polymerase is not particularly limited. Any promoter (and variants thereof) can be used as long as a corresponding DNA-dependent RNA-polymerase can recognize the respective sequence. Numerous RNA polymerases (also known as DNA-dependent RNA-polymerases and often abbreviated as RNAP or RNApol) are known in the art. These enzymes are capable of producing the primary transcript RNA. As outlined above, DNA-dependent RNA-polymerases are capable of synthesizing RNA chains using DNA as templates in a process called transcription. A DNA-dependent RNA-polymerase initiates transcription at specific DNA sequences known as promoters. It then produces an RNA chain which is complementary to the template DNA strand. The process of adding nucleotides to the RNA strand is known as elongation. Hence, in the context of the present invention, the term "recognizing" preferably not only means that the DNA-dependent RNA-polymerase is capable of specifically detecting/binding its corresponding promoter sequence $R_1$. This term also refers to the DNA-dependent RNA-polymerase's capability to initiate transcription and to then produce an RNA molecule during elongation.

The skilled person can determine by methods known in the art whether a given DNA-dependent RNA-polymerase is capable of recognizing a respective promoter. Moreover, by using well-known methods for the assessment of protein/DNA-interactions, a corresponding (unknown) promoter sequence $R_1$ of a given DNA-dependent RNA-polymerase can be identified and vice-versa.

Thus, the capability of a DNA-dependent RNA-polymerase to recognize/bind its promoter $R_1$ and, preferably, the capability to initiate transcription can be determined by methods known in the art as, e.g., described in Journal of Biological Chemistry, 1993, 268(26):19299-19304 while the discovery of numerous DNA-dependent RNA-polymerases is reviewed in Journal of Biological Chemistry, 2005, 280 (52):42477-42485).

In a preferred embodiment, the promoter $R_1$ which is recognized by a DNA-dependent RNA polymerase is a bacteriophage promoter.

As examples only, it is known in the art that a T7 DNA-dependent RNA polymerase recognizes the sequence TAATACGACTCACTATAGGGAGA (SEQ ID NO: 3), the T3 DNA-dependent RNA polymerase recognizes the sequence AATTAACCCTCACTAAAGGGAGA (SEQ ID NO: 4), the SP6 DNA-dependent RNA polymerase recognizes the sequence ATTTAGGTGACACTATAGAAG (SEQ ID NO: 5) and the K11 DNA-dependent RNA polymerase recognizes the sequence AATTAGGGCACACTATAGGGA (SEQ ID NO: 6). However, these examples are only given for illustration purposes since the present invention is not limited to these promoters and corresponding DNA-dependent RNA polymerases. In fact, any promoter (and variants thereof) can be used as long as a corresponding DNA-dependent RNA-polymerase, preferably bacteriophage DNA-dependent RNA polymerase, can recognize the respective sequence.

In a preferred embodiment, $R_1$ is selected from the group consisting of:
(i) TAATACGACTCACTATAGGGAGA (SEQ ID NO: 3) or a sequence which shows 1 to 6 substitutions in comparison to SEQ ID NO:3 and which is recognized by a T7 DNA-dependent RNA polymerase;
(ii) AATTAACCCTCACTAAAGGGAGA (SEQ ID NO: 4) or a sequence which shows 1 to 6 substitutions in comparison to SEQ ID NO:4 and which is recognized by a T3 DNA-dependent RNA polymerase; ATTTAGGTGACACTATAGAAG (SEQ ID NO: 5) or a sequence which shows
(iii) 1 to 6 substitutions in comparison to SEQ ID NO:5 and which is recognized by a SP6 DNA-dependent RNA polymerase; and
(iv) AATTAGGGCACACTATAGGGA (SEQ ID NO: 6) or a sequence which shows 1 to 6 substitutions in comparison to SEQ ID NO:6 and which is recognized by a K11 DNA-dependent RNA polymerase.

In another preferred embodiment, the sequence may be a sequence which shows 1 to 3, 4 or 5 substitutions as long as the corresponding sequence can still be recognized by the T7, T3, SP6 and K11 DNA-dependent RNA polymerase, respectively. In a more preferred embodiment, the sequence may be a sequence which shows 1 to 2 substitutions as long as the corresponding sequence can still be recognized by the T7, T3, SP6 and K11 DNA-dependent RNA polymerase, respectively. Most preferably, the sequence may be a sequence which shows 1 substitution as long as the corresponding sequence can still be recognized by the T7, T3, SP6 and K11 DNA-dependent RNA polymerase, respectively.

In other embodiments, the promoter sequences $R_1$ which are recognized by a DNA-dependent RNA polymerase are not particularly limited to any of the sequences of SEQ ID NO: 3, SEQ ID NO: 4, SEQ ID NO: 5 or SEQ ID NO: 6 or sequences which show 1 to 6 substitutions in comparison thereto but may also be sequences showing 1 to 7, 8, 9, 10, 11 or 12 substitutions as long as the corresponding sequence can still be recognized by the T7, T3, SP6 and K11 DNA-dependent RNA polymerase, respectively.

In a preferred embodiment, from the above substitution(s) in the sequences of TAATACGACTCACTATAGGGAGA (SEQ ID NO: 3), AATTAACCCTCACTAAAGGGAGA (SEQ ID NO: 4), ATTTAGGTGACACTATAGAAG (SEQ ID NO: 5) or AATTAGGGCACACTATAGGGA (SEQ ID NO: 6), substitutions at the 5 nucleotides "CACTA" at positions 11 to 12 in the above sequences of SEQ ID NOs: 3 to 6 are excluded since these 5 nucleotides are conserved among the four sequences.

In another preferred embodiment, from the above substitution(s) in the sequences of SEQ ID NOs: 3 to 6, a substitution at nucleotide "T" at position 4 in the above sequences of SEQ ID NOs: 3 to 6 is excluded since this nucleotide is conserved among the four sequences.

In another preferred embodiment, from the above substitution(s) in the sequences of SEQ ID NOs: 3 to 6, a substitution at nucleotide "A" at position 5 in the above sequences of SEQ ID NOs: 3 to 6 is excluded since this nucleotide is conserved among the four sequences.

In another preferred embodiment, from the above substitution(s) in the sequences of SEQ ID NOs: 3 to 6, a substitution at nucleotide "G" at position 18 in the above sequences of SEQ ID NOs: 3 to 6 is excluded since this nucleotide is conserved among the four sequences.

The capability of a T7, T3, SP6 and a K11 DNA-dependent RNA-polymerase to recognize/bind its promoter $R_1$ can be determined by methods known in the art as outlined above.

In a more preferred embodiment, the DNA molecule of the present invention is a DNA molecule which comprises a module (b1) directly upstream of said coding sequence, wherein in said module (b1) the nucleotide N at position 2 of SEQ ID NO:2 is a nucleotide selected from the group consisting of T, G or C and wherein nucleotide N is not an A.

In an even more preferred embodiment, said nucleotide N at position 2 of SEQ ID NO:2 is T.

In a preferred embodiment, the DNA molecule of the present invention is a DNA molecule wherein the nucleotide following directly downstream of the start codon is not the nucleotide G. In another preferred embodiment, the DNA molecule of the present invention is a DNA molecule wherein the nucleotide following directly downstream of the start codon is a nucleotide selected from the group consisting of A, T and C.

In an even more preferred embodiment, the DNA molecule of the present invention is a DNA molecule which comprises a module (b1) as defined above, wherein said module (b1) is a sequence wherein the C at position 6 of SEQ ID NO:1 is substituted by an A and the C at position 7 of SEQ ID NO:1 is substituted by a G; and/or the A at position 5 of SEQ ID NO:1 is substituted by a G and wherein the nucleotide following directly downstream of the start codon is a nucleotide selected from the group consisting of A, T and C.

In another even more preferred embodiment, the DNA molecule of the present invention is a DNA molecule which comprises a module (b2) as defined above, wherein said module (b2) is a sequence wherein the C at position 7 of SEQ ID NO:2 is substituted by an A and the C at position 8 of SEQ ID NO:2 is substituted by a G; and/or the A at position 6 of SEQ ID NO:2 is substituted by a G and wherein the nucleotide following directly downstream of the start codon is a nucleotide selected from the group consisting of A, T and C.

In molecular biology and genetics, upstream and downstream both refer to a relative position in a DNA molecule. In the context of the present invention, upstream is toward the 5' end of the sense strand of the DNA molecule and downstream is toward the 3' end of the molecule.

Accordingly, in the present invention, the sequence defined in item (b), above, is located directly upstream of the coding region of item (a), more specifically, directly upstream of the start codon of the coding region. Thus, "directly upstream" in this context means that there is/are no further nucleotides between the sequence as defined in item (b) and the coding sequence which initiates with a start codon. Thus, the coding region which initiates with a start codon is immediately adjacent to the sequence as defined in item (b) herein-above.

The DNA molecules of the present invention may be generated/synthesized recombinantly (e.g., in an in vivo or an in vitro system) or synthetically (e.g., by a PCR reaction or in a chemical reaction) by methods known to the person skilled in the art.

The DNA molecule of the present invention preferably is a recombinant nucleic acid molecule, i.e., it is composed of elements which do not occur in nature in this combination. The nucleic acid molecule of the invention may be synthetic or semi-synthetic.

The DNA molecule may be present in the form of fused DNA sequences of modules (a) and (b) (defined in items (a) and (b), respectively, above) i.e., a (fusion) DNA molecule which is formed by combining at least two nucleotide sequences containing said modules. Typically, as will be explained in more detail further below, this can be accomplished by cloning a cDNA into an expression vector which allows for the transcription into the RNA molecule. Accordingly, the DNA molecule of the present invention may be a fused DNA sequence, i.e., a chimeric molecule which is formed by joining two or more polynucleotides via the phosphate group from one nucleotide bound to the 3' carbon on another nucleotide, forming a phosphodiester bond between the respective ends of one module and the end of another molecule. In this way, DNA molecules containing said at least two modules are joined together in the form of a DNA molecule. Once cloned in frame, such a recombinant DNA molecule may then be transcribed into its corresponding RNA nucleic acid sequence encoding said protein, polypeptide or enzyme molecule.

A DNA molecule according to the present invention may be introduced in a vector, preferably an expression vector, by standard molecular biology techniques (see, e.g. Sambrook et al., Molecular Cloning, A laboratory manual, 2nd Ed, 1989). The term "vector" such as "expression vector" or "cloning vector" in the sense of the present invention is understood as a circular, double-stranded unit of DNA that replicates within a cell independently of the chromosomal DNA and which is used as a vehicle to carry genetic material into a cell, where it can be replicated and/or expressed (i.e., transcribed into RNA and translated into a amino acid sequence). A vector containing foreign DNA is termed recombinant DNA. The vector itself is generally a DNA sequence that typically consists of an insert (e.g., a nucleic acid molecule/DNA molecule of the present invention) and a larger sequence that serves as the "backbone" of the vector. Plasmids in the sense of the present invention are most often found in bacteria and are used in recombinant DNA research to transfer genes between cells and are as such a subpopulation of "vectors" as used in the sense of the present invention.

It is evident to the person skilled in the art that further regulatory sequences may be added to the DNA molecule of the invention. For example, transcriptional enhancers and/or sequences which allow for induced expression may be employed. A suitable inducible system is for example tetracycline-regulated gene expression as described, e.g., by Gossen and Bujard, Proc. Natl. Acad. Sci. USA 89 (1992), 5547-5551) and Gossen, Trends Biotech. 12 (1994), 58-62, or a dexamethasone-inducible gene expression system as described, e.g. by Crook, EMBO J. 8 (1989), 513-519.

The present invention also relates to a vector, preferably an expression vector, comprising the DNA molecule of the present invention.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

The DNA molecule of the present invention preferably also contains poly-A signal ensuring termination of transcription and stabilization of the transcript by addition of a poly-A tail.

The DNA molecules and vectors of the invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention.

The present invention also relates to a host cell comprising the vector of the present invention. Thus, the present invention relates to a host transfected or transformed with the vector of the invention or a non-human host carrying the vector of the present invention, i.e. to a host cell or host which is genetically modified with a DNA molecule according to the invention or with a vector comprising such a DNA molecule. The term "genetically modified" means that the host cell or host comprises in addition to its natural genome a DNA molecule or vector according to the invention which was introduced into the cell or host or into one of its predecessors/parents. The DNA molecule or vector may be present in the genetically modified host cell or host either as an independent molecule outside the genome, preferably as a molecule which is capable of replication, or it may be stably integrated into the genome of the host cell or host. The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The host cell of the present invention may be any prokaryotic or eukaryotic cell. Suitable prokaryotic cells are those generally used for cloning like *E. coli* or *Bacillus subtilis*. Furthermore, eukaryotic cells comprise, for example, fungal or animal cells. Examples for suitable fungal cells are yeast cells, preferably those of the genus *Saccharomyces* and most preferably those of the species *Saccharomyces cerevisiae*. Suitable animal cells are, for instance, insect cells, vertebrate cells, preferably mammalian cells, such as e.g. HEK293, NSO, CHO, COS-7, MDCK, U2-OSHela, NIH3T3, MOLT-4, Jurkat, PC-12, PC-3, IMR, NT2N, Sk-n-sh, CaSki, C33A. Further suitable cell lines known in the art are obtainable from cell line depositories, like, e.g., the Deutsche Sammlung von Mikroorganismen and Zellkulturen GmbH (DSMZ) or the American Type Culture Collection (ATCC). In accordance with the present invention, it is furthermore envisaged that primary cells/cell cultures may function as host cells. Said cells are in particular derived from insects (like insects of the species *Drosophila* or *Blatta*) or mammals (like human, swine, mouse or rat). Said host cells may also comprise cells from and/or derived from cell lines like neuroblastoma cell lines. The above mentioned primary cells are well known in the art and comprise, inter alia, primary astrocytes, (mixed) spinal cultures or hippocampal cultures.

The present invention also relates to a composition comprising the DNA molecule of the present invention, the vector of the present invention or the host cell of the present invention.

In a second aspect, the present invention relates to an RNA molecule comprising
(a) a coding region, including a start codon at its 5' end, coding for a polypeptide; and
(b) directly upstream of said coding sequence a UTR selected from the group consisting of:
(b1) a UTR of the sequence $$R_2\text{-CGCCACC}, \quad \text{(SEQ ID NO: 1)}$$

or a sequence wherein in said UTR sequence the C at position 6 of SEQ ID NO:1 is substituted by an A and the C at position 7 of SEQ ID NO:1 is substituted by a G; and/or the A at position 5 of SEQ ID NO:1 is substituted by a G; and (b2) a UTR of the sequence
$R_2$-CNGCCACC (SEQ ID NO:2), wherein the nucleotide N at position 2 of SEQ ID NO:2 is a nucleotide selected from the group consisting of U, G, C or A, or a sequence wherein in said UTR sequence the C at position 7 of SEQ ID NO:2 is substituted by an A and the C at position 8 of SEQ ID NO:2 is substituted by a G; and/or the A at position 6 of SEQ ID NO:2 is substituted by a G, wherein $R_2$ is an RNA sequence corresponding to the part of a promoter region starting with the nucleotide where a DNA-dependent RNA-polymerase initiates RNA synthesis.

A ribonucleic acid (RNA) molecule as used in accordance with the present invention relates to a polymeric molecule which is assembled as a chain of the nucleotides termed G, A, U, and C. Each nucleotide in RNA contains a ribose sugar, with carbons numbered 1' through 5'. A nitrogenous base is attached to the 1' position, in general, adenine (A), cytosine (C), guanine (G), or uracil (U). In a polymeric RNA molecule a phosphate group is attached to the 3' position of one ribose and the 5' position of the next. Thus, the nucleotides in a polymeric RNA molecule are covalently linked to each other wherein the phosphate group from one nucleotide binds to the 3' carbon on the subsequent nucleotide, thereby forming a phosphodiester bond. Accordingly, an RNA strand has a 5' end and a 3' end, so named for the carbons on the ribose ring. By convention, upstream and downstream relate to the 5' to 3' direction in which RNA transcription takes place. Preferably, the RNA molecule is a messenger RNA (mRNA) molecule. mRNA is a large family of RNA molecules that convey genetic information from DNA to the ribosome, where they specify the amino acid sequence of the protein products of gene expression. Following transcription of primary transcript mRNA (known as pre-mRNA) by RNA polymerase, processed, mature mRNA is translated into a polymer of amino acids: a protein, as summarized in the central dogma of molecular biology. As in DNA, mRNA genetic information is in the sequence of nucleotides, which are arranged into codons consisting of three bases each.

Each codon encodes for a specific amino acid, except the stop codons, which terminate protein synthesis.

RNA molecule of present invention comprises two main modules as defined in items (a) and (b), above. In addition, the RNA molecule of present invention preferably comprises a UTR at its 3' end. Thus, the RNA molecule of the present invention resembles with respect to its structure a "normal" mRNA molecule which occurs in nature, harbouring a coding region as well as (5' and 3') untranslated regions (UTRs) and, optionally, a poly-A tail.

The term "coding region including a start codon at its 5' end" as used in accordance with the present invention relates to a sequence which is composed of codons, which are decoded and translated into protein by the ribosome in accordance with the information provided by the genetic code. Coding regions commonly begin with a start codon at their 5' end and end with a stop codon. In general, the start codon is an AUG triplet and the stop codon is UAA, UAG, or UGA. In addition to being protein-coding, portions of coding regions may serve as regulatory sequences in the pre-mRNA as exonic splicing enhancers or exonic splicing silencers. The coding region of a gene coding for a polypeptide or a protein as used in accordance with the present invention is also known as the coding sequence or CDS (from coding DNA sequence) and is that portion of a gene's DNA or RNA, composed of exons, that codes for a polypeptide or protein. The coding region in mRNA is flanked by the 5'-untranslated region (5' UTR) and the 3'-untranslated region (3' UTR) which are also parts of the exons. Moreover, mRNA molecules may further comprise a so-called 5' cap and a poly-A tail. The 5' cap, the 5' UTR, the 3' UTR and the poly-A tail are regions of an mRNA molecule which are not translated into protein.

The term "untranslated region" or "UTR" as used in accordance with the present invention relates to sections of the mRNA upstream of the start codon and downstream of the stop codon that are not translated, and are, therefore, termed the five prime untranslated region (5' UTR) and three prime untranslated region (3' UTR), respectively. These regions are transcribed with the coding region and thus are exonic as they are present in the mature mRNA.

As used in the present invention, the 3' untranslated region (3'-UTR) relates to the section of messenger RNA (mRNA) that immediately follows the translation termination codon. The 3' UTR may comprise regulatory regions within the 3'-untranslated region which are known to influence polyadenylation and stability of the mRNA. Many 3'-UTRs also contain AU-rich elements (AREs). Furthermore, the 3'-UTR may preferably contain the sequence AAUAAA that directs addition of several hundred adenine residues called the poly(A) tail to the end of the mRNA transcript.

As used in the present invention, the 5' untranslated region (5' UTR) (also known as a Leader Sequence or Leader RNA) is the region of an mRNA that is directly upstream of the start codon. The 5' UTR begins at the transcription start site and ends one nucleotide (nt) before the start codon (usually AUG) of the coding region. In eukaryotes the length of the 5' UTR is generally from 100 to several thousand nucleotides long but sometimes also shorter UTRs occur in eukaryotes.

In the present invention, the 5' UTR is extremely short since it is an object of the present invention to provide a minimal UTR sequence.

An RNA molecule of the present invention may also contain a poly-A tail. A poly-A tail is a long sequence of adenine nucleotides (often several hundred) added to the 3' end of the pre-mRNA by a process called polyadenylation. This tail promotes export from the nucleus and translation, and protects the mRNA from degradation. Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation.

One module of the RNA molecule, i.e., "a coding region including a start codon at its 5' end coding for a polypeptide" (module (a)) is not particularly limited and may be any desired coding region which is to be expressed in a given cell. As regards the preferred embodiments of the term "a coding region including a start codon at its 5' end coding for a polypeptide" (module (a)) the same applies, mutatis mutandis, to the RNA molecule of the present invention as has been set forth above in the context of the DNA molecule of the present invention.

The RNA molecule of the present invention comprises a module (b) directly upstream of said coding sequence, wherein said module (b) is a UTR selected from the group consisting of:

(b1) a UTR of the sequence $$R_2\text{-CGCCACC,} \quad \text{(SEQ ID NO: 1)}$$

or a sequence wherein in said UTR sequence the C at position 6 of SEQ ID NO:1 is substituted by an A and the C at position 7 of SEQ ID NO:1 is substituted by a G; and/or the A at position 5 of SEQ ID NO:1 is substituted by a G; and (b2) a UTR of the sequence $R_2$-CNGCCACC (SEQ ID NO:2), wherein the nucleotide N at position 2 of SEQ ID NO:2 is a nucleotide selected from the group consisting of U, G, C or A, or a sequence wherein in said UTR sequence the C at position 7 of SEQ ID NO:2 is substituted by an A and the C at position 8 of SEQ ID NO:2 is substituted by a G; and/or the A at position 6 of SEQ ID NO:2 is substituted by a G, wherein $R_2$ is an RNA sequence corresponding to the part of a promoter region starting with the nucleotide where a DNA-dependent RNA-polymerase initiates RNA synthesis.

The nature of $R_2$ is not particularly limited. Any RNA sequence which corresponds to the part of a promoter region starting with the nucleotide where a DNA-dependent RNA-polymerase initiates RNA synthesis can be used. The skilled person is easily in a position to determine those parts of a promoter region starting with the nucleotide from which a DNA-dependent RNA-polymerase initiates RNA synthesis. This RNA sequence $R_2$ is the sequence of a promoter which corresponds to the part of a promoter which is transcribed, i.e., which is actually present in the transcript once transcribed.

In a preferred embodiment, the promoter $R_2$ is an RNA sequence corresponding to the part of a promoter region starting with the nucleotide where a bacteriophage derived DNA-dependent RNA-polymerase initiates RNA synthesis.

In a preferred embodiment, the promoter $R_2$ is an RNA sequence corresponding to the part of a promoter region starting with the nucleotide where a T7 DNA-dependent RNA polymerase, T3 DNA-dependent RNA polymerase, SP6 DNA-dependent RNA polymerase or a K11 DNA-dependent RNA polymerase initiates RNA synthesis.

In order to illustrate this, as non-limiting examples, $R_2$ is the underlined sequence in the following promoter sequences of TAATACGACTCACTATAGGGAGA (SEQ ID NO: 3; i.e., the promoter recognized by the T7 DNA-dependent RNA polymerase), AATTAACCCT-CACTAAAGGGAGA (SEQ ID NO: 4; i.e., the promoter recognized by the T3 DNA-dependent RNA polymerase), ATTTAGGTGACACTATAGAAG (SEQ ID NO: 5; i.e., the promoter recognized by the SP6 DNA-dependent RNA polymerase) and AATTAGGGCACACTATAGGGA (SEQ ID NO: 6; i.e., the promoter recognized by the K11 DNA-dependent RNA polymerase). The underlined sequences correspond to the part of the respective promoter where a DNA-dependent RNA-polymerase initiates RNA synthesis and, accordingly, which is actually present in the RNA molecule (i.e., in the transcript) once transcribed.

The UTR sequence(s) having any of the above substitutions in comparison to a UTR of the sequence $R_2$-CGCCACC (SEQ ID NO:1) or in comparison to a UTR of the sequence $R_2$-CNGCCACC (SEQ ID NO:2) may result in an RNA molecule showing the same or a similar, preferably a higher translation efficiency as an RNA molecule comprising a UTR of the sequence $R_2$-CGCCACC (SEQ ID NO:1) and an RNA molecule comprising a UTR of the sequence $R_2$-CNGCCACC (SEQ ID NO:2), respectively. The translation efficiency of a given RNA molecule comprising a UTR as described herein can be determined by the skilled person by methods known in the art and as described in the following.

The translation efficiency is the rate of mRNA translation into polypeptides or proteins within cells. The translation efficiency of a given mRNA is measured as the number of proteins or polypeptides which are translated per mRNA per time unit. Translation is the process in which cellular ribosomes create proteins and is well-known to the skilled person. Briefly, in translation, messenger RNA (mRNA) which is produced by transcription from DNA is decoded by a ribosome to produce a specific amino acid chain or a polypeptide or a protein.

Thus, the translation efficiency of a given RNA molecule harbouring a modified UTR sequence with any of the above substitutions is preferably the same or higher in comparison to the translation efficiency of the same given RNA but harbouring an UTR of $R_2$-CGCCACC (SEQ ID NO:1) or $R_2$-CNGCCACC (SEQ ID NO:2) as defined herein above, respectively. Accordingly, the number of proteins or polypeptides encoded by the coding region of the RNA molecule harbouring a modified UTR sequence with any of the above substitutions which are translated per RNA per time unit is at least the same or is, preferably, higher than the number of proteins or polypeptides encoded by the coding region of the RNA molecule harbouring an UTR of $R_2$-CGCCACC (SEQ ID NO:1) or $R_2$-CNGCCACC (SEQ ID NO:2) as defined herein above, respectively, which are translated per RNA per time unit.

Translation efficiency, in the context of the present invention, is preferably the rate of mRNA translated into protein within a cell at a certain time point in relation to the amount of mRNA encoding the respective protein in said cell at the same time point. Thus, the translation efficiency is the quotient of the mRNA translated into protein within a cell at a certain time point and the amount of mRNA encoding the respective protein. Both parameters, i.e., the mRNA translated into a protein as well as the amount of mRNA encoding the respective protein, can be determined by methods known in the art. As non-limiting examples, the amount of mRNA translated into protein within a cell can, e.g., be determined by as determined by flow cytometry (FC) while the amount of mRNA encoding the respective protein can, e.g., be measured by qPCR.

The UTR(s) as defined in item (b) herein-above is/are not particularly limited to the above specific sequences but may also relate to (a) UTR sequence(s) which comprise(s) a sequence which shows (a) nucleotide(s) addition(s) in comparison to such sequences, wherein the additional nucleotide(s) may be added at the 5'-end of the above described UTR(s). The additional nucleotide(s) comprise polynucleotide chains of up to 0 (no changes), 1, 2, 3, 4, 5, 6, 7, 8, 9 or 10 nucleotides, preferably of up to 20 nucleotides. More preferably, 11, 12, 13, 14, 15, 16, 18, or 19 nucleotides are added at the 5'-end. Even more preferably of up to 30 nucleotides are added at the 5'-end.

In light of the rationale that the addition of nucleotides is likely not to change the above functional properties of the respective UTR(s) the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as the UTRs defined in item (b) herein-above.

In a preferred embodiment, the UTR as defined in item (b1) herein-above has a maximal length of 11, 12 or 13 nucleotides. Preferably, the UTR as defined in item (b1) herein-above has a maximal length of 13 nucleotides if $R_2$ is GGGAGA (SEQ ID NO: 7) or GGGAGA (SEQ ID NO: 8).

Preferably, the UTR as defined in item (b1) herein-above has a maximal length of 11 nucleotides if $R_2$ is GAAG (SEQ ID NO: 9) or GGGA (SEQ ID NO: 10).

In another preferred embodiment, the UTR as defined in item (b2) herein-above has a maximal length of 12, 13 or 14 nucleotides. Preferably, the UTR as defined in item (b2) herein-above has a maximal length of 14 nucleotides if $R_2$ is GGGAGA (SEQ ID NO: 7) or GGGAGA (SEQ ID NO: 8).

Preferably, the UTR as defined in item (b2) herein-above has a maximal length of 12 nucleotides if $R_2$ is GAAG (SEQ ID NO: 9) or GGGA (SEQ ID NO: 10).

The RNA molecules of the present invention containing the above-described UTR(s) may be generated/synthesized recombinantly (e.g., in an in vivo or an in vitro system) or synthetically by methods known to the person skilled in the art.

In vitro transcription of RNA usually requires a linear DNA template containing a double-stranded promoter region where the DNA-dependent RNA-polymerase binds and initiates RNA synthesis while the coding region may be double-stranded or single-stranded. In case the linear DNA template contains a single-stranded coding region, the anti-sense strand (i.e., the strand which is read by the DNA-dependent polymerase) of the coding region is part of the template. Common DNA-dependent RNA-polymerases are the T7 polymerase, the T3 polymerase, SP6 polymerase and the K11 polymerase. The full sequence of their respective promoters is shown in SEQ ID NOs: 3 to 6.

Transcription templates for an in vitro transcription include, for example, cDNA templates synthesized from an RNA precursor, templates generated by PCR, chemically synthesized oligonucleotides and plasmid constructs. Many widely used plasmid cloning vectors harbour phage polymerase promoters located on each side of the multiple cloning site to allow transcription of either strand of a nucleotide sequence inserted into the multiple cloning site. Commonly used cloning vectors include for example Invitrogen's pCRII, Promega's pGEM and Stratagene's pBluescript vectors. Ambion's pTRIPLEscript family of vectors contain all three phage polymerase promoters in tandem (on the same side of the multiple cloning site), allowing any of the three polymerases, SP6, T7 or T3 to be used.

The RNA molecules of the present invention may be produced recombinantly in in vivo systems by methods known to the person skilled in the art.

Alternatively, the RNA molecules of the present invention may be produced in an in vitro system using, for example, an in vitro transcription system. In vitro transcription systems are commonly known and usually require a purified linear DNA template containing a DNA sequence "encoding" the RNA molecule wherein said DNA sequence is under the control of an appropriate promoter. Moreover, an in vitro transcription system also commonly requires ribonucleoside triphosphates, a buffer system that includes DTT and magnesium ions, and an appropriate RNA polymerase which provides the enzymatic activity for the in vitro transcription of the DNA sequence into a corresponding RNA molecule of the present invention.

Furthermore, the RNA molecules may be chemically synthesized, e.g., by conventional chemical synthesis on an automated nucleotide sequence synthesizer using a solid-phase support and standard techniques or by chemical synthesis of the respective DNA-sequences and subsequent in vitro or in vivo transcription of the same.

In accordance with the above, the present invention provides RNA molecules/polyribonucleic acid molecules, preferably modified polyribonucleic acid molecules, wherein one module of said RNA molecule, i.e., "a coding region including a start codon at its 5' end" (module (a)), encodes for a polypeptide. The terms nucleic acid and polynucleotide are used interchangeably and include any compound and/or substance that comprises a polymer of nucleotides. The term nucleotide includes deoxynucleotides and ribonucleotides. The terms ribonucleic acid and polyribonucleotide are used interchangeably and, in certain embodiments, include any compound and/or substance that comprises a polymer of nucleotides wherein greater than 50% of the nucleotides are ribonucleotides. In certain embodiments, polyribonucleotides comprise a polymer of nucleotides wherein greater than 60%, 70%, 75%, 80%, 90%, greater than 95%, greater than 99% or 100% of the nucleotides are ribonucleotides. Polyribonucleotides wherein one or more nucleotides are modified nucleotides may be referred to as modified polyribonucleotides. However, the term polyribonucleotides may include modified polyribonucleotides.

The sequence of the RNA molecules/polyribonucleotides can be derived from, for example, any suitable nucleic acid that comprises the genetic information of a gene of interest. Examples of nucleic acids include genomic DNA, RNA, or cDNA from any bacterial or archaeal cell comprising the gene(s) of interest. The polynucleotides can be derived from nucleic acids carrying mutated genes and polymorphisms. An RNA molecule/polyribonucleotide of the present invention comprises a sequence which is not particularly limited and may comprise, as module A, any desired coding region which is expressed in a given cell. In a preferred embodiment, said sequence may be a coding region coding for a desired polypeptide/protein as outlined above. Preferably, in line with the above, the RNA molecule/polyribonucleotide further comprises an untranslated sequence positioned upstream (5') of the module A's start codon, an untranslated sequence positioned downstream (3') of module A's stop codon, or both an untranslated sequence positioned upstream (5') of module A's start codon and an untranslated sequence positioned downstream (3') of module A's stop codon. In a preferred embodiment, an RNA molecule/polyribonucleotide of the present invention may be a modified RNA molecule/polyribonucleotide.

In addition to the four classical ribonucleotides, namely, adenosine, guanosine, cytidine and uridine, there exist numerous analogs of each of these nucleobases. Sometimes throughout and in the literature, these analogs, or RNA molecules/polyribonucleotides that include one or more of these analogs, are referred to as modified (e.g., modified nucleotides or modified ribonucleotides). Some analogs differ from the above canonical nucleobases, but yet can exist in nature. Other analogs are non-naturally occurring. Either type of analog is contemplated.

In certain embodiments, RNA molecules/polyribonucleotides of the present invention comprise nucleotide analogs (e.g., the polyribonucleotide comprises a modified polyribonucleotide). Exemplary nucleotide analogs are provided below (e.g., analogs of U; analogs of C; analogs of A; analogs of G). In addition, in certain embodiments, an RNA molecule/polyribonucleotide or other nucleic acid of the disclosure may also comprise (in addition to or alternatively) modifications in the phosphodiester backbone or in the linkage between nucleobases. Exemplary nucleic acids that can form part or all of an RNA molecule/polyribonucleotide of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a beta-D-ribo configuration, alpha-LNA having an alpha-L-ribo configuration (a diastereomer of LNA), 2'-amino-LNA having a 2'-amino functionalization, and 2'-amino-alpha-LNA having a 2'-amino functionalization) or hybrids thereof.

In certain embodiments, a modification may be on one or more nucleoside(s) or the backbone of the nucleic acid/polynucleotide molecule. In certain embodiments, a modification may be on both a nucleoside and a backbone linkage. In certain embodiments, a modification may be engineered into a polynucleotide in vitro. In certain embodiments, a modified ribonucleotide/nucleotide may also be synthesized post-transcriptionally by covalent modification of the classical/natural ribonucleotides/nucleotides.

An RNA molecule/polyribonucleotide of the present invention can be a modified RNA molecule/polyribonucleotide and, in certain embodiments, can comprise analogs of purines and/or analogs of pyrimidines. In certain embodiments, a modified RNA molecule/polyribonucleotide of the present invention comprises a pyrimidine analog, such as an analog of uridine and/or an analog of cytidine. In certain embodiments, a modified RNA molecule/polyribonucleotide of the present invention comprises an analog of uridine and an analog of cytidine. In certain embodiments, the modified RNA molecule/polyribonucleotide does not comprise analogs of adenosine and/or analogs of guanosine. In certain embodiments, the RNA molecule/polyribonucleotide comprises a single type of analog of uridine and a single type of analog of cytidine (e.g., one type of analog, not a single molecule of analog—the single analog may be present at any of several percentages described herein). In other embodiments, the RNA molecule/polyribonucleotide comprises more than one type of analog of uridine and/or cytidine and, optionally and if present, one or more analogs of adenosine and/or guanosine (or none of either or both).

In some cases a modified uridine (e.g., analog of uridine) is selected from 2-thiouridine, 5'-methyluridine, pseudouridine, 5-iodouridine (I5U), 4-thiouridine (S4U), 5-bromouridine (Br5U), 2'-methyl-2'-deoxyuridine (U2'm), 2'-amino-2'-deoxyuridine (U2'NH$_2$), 2'-azido-2'-deoxyuridine (U2'N$_3$), and 2'-fluoro-2'-deoxyuridine (U2'F). In some cases, a modified cytidine (e.g., analog of cytidine) is selected from 5-methylcytidine, 3-methylcytidine, 2-thiocytidine, 2'-methyl-2'-deoxycytidine (C2'm), 2'-amino-2'-deoxycytidine (C2'NH2), 2'-fluoro-2'-deoxycytidine (C2'F), 5-iodocytidine (I5C), 5-bromocytidine (Br5C) and 2'-azido-2'-deoxycytidine (C2'N3). Note that when referring to analogs, the foregoing also refers to analogs in their 5' triphosphate form. In certain embodiments, the cytidine analog is 5-iodocytidine and the uridine analog is 5-iodouridine.

In some embodiments, the RNA molecule/polyribonucleotide is a modified RNA molecule/polyribonucleotide. In some cases, the modified RNA molecule/polyribonucleotide is at least 25% more stable as compared to a non-modified (or unmodified) RNA molecule/polyribonucleotide. In some cases, the modified RNA molecule/polyribonucleotide can be at least 30% more stable, at least 35% more stable, at least 40% more stable, at least 45% more stable, at least 50% more stable, at least 55% more stable, at least 60% more stable, at least 65% more stable, at least 70% more stable, at least 75% more stable, at least 80% more stable, at least 85% more stable, at least 90% more stable, or at least 95% more stable as compared to a non-modified RNA molecule/polyribonucleotide. In certain embodiments, stability is measured in vivo. In certain embodiments, stability is measured in vitro. In certain embodiments, stability is quantified by measuring the half-life of the polyribonucleotide.

A RNA molecule/polyribonucleotide of the present invention can have nucleotides that have been modified in the same form or else a mixture of different modified nucleotides. The modified nucleotides can have modifications that are naturally or not naturally occurring in messenger RNA. A mixture of various modified nucleotides can be used. For example one or more modified nucleotides within an RNA molecule/polyribonucleotide can have natural modifications, while another part has modifications that are not naturally found in mRNA. Additionally, some modified nucleotides can have a base modification, while other modified nucleotides have a sugar modification. In the same way, it is possible that all modifications are base modifications or all modifications are sugar modifications or any suitable mixture thereof. In some cases, the stability of the modified RNA molecule/polyribonucleotide can be selectively optimized by changing the nature of modified bases within the modified polyribonucleotide.

TABLE 2

Non-limiting examples of analogs of U

| Name | Base modification (5'-position) | Sugar modification (2'-position) | Naturally in mRNA |
|---|---|---|---|
| 5-methyluridine (m5U) | CH$_3$ | — | No |
| 5-iodouridine (I5U) | I | — | No |
| 5-bromouridine (Br5U) | Br | — | No |
| 2-thiouridine (S2U) | S (in 2 position) | — | No |
| 4-thiouridine (S4U) | S (in 4 position) | — | No |
| 2'-methyl-2'-deoxyuridine (U2'm) | — | CH$_3$ | Yes |
| 2'-amino-2'-deoxyuridine (U2'NH2) | — | NH$_2$ | No |
| 2'-azido-2'-deoxyuridine (U2'N3) | — | N$_3$ | No |

TABLE 2-continued

Non-limiting examples of analogs of U

| Name | Base modification (5'-position) | Sugar modification (2'-position) | Naturally in mRNA |
|---|---|---|---|
| 2'-fluoro-2'-deoxyuridine (U2'F) | — | F | No |

TABLE 3

Non-limiting examples of analogs of C

| Name | Base modification (5'-position) | Sugar modification (2'-position) | Naturally in mRNA |
|---|---|---|---|
| 5-methylcytidine (m5C) | CH$_3$ | — | Yes |
| 5-iodocytidine (I5C) | I | — | No |
| 5-bromocytidine (Br5C) | Br | — | No |
| 2-thiocytidine (S2C) | S (in 2 position) | — | No |
| 2'-methyl-2'-deoxycytidine (C2'm) | — | CH$_3$ | Yes |
| 2'-amino-2'-deoxycytidine (C2'NH2) | — | NH$_2$ | No |
| 2'-azido-2'-deoxycytidine (C2'N3) | — | N$_3$ | No |
| 2'-fluoro-2'-deoxycytidine (C2'F) | — | F | No |

TABLE 4

Non-limiting examples of analogs of A

| Name | Base modification (5'-position) | Sugar modification (2'-position) | Naturally in mRNA |
|---|---|---|---|
| N6-methyladenosine (m6A) | CH$_3$ (in 6 position) | — | Yes |
| N1-methyladenosine (m1A) | CH$_3$ (in 1 position) | — | No |
| 2'-0-methyladenosine (A2'm) | — | CH$_3$ | Yes |
| 2'-amino-2'-deoxyadenosine (A2'NH2) | — | NH$_2$ | No |
| 2'-azido-2'-deoxyadenosine (A2'N3) | — | N$_3$ | No |
| 2'-fluoro-2'-deoxyadenosine (A2'F) | — | F | No |

TABLE 5

Non-limiting examples of analogs of G

| Name | Base modification (5'-position) | Sugar modification (2'-position) | Naturally in mRNA |
|---|---|---|---|
| N1-methylguanosine (m1G) | CH$_3$ (in position 1) | — | No |
| 2'-0-methylguanosine (G2'm) | — | CH$_3$ | Yes |
| 2'-amino-3'-deoxyguanosine (G2'NH2) | — | NH$_2$ | No |
| 2'-azido-2'-deoxyguanosine (G2'N3) | — | N$_3$ | No |
| 2'-fluoro-2'-deoxyguanosine (G2'F) | — | F | No |

In certain embodiments, an analog (e.g., a modified nucleotide) can be selected from the group comprising pyridin-4-one ribonucleoside, 5-iodouridine, 5-iodocytidine, 5-aza-uridine, 2'-amino-2'-deoxycytidine, 2'-fluor-2'-deoxycytidine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, 5-methylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In certain embodiments, a modified RNA molecule/polyribonucleotide of the present invention does not include pseudouridine. In certain embodiments, a modified RNA molecule/polyribonucleotide of the present invention does not include 5-methyl cytidine. In certain embodiments, a modified RNA molecule/polyribonucleotide of the present invention does not include 5-methyl uridine. In certain embodiments, a modified RNA molecule/polyribonucleotide of the present invention comprises analogs of U and analogs of C, wherein such analogs of U may all be the same analog or may be different analogs (e.g., more than one type of analog), and wherein such analogs of C may all be the same analog or may be different analogs (e.g., more than one type of analog). In certain embodiments, a modified RNA molecule/polyribonucleotide of the present invention does not include analogs of adenosine and analogs of guanosine.

As described in detail herein, when an RNA molecule/polyribonucleotide comprises a modified polyribonucleotide, analogs may be present as a certain proportion of the nucleotides in the compound (e.g., a given percentage of a given nucleobase may be analog, as described herein).

An RNA molecule/polyribonucleotide that comprises at least one modified nucleotide is a modified RNA molecule/polyribonucleotide. In certain embodiments, at least about 5% of the modified RNA molecule/polyribonucleotide includes modified or non-naturally occurring (e.g., analogs of or modified) adenosine, cytidine, guanosine, or uridine, such as the analog nucleotides described herein. In some cases, at least about 5%, 10%, 15%, 20%, 25%, 30%, 40%, 45%, 50% of the modified RNA molecule/polyribonucleotide includes modified or non-naturally occurring (e.g., analogs of or modified) adenosine, cytidine, guanosine, or uridine. In some cases, at most about 50%, 45%, 40%, 35%, 30%, 25%, 20%, 15%, 10%, 5% of the modified RNA molecule/polyribonucleotide includes modified or non-naturally occurring adenosine, cytidine, guanosine, or uridine.

In a preferred embodiment the RNA molecule of the present invention contains a combination of modified and unmodified nucleotides. Preferably, the RNA molecule of the present invention contains a combination of modified and unmodified nucleotides as described in WO 2011/012316. Such RNA molecules are also known and commercialized as "SNIM®-RNA". The RNA molecule described in WO 2011/012316 is reported to show an increased stability and diminished immunogenicity. In a preferred embodiment, in such a modified RNA molecule 5 to 50% of the cytidine nucleotides and 5 to 50% of the uridine nucleotides are modified. The adenosine- and guanosine-containing nucleotides can be unmodified. The adenosine and guanosine nucleotides can be unmodified or partially modified, and they are preferably present in unmodified form. Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties. It is particularly preferred that the modified cytidine nucleotides are 5-methylcytidine residues and the modified uridine nucleotides are 2-thiouridine residues. Most preferably, the content of modified cytidine nucleotides and the content of the modified uridine nucleotides is 25%, respectively.

In certain other embodiments, in such a modified RNA molecule/polyribonucleotide molecule, 5 to 50% of the cytidines are analogs of C and 5 to 50% of the uridines are analogs of U. In certain embodiments, in such a modified polyribonucleotide molecule 5 to 40% of the cytidines are analogs of C and 5 to 40% of the uridines are analogs of U. In certain embodiments, in such a modified RNA molecule/polyribonucleotide molecule 5 to 30% of the cytidines are analogs of C and 5 to 30% of the uridines are analogs of U. In certain embodiments, in such a modified RNA molecule/polyribonucleotide molecule 10 to 30% of the cytidines are analogs of C and 10 to 30% of the uridines are analogs of U. In certain embodiments, in such a modified polyribonucleotide molecule 5 to 20% of the cytidines are analogs of C and 5 to 20% of the uridines are analogs of U. In certain embodiments, in such a modified RNA molecule/polyribonucleotide molecule 5 to 10% of the cytidine nucleotides and 5 to 10% of the uridine nucleotides are modified. In certain embodiments, in such a modified RNA molecule/polyribonucleotide molecule 25% of the cytidine nucleotides and 25% of the uridine nucleotides are modified. In certain embodiments, the adenosine- and guanosine-containing nucleotides can be unmodified. In certain embodiments, the adenosine and guanosine nucleotides can be unmodified or partially modified, and they are preferably present in unmodified form.

As noted above, in certain embodiments, analogs of U refers to a single type of analog of U. In certain embodiments, analogs of U refers to two or more types of analogs of U. In certain embodiments, analogs of C refers to a single type of analog of C. In certain embodiments, analogs of C refers to two or more types of analogs of C.

In certain embodiments, the percentage of cytidines in an RNA molecule/polyribonucleotide that are analogs of cytidine is not the same as the percentage of uridines in the RNA molecule/polyribonucleotide that are analogs of uridine. In certain embodiments, the percentage of analogs of cytidine is lower than the percentage of analogs of uridine. As noted above, this may be in the presence or the absence of analogs of adenosine and guanosine but, in certain embodiments, is in the absence of analogs of adenosine and analogs of guanosine. In certain embodiments, polyribonucleotides of the disclosure comprises less than 15%, less than 10%, less than 5% or less than 2% analogs of adenosine, analogs of guanosine or both.

In certain embodiments, an RNA molecule/polyribonucleotide of the present invention comprises analogs of cytidine and analogs of uridine, and 5 to 20% of the cytidines are analogs of cytidine and 25 to 45% of the uridines are analogs of uridine. In other words, the RNA molecule/polyribonucleotide comprises modified and unmodified cytidines and modified and unmodified uridines, and 5 to 20% of the cytidines comprise analogs of cytidine while 25 to 45% of the uridines comprise analogs of uridine. In other embodiments, the RNA molecule/polyribonucleotide comprises 5 to 10% analogs of cytidine and 30 to 40% analogs of uridine, such as 7-9% analogs of cytidine, such as about 7, 7.5 or 8% and, such as 32-38% analogs of uridine, such as about 33, 34, 35, 36%.

In certain embodiments, any of the analogs of uridine and analogs of cytidine described herein may be used, optionally excluding pseudouridine. In certain embodiments, the analog of cytidine comprises or consists of (e.g., in the case of consists of, it is the single analog type used) 5-iodocytidine and the analog of uridine comprises or consists of (e.g., in the case of consists of, it is the single analog type used) 5-iodouridine.

In certain embodiments of any of the foregoing, the percentage of analogs of a given nucleotide refers to input percentage (e.g., the percentage of analogs in a starting reaction, such as a starting in vitro transcription reaction). In certain embodiments of any of the foregoing, the percentage of analogs of a given nucleotide refers to output (e.g., the percentage in a synthesized or transcribed compound).

The RNA molecules/polyribonucleotide molecules of the present invention may be produced recombinantly in in vivo systems by methods known to a person skilled in the art which are described in more detail further below.

Alternatively, the modified polyribonucleotide molecules of the present invention may be produced in an in vitro system using, for example, an in vitro transcription system which is described in more detail further below. An in vitro transcription system capable of producing RNA molecules/polyribonucleotides requires an input mixture of modified and unmodified nucleoside triphosphates to produce modified RNA molecules/polyribonucleotides with the desired properties of the present invention. In certain embodiments, 5 to 50% of the cytidines are analogs of cytidine in such an input mixture and 5 to 50% of the uridines are analogs of uridine in such an input mixture. In certain embodiments, 5 to 40% of the cytidines are analogs of cytidine in such an input mixture and 5 to 40% of the uridines are analogs of uridine in such an input mixture. In certain embodiments, 5 to 30% of the cytidines are analogs of cytidine in such a mixture and 5 to 30% of the uridines are analogs of uridine in such an input mixture. In certain embodiments, 5 to 30% of the cytidines are analogs of cytidine in such mixture and 10 to 30% of the uridines are analogs of uridine in such mixture. In certain embodiments, 5 to 20% of the cytidines are analogs of cytidine in such an input mixture and 5 to 20% of the uridines are analogs of uridine in such an input mixture. In certain embodiments, 5 to 10% of the cytidines are analogs of cytidine in such an input mixture and 5 to 10% of the uridines are analogs of uridine in such an input mixture. In certain embodiments, 25% of the cytidines are analogs of cytidine in such an input mixture and 25% of the uridines are analogs of uridine in such an input mixture. In certain embodiments, the input mixture does not comprise analogs of adenosine and/or guanosine. In other embodiments, optionally, the input mixture comprises one or more analogs of adenosine and/or guanosine (or none of either or both).

In certain embodiments, the percentage of cytidines in an input mixture that are analogs of cytidine is not the same as the percentage of uridines in an input mixture that are analogs of uridine. In certain embodiments, the percentage of analogs of cytidine in an input mixture is lower than the percentage of analogs of uridine in an input mixture. As noted above, this may be in the presence or the absence of analogs of adenosine and guanosine in the input mixture but, in certain embodiments, is in the absence of analogs of adenosine and analogs of guanosine in the input mixture.

In certain embodiments, an input mixture of nucleotides for an in vitro transcription system that produces a RNA molecule/polyribonucleotide of the present invention comprises analogs of cytidine and analogs of uridine, and 5 to 20% of the cytidines of the input mixture are analogs of cytidine and 25 to 45% of the uridines of the input mixture are analogs of uridine. In other words, the input mixture comprises modified and unmodified cytidines and modified and unmodified uridines, and 5 to 20% of the cytidines of the input mixture comprise analogs of cytidine while 25 to 45% of the uridines of the input mixture comprise analogs of uridine. In other embodiments, the input mixture comprises 5 to 10% analogs of cytidine and 30 to 40% analogs of uridine, such as 7-9% analogs of cytidine, such as 7, 7.5 or 8% and, such as 32-38% analogs of uridine, such as 33, 34, 35, 36%.

In certain embodiments, any of the analogs of uridine and analogs of cytidine described herein may be used, optionally excluding pseudouridine. In certain embodiments, the analog of cytidine comprises or consists of (e.g., it is the single C analog type used) 5-iodocytidine and the analog of uridine comprises or consists of (e.g., it is the single U analog type used) 5-iodouridine.

Exemplary analogs are described in the tables above. It should be understood that for modified polyribonucleotides encoding the desired polypeptide (module (a)), the analogs and level of modification is, unless indicated otherwise, considered across the entire polyribonucleotide encoding the desired polypeptide (module (a)), including 5' and 3' untranslated regions (e.g., the level of modification is based on input ratios of analogs in an in vitro transcription reaction such that analogs may be incorporated at positions that are transcribed).

Furthermore, the modified RNA molecules/polyribonucleotide molecules may be chemically synthesized, e.g., by conventional chemical synthesis on an automated nucleotide sequence synthesizer using a solid-phase support and standard techniques or by chemical synthesis of the respective DNA sequences and subsequent in vitro or in vivo transcription of the same.

In molecular biology and genetics, upstream and downstream both refer to a relative position in an RNA molecule. In the context of the present invention, upstream is toward the 5' end of the RNA molecule and downstream is toward the 3' end of the molecule.

Accordingly, in the present invention, the UTR defined in item (b), above, is located directly upstream of the coding region of item (a), more specifically, directly upstream of the start codon of the coding region. Thus, "directly upstream" in this context means that there is/are no further nucleotides between the UTR defined in item (b) and the coding sequence which initiates with a start codon. Thus, the coding region which initiates with a start codon is immediately adjacent to said UTR sequence.

The RNA molecule may be present in the form of fused RNA sequences of modules (a) and (b) (defined in items (a) and (b), respectively, above) i.e., a (fusion) RNA molecule which is formed by the expression of a hybrid gene made by combining at least two nucleotide sequences encoding said modules. Typically, as will be explained in more detail further below, this can be accomplished by cloning a cDNA into an expression vector which allows for the transcription into the RNA molecule. Accordingly, the DNA molecule encoding the RNA molecule of the present invention may be a fused DNA sequence, i.e., a chimeric molecule which is formed by joining two or more polynucleotides via the phosphate group from one nucleotide bound to the 3' carbon on another nucleotide, forming a phosphodiester bond between the respective ends of one module and the end of another molecule. In this way, the above DNA molecules encoding said at least two modules are joined together in the form of a DNA molecule. Such a recombinant DNA molecule is then transcribed into its corresponding RNA nucleic acid sequence.

In one preferred embodiment, $R_2$ is selected from the group consisting of:

(i)
                                      (SEQ ID NO: 7)
GGGAGA;

(ii)
                                      (SEQ ID NO: 8)
GGGAGA;

(iii)
                                      (SEQ ID NO: 9)
GAAG;
and (iv)
                                      (SEQ ID NO: 10)
GGGA.

In a preferred embodiment, the RNA molecule comprising the sequence $R_2$-CNGCCACC (SEQ ID NO:2) is an RNA molecule, wherein the nucleotide N at position 2 of SEQ ID NO:2 is a nucleotide selected from the group consisting of U, G or C and wherein nucleotide N is not an A.

In another preferred embodiment, said nucleotide N at position 2 of SEQ ID NO:2 is U.

In a preferred embodiment, the RNA molecule of the present invention is an RNA molecule wherein the nucleotide following directly downstream of the start codon is not the nucleotide G. In another preferred embodiment, the RNA molecule of the present invention is an RNA molecule wherein the nucleotide following directly downstream of the start codon is a nucleotide selected from the group consisting of A, U and C.

In an even more preferred embodiment, the RNA molecule of the present invention is an RNA molecule which comprises a module (b1) as defined above, wherein said module (b1) is a sequence wherein the C at position 6 of SEQ ID NO:1 is substituted by an A and the C at position 7 of SEQ ID NO:1 is substituted by a G; and/or the A at position 5 of SEQ ID NO:1 is substituted by a G and wherein the nucleotide following directly downstream of the start codon is a nucleotide selected from the group consisting of A, U and C.

In another even more preferred embodiment, the RNA molecule of the present invention is an RNA molecule which comprises a module (b2) as defined above, wherein said module (b2) is a sequence wherein the C at position 7 of SEQ ID NO:2 is substituted by an A and the C at position 8 of SEQ ID NO:2 is substituted by a G; and/or the A at position 6 of SEQ ID NO:2 is substituted by a G and wherein the nucleotide following directly downstream of the start codon is a nucleotide selected from the group consisting of A, U and C.

As mentioned above, the Kozak consensus sequence (gcc)gccRccAUGG may, inter alia, be variant with respect to the nucleotide at position −3 (i.e., 3 nucleotides upstream from the start codon AUG) represented by an "R" as long as this position is a purine (i.e., adenine or guanine). In the above described UTRs, the nucleotide corresponding to this position is defined to be an "A". However, the present invention also relates to RNA molecules comprising a corresponding UTR which has a "G" at this position.

Accordingly, in a preferred embodiment, RNA molecule of the present invention contains a UTR as defined in item (b1), above, wherein in said UTR sequence of (b1), the A at position 5 of SEQ ID NO:1 is substituted by a G; or wherein in said UTR sequence of (b2) the A at position 6 of SEQ ID NO:2 is substituted by a G.

As mentioned above, the RNA molecule of the present invention may also harbour a poly-A tail. As used herein, a poly-A tail relates to a sequence of adenine nucleotides located at the 3' end of the RNA. A poly-A tail is commonly added to the 3' end of the RNA by a process called polyadenylation. Thus, the present invention relates to any of the above-described RNA, wherein the RNA molecule comprises a poly-A tail at the 3' end.

The length of the poly-A tail is not particularly limited. Yet, in preferred embodiments, the RNA molecule of the present invention comprises a poly-A tail at the 3' end wherein the poly-A tail has a length of at least 50, 60, 70, 80, 90, 100 or 110 nucleotides. In a more preferred embodiment, the RNA molecule of the present invention comprises a poly-A tail at the 3' end wherein the poly-A tail has a length of at least 120 nucleotides. In other preferred embodiments, the RNA molecule of the present invention comprises a poly-A tail at the 3' end wherein the poly-A tail has a length of at least 150, 200, 250, 300, 350, 400, 500, 600, 700, 800, 900 or 1000 nucleotides.

In case the RNA molecule of the present invention is produced by an in vitro transcription method as described herein further below the poly-A tail is located at the 3' end of the RNA adjacent to the UTR at the 3' end of the RNA molecule while the plasmid harbouring the RNA molecule of the present invention is linearized prior to the in vitro transcription downstream of the poly-A tail in order to assure that the in vitro transcribed RNA molecule contains said poly-A tail.

As mentioned above, the RNA molecule of the present invention may be present in the form of fused RNA sequences of modules (a) and (b), i.e., a (fusion) RNA molecule which is formed by the transcription of a hybrid gene made by combining at least two nucleotide sequences encoding said modules. Typically, this is accomplished by cloning a cDNA into an expression vector which allows for the transcription of the entire RNA molecule. A variety of methods are known for making fusion constructs, including nucleic acid synthesis, hybridization and/or amplification to produce a synthetic double-stranded nucleic acid molecule "encoding" the RNA molecule of the present invention. Such a double-stranded nucleic acid molecule (i.e., DNA molecule) harbours on one strand (i.e., on the coding or sense strand) the DNA sequence corresponding to the RNA molecule of the present invention and, accordingly, "encodes" the RNA molecule of the present invention. In other words, such a double-stranded nucleic acid/DNA molecule comprises on a strand the genetic information which corresponds to the transcribed RNA molecule of the present invention as defined herein above. The term "coding" or "encoding" in the context of the present invention is not only used in its conventional sense, i.e., to relate to a gene's DNA that codes for a protein (and, accordingly, the genetic information which may be translated into a polypeptide or a protein amino acid sequence). Rather, in terms of the present invention, in a construct wherein the individual DNA sequences encoding the modules (a) and (b) are "fused" or linked into a single (chimeric) DNA molecule, the construct also comprises a component (i.e., module (b)) which is not translated into a protein. Nevertheless, the DNA sequence corresponding to module (b) provides the information, i.e., the "code", for the 5' UTRs' structure and, accordingly, the term "encoding" in the present invention also relates to the genetic information for the UTRs which may be expressed, i.e., transcribed, if, e.g., present in a double-stranded nucleic acid molecule. Thus, the term "encoding" in the context of the present invention, although it is commonly only used to relate to the coding/expression of a protein, is to be understood in a way that the nucleic acid molecule can be transcribed into the corresponding RNA molecule which harbours parts encoding a protein or a polypeptide (i.e., module (a)) and parts "encoding" the UTR (i.e., module (b)) wherein the latter represent the final product when expressed since UTRs are not translated into proteins or polypeptides. Such a double-stranded nucleic acid may be inserted into expression vectors by standard molecular biology techniques (see, e.g. Sambrook et al., Molecular Cloning, A laboratory manual, 2nd Ed, 1989). The term "vector" such as "expression vector" or "cloning vector" in the sense of the present invention is understood as a circular, double-stranded unit of DNA that replicates within a cell independently of the chromosomal DNA and which is used as a vehicle to carry genetic material into a cell, where it can be replicated and/or expressed (i.e., transcribed into RNA and translated into a amino acid sequence). A vector containing foreign DNA is termed recombinant DNA. The vector itself is generally a DNA sequence that typically consists of an insert (i.e., module (b) which is not translated into a protein and module (a) the coding region) and a larger sequence that serves as the "backbone" of the vector. Plasmids in the sense of the present invention are most often found in bacteria and are used in recombinant DNA research to transfer genes between cells and are as such a subpopulation of "vectors" as used in the sense of the present invention.

Thus, the present invention also relates to a nucleic acid molecule encoding the RNA molecule of the present invention.

The nucleic acid is, for example a DNA, encoding the two main modules (i.e., module (a) and module (b)) of the RNA molecule of the present invention. The above nucleic acid molecule of the present invention preferably is a recombinant nucleic acid molecule. The nucleic acid molecule of the invention may be synthetic or semi-synthetic.

It is evident to the person skilled in the art that further regulatory sequences may be added to the nucleic acid molecule of the invention encoding the RNA molecule. For example, transcriptional enhancers and/or sequences which allow for induced expression may be employed. A suitable inducible system is for example tetracycline-regulated gene expression as described, e.g., by Gossen and Bujard, Proc. Natl. Acad. Sci. USA 89 (1992), 5547-5551) and Gossen, Trends Biotech. 12 (1994), 58-62, or a dexamethasone-inducible gene expression system as described, e.g. by Crook, EMBO J. 8 (1989), 513-519.

The present invention also relates to a vector, preferably an expression vector, comprising the nucleic acid molecule of the present invention.

As regards the vectors comprising a nucleic acid molecule encoding the RNA molecule of the present invention the same applies, mutatis mutandis, as has been set forth above in the context of the vectors comprising the DNA molecule of the present invention as defined above.

The present invention also relates to a host cell comprising the vector of the present invention. Thus, the present invention relates to a host transfected or transformed with the vector of the invention or a non-human host carrying the vector of the present invention, i.e. to a host cell or host which is genetically modified with a nucleic acid molecule according to the invention or with a vector comprising such a nucleic acid molecule.

As regards the host cell comprising the vector comprising a nucleic acid molecule encoding the RNA molecule of the present invention the same applies, mutatis mutandis, as has been set forth above in the context of the host cells comprising the vectors comprising the DNA molecule of the present invention as defined above.

The present invention also relates to methods of producing the RNA molecule of the present invention by culturing a host cell harbouring an expression vector encoding the individual modules of the present invention or the entire RNA molecule of the invention in culture medium, and recovering the RNA molecule from the host cell or culture medium. The present invention may also relate to a method for producing an RNA molecule of the present invention comprising the cultivation of the host cell of the present invention and optionally recovering the RNA molecule from the culture. Methods of recovering and/or subsequently purifying the RNA molecule of the present invention are known to the person skilled in the art.

The present invention also relates to methods of producing in an in vitro reaction the RNA molecule of the present invention by methods known to the person skilled in the art. More specifically, the RNA molecule of the present invention may be produced in vitro using an in vitro transcription system. In vitro transcription systems are commonly known and usually require a purified linear DNA template containing a DNA sequence "encoding" module (b) and module (a) as outlined above wherein said DNA sequence is under the control of an appropriate promoter. Moreover, an in vitro transcription system also commonly requires ribonucleotide triphosphates, a buffer system that includes DTT and magnesium ions, and an appropriate RNA polymerase which provides the enzymatic activity for the in vitro transcription of the DNA sequence into the RNA molecule of the present invention.

Methods which are commonly used to produce RNA molecules using in vitro transcription are well-known to the person skilled in the art and are, e.g., described in Methods Mol. Biol. 703 (2011):29-41.

As mentioned above, in case the RNA molecule of the present invention is produced by an in vitro transcription method as described herein further below the above poly-A tail may be part of the RNA molecule of the present invention (and not necessarily originally located on the cloning vector) and is located at the 3' end of the RNA, e.g. adjacent to the UTR at the 3' end of the RNA molecule. In case the RNA molecule of the present invention is produced by an in vitro transcription method the plasmid harbouring the RNA molecule of the present invention is linearized prior to the in vitro transcription downstream of the poly-A tail in order to assure that the in vitro transcribed RNA molecule contains said poly-A tail.

Alternatively, the RNA molecule of the present invention may also be chemically synthesized, e.g., by conventional chemical synthesis on an automated nucleotide sequence synthesizer using a solid-phase support and standard techniques.

The present invention also relates to methods of producing in an in vitro reaction the RNA molecule of the present invention by methods known to the person skilled in the art and as outlined above and recovering the RNA molecule from the reaction.

Methods of recovering and/or subsequently purifying the RNA molecule of the present invention are known to the person skilled in the art.

The RNA molecule of the present invention can readily be used in in vitro translation systems known in the art for the efficient expression of any desired polypeptide or protein encoded by the coding region of module (a).

In vitro translation systems are known in the art and can directly be used with the RNA molecule of the present invention. Alternatively, these in vitro translation systems can be combined with the above in vitro transcription systems. Corresponding cell-free systems for the in vitro transcription and/or in vitro translation are known and available. These cell-free systems for the protein synthesis (also called in-vitro protein synthesis or abbreviated CFPS), allow for the expression/production of a polypeptide or a protein using biological machinery without the use of living cells. In these systems, the in vitro protein synthesis environment is not constrained by a cell wall or homeostasis conditions necessary to maintain cell viability and enables direct access and control of the translation environment which is advantageous for a number of applications including optimization of protein production, optimization of protein complexes, to study protein synthesis, incorporating non-natural amino acids, high-throughput screens, and synthetic biology. Common components of a cell free reaction include a cell extract, an energy source, a supply of amino acids, cofactors such as magnesium, and the DNA or RNA encoding the desired polypeptide or protein. A cell extract may be obtained by lysing the cell of interest and centrifuging out the cell walls, DNA genome, and other debris. The remains are the necessary cell machinery including ribosomes, aminoacyl-tRNA synthetases, translation initiation and elongation factors, nucleases, etc. In a cell-free system for the synthesis of polypeptides or proteins starting from DNA (i.e., in a system including a step of in vitro transcription and in vitro translation), two types of DNA are commonly used, i.e., either plasmids or linear expression templates (LETs). In a cell-free system for the synthesis of polypeptides or proteins starting from RNA (i.e., in a system including a step of in vitro translation only) an RNA may directly be used. These in vitro cell-free reactions require an energy source which is usually provided by a separate mixture containing the needed energy source, along with a supply of amino acids which are added to the extract for the reaction. Common energy sources are phosphoenol pyruvate, acetyl phosphate, and creatine phosphate. Common cell extracts which are commonly used are made from *Escherichia coli* (ECE), rabbit reticulocytes (RRL), wheat germ (WGE), and insect cells (ICE). All of these extracts are commercially available.

Accordingly, the present invention also relates to the use of an RNA molecule of the present invention for the in vitro translation of a desired polypeptide or protein encoded by a coding region contained in said RNA molecule.

As regards the preferred embodiments of such a use of an RNA molecule of the present invention, the same applies, mutatis mutandis, as has been set forth above in the context of the RNA molecule as defined above.

The RNA molecules as defined above are particularly useful in medical settings and in the treatment of a certain disease and, in particular, in RNA-based therapies. Thus, the present invention also relates to a pharmaceutical composition comprising the RNA molecule of the present invention, the nucleic acid molecule of the present invention, the vector of the present invention or the host cell of the present invention and optionally a pharmaceutically acceptable carrier.

The term "treatment" and the like are used herein to generally mean obtaining a desired pharmacological and/or physiological effect. Accordingly, the treatment of the present invention may relate to the treatment of (acute) states of a certain disease but may also relate to the prophylactic treatment in terms of completely or partially preventing a disease or symptom thereof. Preferably, the term "treatment" is to be understood as being therapeutic in terms of partially or completely curing a disease and/or adverse effect and/or symptoms attributed to the disease. "Acute" in this respect means that the subject shows symptoms of the disease. In other words, the subject to be treated is in actual need of a treatment and the term "acute treatment" in the context of the present invention relates to the measures taken to actually treat the disease after the onset of the disease or the breakout of the disease. The treatment may also be prophylactic or preventive treatment, i.e., measures taken for disease prevention, e.g., in order to prevent the infection and/or the onset of the disease.

The pharmaceutical composition of the present invention may be administered via a large range of classes of forms of administration known to the skilled person. Administration may be systemically, locally, orally, through aerosols including but not limited to tablets, needle injection, the use of inhalators, creams, foams, gels, lotions and ointments.

As mentioned, the present invention relates to a pharmaceutical composition, comprising an effective amount of the RNA molecule (or the nucleic acid molecule, the vector or the host cell) of the present invention in accordance with the above and at least one pharmaceutically acceptable excipient or carrier.

An excipient or carrier is an inactive substance formulated alongside the active ingredient, i.e., the RNA molecule (or the nucleic acid molecule, the vector or the host cell) of the present invention for the purpose of bulking-up formulations that contain potent active ingredients. Excipients are often referred to as "bulking agents," "fillers," or "diluents". Bulking up allows convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors.

Thus, the pharmaceutical composition comprising an effective amount of the RNA molecule (or the nucleic acid molecule, the vector or the host cell) of the present invention may be in solid, liquid or gaseous form and may be, inter alia, in a form of (a) powder(s), (a) tablet(s), (a) solution(s) or (an) aerosol(s). It is preferred that said pharmaceutical composition optionally comprises a pharmaceutically acceptable carrier and/or diluent.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e., in "an effective amount" which can easily be determined by the skilled person by methods known in the art. The dosage regimen will be determined by the attending physician and clinical factors. As is well known in the medical arts, dosages for any one patient depends upon many factors, including the patient's or subject's size, body surface area, age, the particular compound to be administered, sex, time and route of administration, general health, and other drugs being administered concurrently.

Thus, preferably, the RNA molecule (or the nucleic acid molecule, the vector or the host cell) of the present invention is included in an effective amount. The term "effective amount" refers to an amount sufficient to induce a detectable therapeutic response in the subject to which the pharmaceutical composition is to be administered. In accordance with the above, the content of the RNA molecule (or the nucleic acid molecule, the vector or the host cell) of the present invention in the pharmaceutical composition is not limited as far as it is useful for treatment as described above, but preferably contains 0.0000001-10% by weight per total composition. Further, the RNA molecule (or the nucleic acid molecule, the vector or the host cell) described herein is preferably employed in a carrier. Generally, an appropriate amount of a pharmaceutically acceptable salt is used in the carrier to render the composition isotonic. Examples of the carrier include but are not limited to saline, Ringer's solution and dextrose solution. Preferably, acceptable excipients, carriers, or stabilisers are non-toxic at the dosages and concentrations employed, including buffers such as citrate, phosphate, and other organic acids; salt-forming counterions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co.

Therapeutic progress can be monitored by periodic assessment. The RNA molecule (or the nucleic acid molecule, the vector or the host cell) of the present invention or the pharmaceutical composition of the invention may be in sterile aqueous or non-aqueous solutions, suspensions, and emulsions as well as creams and suppositories. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be, e.g., polyoxyethylene sorbitan monolaurate, available on the market with the commercial name Tween, propylene glycol, EDTA, Citrate, Sucrose as well as other agents being suitable for the intended use of the pharmaceutical composition that are well-known to the person skilled in the art.

In accordance with this invention, the term "pharmaceutical composition" relates to a composition for administration to a patient, preferably a human patient.

The pharmaceutical composition of the present invention may be for use in RNA-based therapies. As mentioned above, the RNA molecule of the present invention comprising a "coding region coding for a polypeptide" can be used in RNA-based therapies wherein the "coding region coding for a polypeptide" encodes a therapeutically or pharmaceutically active polypeptide or protein having a therapeutic or preventive effect. Thus, in preferred embodiments, the pharmaceutical composition of the present invention may be for use in RNA-based therapies in the treatment or prevention of a disease as recited in the above Table 1. Accordingly, RNA-based therapies in accordance with the present invention may be for use in the treatment or prevention of a disease as recited in the above Table 1.

Thus, the pharmaceutical composition of the present invention may be for use in RNA-based therapies in cases where the gene defects described in the above Table 1 lead to a disease which can then be treated or prevented by a transcript replacement therapy/enzyme replacement therapy with the RNA molecule of the present invention, wherein the RNA molecule comprises a "coding region for a polypeptide" which encodes an intact version of the protein or a functional fragment thereof compensating the disclosed defective gene. In particularly preferred embodiments, the pharmaceutical composition of the present invention may be for use in RNA-based therapies in the treatment or prevention of lysosomal diseases like Gaucher disease, Fabry disease, MPS I, MPS II (Hunter syndrome), MPS VI and Glycogen storage diseases such as for example Glycogen storage disease type I (von Gierecke's disease), type II (Pompe's disease), type III (Cod's disease, type IV (Andersen's disease, type V (McArdle's disease, type VI (Hers disease), type VII (Tauri's disease), type VII, type IX, type X, type XI (Fanconi-Bickel syndrome), type XI, or type 0. Transcript replacement therapies/enzyme replacement therapies beneficially do not affect the underlying genetic defect, but increase the concentration of the enzyme in which the patient is deficient. As an example, in Pompe's disease, the transcript replacement therapy/enzyme replacement therapy replaces the deficient Lysosomal enzyme acid alpha-glucosidase (GAA).

In other preferred embodiments, the pharmaceutical composition of the present invention may be for use in RNA-based therapies in accordance with the present invention wherein the "coding region coding for a polypeptide" encodes a therapeutically or pharmaceutically active polypeptide, protein or peptide having a therapeutic or preventive effect, wherein said polypeptide, protein or peptide is selected from the group encoded by the genes as outlined in Table 1.

In other preferred embodiments, RNA-based therapies in accordance with the present invention may be for use in treating cancer, a cardiovascular disease, a viral infection, an immune dysfunction, an autoimmune disease, a neurologic disorder, an inherited metabolic disorders or a genetic disorder or any disease where a protein or protein fragment produced in a cell may have a beneficial effect for the patent. Examples of cancer include head and neck cancer, breast cancer, renal cancer, bladder cancer, lung cancer, prostate cancer, bone cancer, brain cancer, cervical cancer, anal cancer, colon cancer, colorectal cancer, appendix cancer, eye cancer, gastric cancer, leukemia, lymphoma, liver cancer, skin cancer, ovarian cancer, penile cancer, pancreatic cancer, testicular cancer, thyroid cancer, vaginal cancer, vulvar cancer, endometrial cancer, cardiac cancer and sarcoma.

Examples of cardiovascular diseases include atherosclerosis, coronary heart disease, pulmonary heart disease and cardiomyopathy.

Examples of immune dysfunctions and autoimmune diseases include, but are not limited to, rheumatic diseases, multiple sclerosis and asthma.

Examples of viral infections include, but are not limited to, infections with human immunodeficiency virus, herpes simplex virus, human papillomavirus as well as hepatitis B and C virus.

Examples of neurologic disorders include, but are not limited to, Parkinson's disease, multiple sclerosis, and dementia.

Examples of inherited metabolic disorders include, but are not limited to, Gaucher's disease and Phenylketonuria.

The invention also relates to a method of an RNA-based therapy. Thus, the present invention relates to a method for the treatment of a disease such as cancer, a cardiovascular disease, a viral infection, an immune dysfunction, an autoimmune disease, a neurologic disorder, an inherited metabolic disorders or a genetic disorder by an RNA-based therapy. As regards the preferred embodiments of the method for treatment the same applies, mutatis mutandis, as has been set forth above in the context of the RNA molecule or the pharmaceutical composition for use in RNA-based therapy as defined above.

In the present invention, the subject is, in a preferred embodiment, a mammal such as a dog, cat, pig, cow, sheep, horse, rodent, e.g., rat, mouse, and guinea pig, or a primate, e.g., gorilla, chimpanzee, and human. In a most preferable embodiment, the subject is a human.

As mentioned above, the RNA molecules as defined above are particularly useful in medical settings and in the treatment of a certain disease and, in particular, in RNA-based therapies. Thus, the present invention also relates to a pharmaceutical composition comprising the RNA molecule, the nucleic acid molecule, the vector or the host cell of the present invention and optionally a pharmaceutically acceptable carrier.

Yet, in RNA therapies, it is often desirable to silence the effect of the RNA molecule at some stage.

This can, e.g., be done by making use of an RNAi (RNA interference) mechanism by using the nucleic acid strand which is complementary to the UTR sequence of the present invention. In fact, the small size of the minimal UTRs of the present invention makes this approach feasible since these UTRs do not form secondary or tertiary structures and they do not exist in normal cells. Accordingly, the complementary strand of such a UTR sequence may beneficially be used in medical settings after the treatment of the above diseases or after the above RNA-based therapies using the pharmaceutical composition of the present invention, thereby silencing the therapeutic RNA molecules of the present invention.

Thus, an RNAi-approach is also envisaged in context of this invention for use in the preparation of a pharmaceutical composition for silencing the effect of the therapeutic RNA molecules of the present invention.

The term "RNA interference" or "inhibiting RNA" (RNAi/iRNA) describes the use of double-stranded RNA to target specific mRNAs for degradation, thereby silencing their expression. Preferred inhibiting RNA molecules may be selected from the group consisting of double-stranded RNA (dsRNA), RNAi, siRNA, shRNA and stRNA. dsRNA matching a gene sequence is synthesized in vitro and introduced into a cell. The dsRNA may also be introduced into a cell in form of a vector expressing a target gene sequence in sense and antisense orientation, for example in form of a hairpin mRNA. The sense and antisense sequences may also be expressed from separate vectors, whereby the individual antisense and sense molecules form double-stranded RNA upon their expression. It is known in the art that in some occasions the expression of a sequence in sense orientation or even of a promoter sequence suffices to give rise to dsRNA and subsequently to siRNA due to internal amplification mechanisms in a cell. Accordingly, all means and methods which result in a decrease in activity of the polypeptide or protein encoded by the coding region are to be used in accordance with the present invention. For example sense constructs, antisense constructs, hairpin constructs, sense and antisense molecules and combinations thereof can be used to generate/introduce these siRNAs. The dsRNA feeds into a natural, but only partially understood process including the highly conserved nuclease dicer which cleaves dsRNA precursor molecules into short interfering RNAs (siRNAs). The generation and preparation of siRNA(s) as well as the method for inhibiting the expression of a target gene is, inter alia, described in WO 02/055693, Wei (2000) Dev. Biol. 15:239-255; La Count (2000) Biochem. Paras. 111:67-76; Baker (2000) Curr. Biol. 10:1071-1074; Svoboda (2000) Development 127:4147-4156 or Marie (2000) Curr. Biol. 10:289-292. These siRNAs built then the sequence specific part of an RNA-induced silencing complex (RISC), a multicomplex nuclease that destroys messenger RNAs homologous to the silencing trigger). Elbashir (2001) EMBO J. 20:6877-6888 showed that duplexes of 21 nucleotide RNAs may be used in cell culture to interfere with gene expression in mammalian cells. It is already known that RNAi is mediated very efficiently by siRNA in mammalian cells but the generation of stable cell lines or non-human transgenic animals was limited. However, new generations of vectors may be employed in order to stably express, e.g. short hairpin RNAs (shRNAs). Stable expression of siRNAs in Mammalian Cells is inter alia shown in Brummelkamp (2002) Science 296:550-553. Also Paul (2002) Nat. Biotechnol. 20:505-508 documented the effective expression of small interfering RNA in human cells. RNA interference by expression of short-interfering RNAs and hairpin RNAs in mammalian cells was also shown by Yu (2002) PNAS 99:6047-6052. The shRNA approach for gene silencing is well known in the art and may comprise the use of st (small temporal) RNAs; see, inter alia, Paddison (2002) Genes Dev. 16:948-958. These approaches may be vector-based, e.g. the pSUPER vector, or RNA polIII vectors may be employed as illustrated, inter alia, in Yu (2002), loc. cit.; Miyagishi (2002), loc. cit. or Brummelkamp (2002), loc. cit. It is envisaged that the regulatory sequences of the present invention are used in similar fashion as the systems based on pSUPER or RNA polIII vectors.

Methods to deduce and construct siRNAs are known in the art and are described in Elbashir (2002) Methods 26:199-213, at the internet web sites of commercial vendors of siRNA, e.g. Qiagen GmbH (https://www1.qiagen.com/GeneGlobe/Default.aspx); Dharmacon (www.dharmacon.com); Xeragon Inc. (http://www.dharmacon.com/Default.aspx), and Ambion (www.ambion.com), or at the web site of the research group of Tom Tuschl (http://www.rockefeller.edu/labheads/tuschl/sirna.html). In addition, programs are available online to deduce siRNAs from a given mRNA sequence (e.g. http://www.ambion.com/techlib/misc/siRNA_finder.html or http://katandin.cshl.org:9331/RNAi/html/rnai.html). Uridine residues in the 2-nt 3' overhang can be replaced by 2'deoxythymidine without loss of activity, which significantly reduces costs of RNA synthesis and may also enhance resistance of siRNA duplexes when applied to mammalian cells (Elbashir (2001) loc. cit). The siRNAs may also be sythesized enzymatically using T7 or other RNA polymerases (Donze (2002) Nucleic Acids Res 30:e46). Short RNA duplexes that mediate effective RNA interference (esiRNA) may also be produced by hydrolysis with *Escherichia coli* RNase III (Yang (2002) PNAS 99:9942-9947). Furthermore, expression vectors have been developed to express double stranded siRNAs connected by small hairpin RNA loops in eukaryotic cells (e.g. (Brummelkamp (2002) Science 296:550-553). All of these constructs may be developed with the help of the programs named above. In addition, commercially available sequence prediction tools incorporated in sequence analysis programs or sold separately, e.g. the siRNA Design Tool offered by www.oligoEngine.com (Seattle, Wash.) may be used for siRNA sequence prediction.

Accordingly, specific interfering RNAs can be used in accordance with the present invention as antagonists/silencers of the expression and/or function of the polypeptide or protein encoded by the coding region of the RNA molecule of the present invention. These siRNAs are formed by a complementary/antisense and a sense strand, whereby the antisense/sense strand preferably comprises at least 10, more preferably at least 12, more preferably at least 14, more preferably at least 16, more preferably at least 18, more preferably at least 19, 20, 21 or 22 nucleotides. In an even more preferred embodiment, the antisense/sense strand preferably comprises 25 or more nucleotides.

As mentioned above, methods for preparing siRNAs to be used in accordance with the present invention are well known in the art. Based on the teaching provided herein, a skilled person in the art is easily in the position not only to prepare such siRNAs but also to assess whether a siRNA is capable of antagonizing/inhibiting/silencing the polypeptide or protein encoded by the coding region of the RNA molecule of the present invention. It is envisaged herein that the above described siRNAs lead to a degradation of the RNA molecule of the present invention harbouring a coding region encoding a polypeptide or protein and an UTR module, and thus to a decreased polypeptide/protein level of the polypeptide or protein encoded by the coding region of the RNA molecule of the present invention.

Accordingly, the present invention relates to an RNA molecule which is complementary to a UTR of the present invention as described herein-above.

In a preferred embodiment, said RNA molecule complementary to the UTR of the present invention comprises the sequence CAUGGUGGCGUCUCCC (SEQ ID NO:11 or a sequence which shows 1 to 4 substitutions in comparison to SEQ ID NO:11.

In another preferred embodiment, said RNA molecule complementary to the UTR of the present invention comprises the sequence CAUGGUGGCNGUCUCCC (SEQ ID NO:12), wherein the nucleotide N at position 10 of SEQ ID NO:12 is a nucleotide selected from the group consisting of U, G, C or A, or a sequence which shows 1 to 4 substitutions in comparison to SEQ ID NO:12 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUCUUGGCGUCUCCC (SEQ ID NO:13), or a sequence which shows 1 to 4 substitutions in comparison to SEQ ID NO:13.

In another preferred embodiment, said RNA molecule complementary to the UTR of the present invention comprises the sequence CAUCUUGGCNGUCUCCC (SEQ ID NO:14), wherein the nucleotide N at position 10 of SEQ ID NO:14 is a nucleotide selected from the group consisting of U, G, C or A while A is more preferred, or a sequence which shows 1 to 4 substitutions in comparison to SEQ ID NO:14 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUGGCGGCGUCUCCC (SEQ ID NO:15), or a sequence which shows 1 to 4 substitutions in comparison to SEQ ID NO:15.

In another preferred embodiment, said RNA molecule complementary to the UTR of the present invention comprises the sequence CAUGGCGGCNGUCUCCC (SEQ ID NO:16), wherein the nucleotide N at position 10 of SEQ ID NO:16 is a nucleotide selected from the group consisting of U, G, C or A, or a sequence which shows 1 to 4 substitutions in comparison to SEQ ID NO:16 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUCUCGGCGUCUCCC (SEQ ID NO:17), or a sequence which shows 1 to 4 substitutions in comparison to SEQ ID NO:17.

In another preferred embodiment, said RNA molecule complementary to the UTR of the present invention comprises the sequence CAUCUCGGCNGUCUCCC (SEQ ID NO:18), wherein the nucleotide N at position 10 of SEQ ID NO:18 is a nucleotide selected from the group consisting of U, G, C or A while A is more preferred, or a sequence which shows 1 to 4 substitutions in comparison to SEQ ID NO:18 and which is capable of antagonizing/inhibiting/silencing the polypeptide or protein encoded by the coding region of the RNA molecule of the present invention.

In another preferred embodiment, said RNA molecule complementary to the UTR of the present invention comprises the sequence CAUGGUGGCGUCCC (SEQ ID NO:19), or a sequence which shows 1 to 4 substitutions in comparison to SEQ ID NO:19.

In another preferred embodiment, said RNA molecule complementary to the UTR of the present invention comprises the sequence CAUGGUGGCNGUCCC (SEQ ID NO:20), wherein the nucleotide N at position 10 of SEQ ID NO:20 is a nucleotide selected from the group consisting of U, G, C or A, or a sequence which shows 1 to 4 substitutions in comparison to SEQ ID NO:20 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUCUUGGCGUCCC (SEQ ID NO:21), or a sequence which shows 1 to 4 substitutions in comparison to SEQ ID NO:21.

In another preferred embodiment, said RNA molecule complementary to the UTR of the present invention comprises the sequence CAUCUUGGCNGUCCC (SEQ ID NO:22), wherein the nucleotide N at position 10 of SEQ ID NO:22 is a nucleotide selected from the group consisting of U, G, C or A while A is more preferred, or a sequence which shows 1 to 4 substitutions in comparison to SEQ ID NO:22 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUGGCGGCGUCCC (SEQ ID NO:23), or a sequence which shows 1 to 4 substitutions in comparison to SEQ ID NO:23.

In another preferred embodiment, said RNA molecule complementary to the UTR of the present invention comprises the sequence CAUGGCGGCNGUCCC (SEQ ID NO:24), wherein the nucleotide N at position 10 of SEQ ID NO:24 is a nucleotide selected from the group consisting of U, G, C or A, or a sequence which shows 1 to 4 substitutions in comparison to SEQ ID NO:24 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUCUCGGCGUCCC (SEQ ID NO:25), or a sequence which shows 1 to 4 substitutions in comparison to SEQ ID NO:25.

In another preferred embodiment, said RNA molecule complementary to the UTR of the present invention comprises the sequence CAUCUCGGCNGUCCC (SEQ ID NO:26), wherein the nucleotide N at position 10 of SEQ ID NO:26 is a nucleotide selected from the group consisting of U, G, C or A while A is more preferred, or a sequence which shows 1 to 4 substitutions in comparison to SEQ ID NO:26 and which is capable of antagonizing/inhibiting/silencing the polypeptide or protein encoded by the coding region of the RNA molecule of the present invention.

In another preferred embodiment, said RNA molecule complementary to the UTR of the present invention comprises the sequence CAUGGUGGCGCUUC (SEQ ID NO:27), or a sequence which shows 1 to 4 substitutions in comparison to SEQ ID NO:27.

In another preferred embodiment, said RNA molecule complementary to the UTR of the present invention comprises the sequence CAUGGUGGCNGCUUC (SEQ ID NO:28), wherein the nucleotide N at position 10 of SEQ ID NO:28 is a nucleotide selected from the group consisting of U, G, C or A, or a sequence which shows 1 to 4 substitutions in comparison to SEQ ID NO:28 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUCUUGGCGCUUC (SEQ ID NO:29), or a sequence which shows 1 to 4 substitutions in comparison to SEQ ID NO:29.

In another preferred embodiment, said RNA molecule complementary to the UTR of the present invention comprises the sequence CAUCUUGGCNGCUUC (SEQ ID NO:30), wherein the nucleotide N at position 10 of SEQ ID NO:30 is a nucleotide selected from the group consisting of U, G, C or A while A is more preferred, or a sequence which shows 1 to 4 substitutions in comparison to SEQ ID NO:30 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUGGCGGCGCUUC (SEQ ID NO:31), or a sequence which shows 1 to 4 substitutions in comparison to SEQ ID NO:31.

In another preferred embodiment, said RNA molecule complementary to the UTR of the present invention comprises the sequence CAUGGCGGCNGCUUC (SEQ ID NO:32), wherein the nucleotide N at position 10 of SEQ ID NO:32 is a nucleotide selected from the group consisting of U, G, C or A, or a sequence which shows 1 to 4 substitutions in comparison to SEQ ID NO:32 and which is capable of antagonizing/inhibiting/silencing the polypeptide or protein encoded by the coding region of the RNA molecule of the present invention.

In a preferred embodiment, said RNA molecule complementary to the UTR of the present invention comprises the sequence CAUCUCGGCGCUUC (SEQ ID NO:33), or a sequence which shows 1 to 4 substitutions in comparison to SEQ ID NO:33.

In another preferred embodiment, said RNA molecule complementary to the UTR of the present invention comprises the sequence CAUCUCGGCNGCUUC (SEQ ID NO:34), wherein the nucleotide N at position 10 of SEQ ID NO:34 is a nucleotide selected from the group consisting of U, G, C or A while A is more preferred, or a sequence which shows 1 to 4 substitutions in comparison to SEQ ID NO:34 and which is capable of antagonizing/inhibiting/silencing the polypeptide or protein encoded by the coding region of the RNA molecule of the present invention.

In another preferred embodiment, the present invention relates to an RNA molecule selected from the group consisting of SEQ ID NO:11 to 34 which harbours (an) additional nucleotide(s) at the 5' end which extends beyond the triplet complementary to the start codon and which is complementary to the sequences of the desired polypeptide or protein encoded by the coding region of the RNA molecule of the present invention. Preferably, the complementary sequences comprising the above sequences complementary to the UTR sequences of the present invention (i.e., an RNA molecule selected from the group consisting of SEQ ID NO:11 to 34) preferably comprises at least 15, more preferably at least 16, more preferably at least 17, more preferably at least 18, more preferably at least 19, more preferably at least 20, 21, 22, 23 or 24 nucleotides. In an even more preferred embodiment, these sequences comprise 25, 30, 35, 40 or more nucleotides. Increasing the length at the 5' end may be desired in order to increase the specificity of the complementary sequence thereby preventing undesired side effects.

In another preferred embodiment, the present invention not only relates to any of the above RNA molecules but also to an RNA molecule selected from the group consisting of SEQ ID NO:11 to 34 which comprises up to 5%, 10%, 20% or 30% mismatches to the RNA molecules described above. Furthermore, the RNA molecules can be chemically modified as described herein-above.

The present invention also relates to a kit comprising a DNA molecule of the present invention, an RNA molecule of the present invention, a nucleic acid molecule of the present invention, a vector of the present invention or a host cell of the present invention. As regards the preferred embodiments, the same applies, mutatis mutandis, as has been set forth above in the context of the DNA molecule, RNA molecule, nucleic acid molecule, vector or the host cell according to the present invention. Advantageously, the kit of the present invention further comprises, optionally (a) buffer(s), storage solutions and/or remaining reagents or materials required for the conduct of the above and below uses and methods. Furthermore, parts of the kit of the invention can be packaged individually in vials or bottles or in combination in containers or multicontainer units. The kit of the present invention may be advantageously used, inter alia, for carrying out the methods of the invention or for the preparation of the RNA molecule of the invention and could be employed in a variety of applications referred herein, e.g., in the uses as outlined above and below. Another component that can be included in the kit is instructions to a person using a kit for its use. The manufacture of the kits follows preferably standard procedures which are known to the person skilled in the art.

The present invention also relates to the use of a UTR as described herein-above for translating a coding region of an RNA molecule into a polypeptide or a protein encoded by said coding region.

In a more preferred embodiment, the present invention also relates to the use of a UTR as described herein-above for increasing the efficiency of translating a coding region of an RNA molecule into a polypeptide or a protein encoded by said coding. As regards the preferred embodiments of the use the same applies, mutatis mutandis, as has been set forth above in the context of the RNA molecule of the present invention.

In preferred embodiments, the present invention relates to the following as characterized by the following items 1 to 20:

1. A DNA molecule, which can be transcribed into an mRNA, comprising one strand with the following elements:
    (a) a coding region, including a start codon at its 5' end, coding for a polypeptide; and
    (b) directly upstream of said coding sequence a sequence selected from the group consisting of:
        (b1)

$R_1$-CGCCACC; (SEQ ID NO: 1)

or a sequence wherein in said sequence the C at position 6 of SEQ ID NO:1 is substituted by an A and the C at position 7 of SEQ ID NO:1 is substituted by a G; and/or the A at position 5 of SEQ ID NO:1 is substituted by a G; and
        (b2) $R_1$-CNGCCACC (SEQ ID NO:2), wherein the nucleotide N at position 2 of SEQ ID NO:2 is a nucleotide selected from the group consisting of T, G, C or A;
        or a sequence wherein in said sequence the C at position 7 of SEQ ID NO:2 is substituted by an A and the C at position 8 of SEQ ID NO:2 is substituted by a G; and/or the A at position 6 of SEQ ID NO:2 is substituted by a G,
    wherein $R_1$ is a promoter which is recognized by a DNA-dependent RNA-polymerase;
    or comprising the complementary strand.
2. The DNA molecule according to item 1, wherein the promoter which is recognized by a DNA-dependent RNA polymerase is selected from the group consisting of:
    (i) TAATACGACTCACTATAGGGAGA (SEQ ID NO: 3) or a sequence which shows 1 to 6 substitutions in comparison to SEQ ID NO:3 and which is recognized by a T7 DNA-dependent RNA polymerase;
    (ii) AATTAACCCTCACTAAAGGGAGA (SEQ ID NO: 4) or a sequence which shows 1 to 6 substitutions in comparison to SEQ ID NO:4 and which is recognized by a T3 DNA-dependent RNA polymerase;
    (iii) ATTTAGGTGACACTATAGAAG (SEQ ID NO: 5) or a sequence which shows 1 to 6 substitutions in comparison to SEQ ID NO:5 and which is recognized by a SP6 DNA-dependent RNA polymerase; and
    (iv) AATTAGGGCACACTATAGGGA (SEQ ID NO: 6) or a sequence which shows 1 to 6 substitutions in comparison to SEQ ID NO:6 and which is recognized by a K11 DNA-dependent RNA polymerase.
3. The DNA molecule according to item 1 or 2, wherein the nucleotide N at position 2 of SEQ ID NO:2 is a nucleotide selected from the group consisting of T, G or C and wherein nucleotide N is not an A.
4. The DNA molecule according to item 3, wherein said nucleotide N at position 2 of SEQ ID NO:2 is T.
5. A vector comprising the DNA molecule of item 4.
6. A host cell comprising the vector of item 5.
7. A composition comprising:
    the DNA molecule according to any one of items 1 to 4, the vector according to item 5 or the host cell according to item 6.
8. An RNA molecule comprising
    (a) a coding region, including a start codon at its 5' end, coding for a polypeptide; and
    (b) directly upstream of said coding sequence a UTR selected from the group consisting of:

(b1) a UTR of the sequence $$R_2\text{-CGCCACC,} \quad (\text{SEQ ID NO: 1})$$

or a sequence wherein in said UTR sequence the C at position 6 of SEQ ID NO:1 is substituted by an A and the C at position 7 of SEQ ID NO:1 is substituted by a G; and/or the A at position 5 of SEQ ID NO:1 is substituted by a G; and (b2) a UTR of the sequence R$_2$-CNGCCACC (SEQ ID NO:2), wherein the nucleotide N at position 2 of SEQ ID NO:2 is a nucleotide selected from the group consisting of U, G, C or A, or a sequence wherein in said UTR sequence the C at position 7 of SEQ ID NO:2 is substituted by an A and the C at position 8 of SEQ ID NO:2 is substituted by a G; and/or the A at position 6 of SEQ ID NO:2 is substituted by a G, wherein R$_2$ is an RNA sequence corresponding to the part of a promoter region starting with the nucleotide where a DNA-dependent RNA-polymerase initiates RNA synthesis.

9. The RNA molecule according to item 8, wherein R$_2$ is selected from the group consisting of:

(i)
GGGAGA; (SEQ ID NO: 7)

(ii)
GGGAGA; (SEQ ID NO: 8)

(iii)
GAAG; (SEQ ID NO: 9)
and (iv)
GGGA. (SEQ ID NO: 10)

10. The RNA molecule according to item 8 or 9, wherein the nucleotide N at position 2 of SEQ ID NO:2 is a nucleotide selected from the group consisting of U, G or C and wherein nucleotide N is not an A.

11. The RNA molecule according to item 10, wherein said nucleotide N at position 2 of SEQ ID NO:2 is U.

12. The RNA molecule according to any one of items 8 to 11, wherein the RNA molecule comprises a poly-A tail at the 3' end.

13. The RNA molecule according to any one of items 8 to 12, wherein the poly-A tail has a length of at least 120 nucleotides.

14. A nucleic acid molecule encoding the RNA molecule of any one of items 8 to 13.

15. A vector comprising the nucleic acid molecule of item 14.

16. A host cell comprising the vector of item 15.

17. A pharmaceutical composition comprising the RNA molecule according to any one of items 8 to 13, the nucleic acid molecule according to item 14, the vector according to item 15 or the host cell according to item 16 and optionally a pharmaceutically acceptable carrier.

18. The pharmaceutical composition of item 17 for use in RNA-based therapies.

19. A kit comprising the DNA molecule according to any one of items 1 to 4, the RNA molecule according to any one of items 8 to 13, the nucleic acid molecule according to item 14, the vector according to item 5 or 15 or the host cell according to item 6 or 16.

20. Use of an UTR as defined in item 8(b) for translating a coding region of an RNA molecule into a polypeptide or a protein encoded by said coding region.

The patent or application file contains at least one drawing executed in color. Copies of this patent or patent application publication with color drawings will be provided by the Office upon request and payment of the necessary fee.

FIG. 1: shows the sequences harbouring a "minimal UTR" sequence together with the name of the respective luciferase reporter constructs used in the present invention. The sequences harbour parts of the T7 Promoter and of the Kozak element followed by a start codon ATG. The first 10 bases including the TATA sequence and the subsequent 6 bases (GGGAGA) are T7 promoter derived sequences while the remaining bases upstream the start codon ATG belong to the Kozak element (GCCACC). "Sp30" is a random sequence of 30 nucleotides. The sequence underlined in sequence No. 9 is the 5' UTR sequence from human alpha globin ("hAg") having a length of 30 nucleotides. Sequences 1 to 9 as shown in FIG. 1 correspond to SEQ ID NOs:37 to 45, respectively.

FIGS. 2A and B: shows that the extra "C" in the "minimal UTR" is essential (sequence No. 1 and No. 2 in FIG. 1). Human alveolar epithelial cell line (A549) and human hepatocellular carcinoma cell line (HepG2) were seeded at the density of 20,000 cells/well and 40,000 cells/well respectively in a 96 well plate. 24 hours post seeding, cells were transfected with different luciferase coding SNIM RNA constructs (sequence 1 and 2 in FIG. 1) using Lipofectamine2000. Luciferase expression was measured at 24 hours post transfection. Values represent mean±SD of 3 replicates and were plotted against the transfection dose and data analysed via GraphPad Prism. In both A549 and HepG2 cells, deletion of C resulted in lower expression. Therefore this extra C was included in the design of all further constructs.

Figure 3:
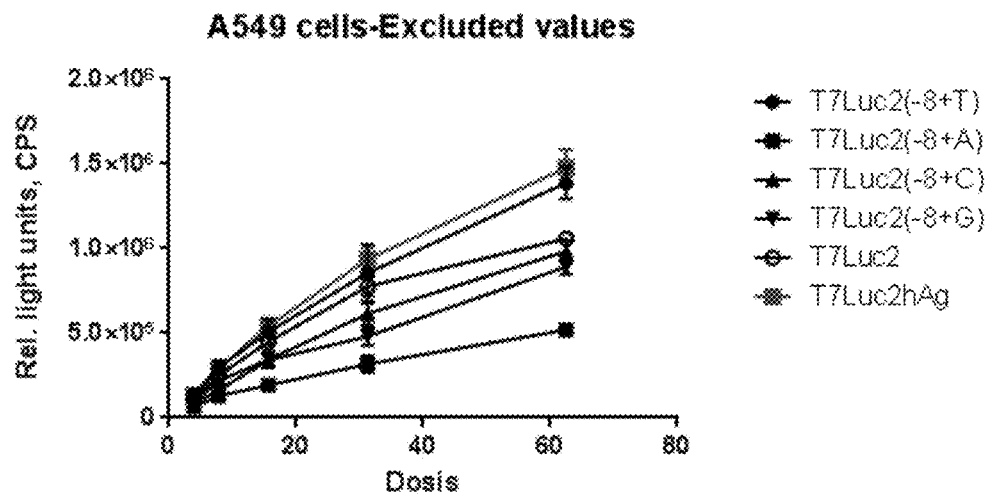

FIG. 3: shows the effect of individual nucleotides as indicated and demonstrates the effect of the distance between the extra "C" and the Kozak element in A549 transfected cells. Cells transfected and luciferase assay performed a described under Materials and Methods. As higher doses were out of the linear range, only dose response up to 62.5 ng/well is presented here. 5'UTR from human alpha globin was used as positive control. Transfection experiments were performed with SNIM RNA molecules harbouring sequences 3-8 from FIG. 1, respectively. Human alveolar epithelial cell line (A549) were seeded at the density of 20,000 cells/well in a 96 well plate. 24 hours post seeding, cells were transfected with different luciferase coding SNIM RNA constructs (sequences No. 3-8 from FIG. 1) using Lipofectamine2000. Luciferase expression was measured at 24 hours post transfection. Values plotted against the transfection dose and data analysed via GraphPad Prism. Values represent mean±SD of 3 replicates.

In alveolar epithelial cell line (A549), insertion of an extra "A" between C and Kozak element (sequence No. 3 in FIG. 1) resulted in significantly lower expression (FIG. 3). Insertion of a single "T" between C and Kozak element (sequence No. 4 in FIG. 1) resulted in expression levels comparable to that achieved with human alpha globin 5'UTR which was used as a positive control.

Figure 4:
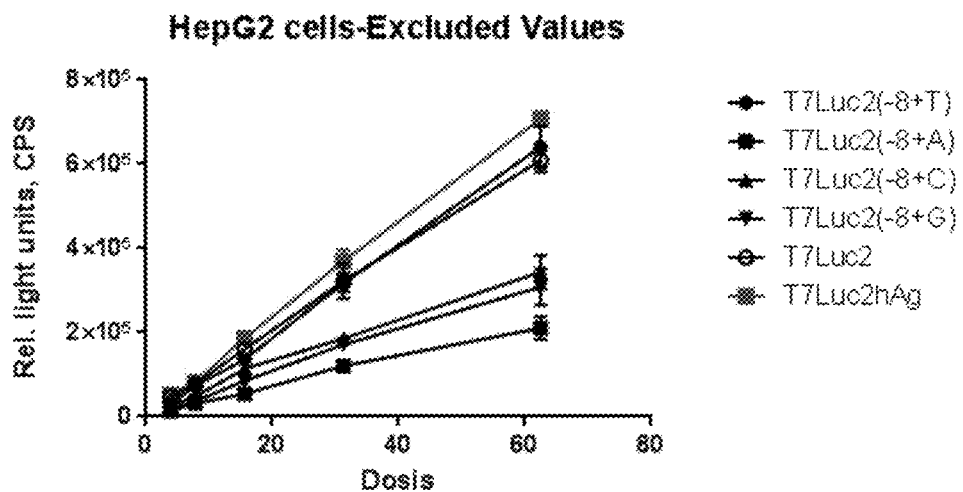
Figure 5A:
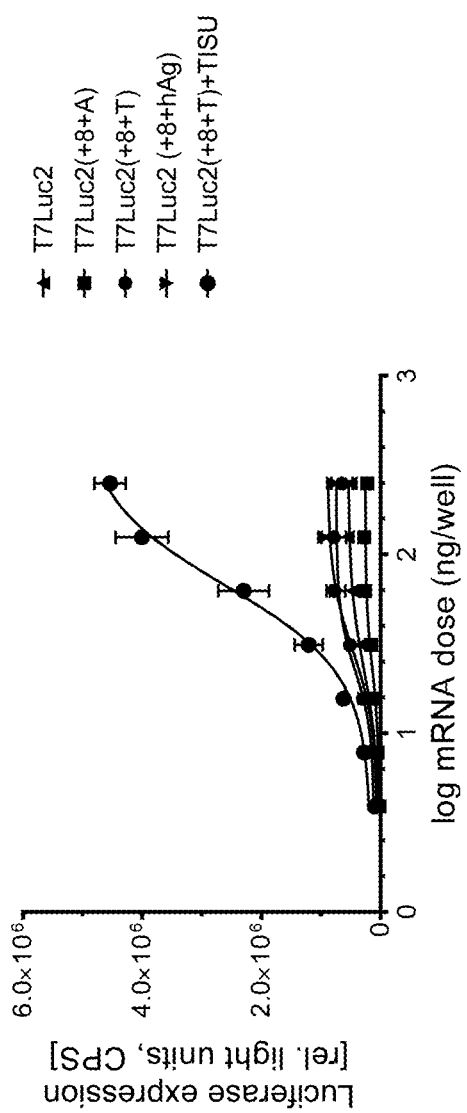
Figure 5B:
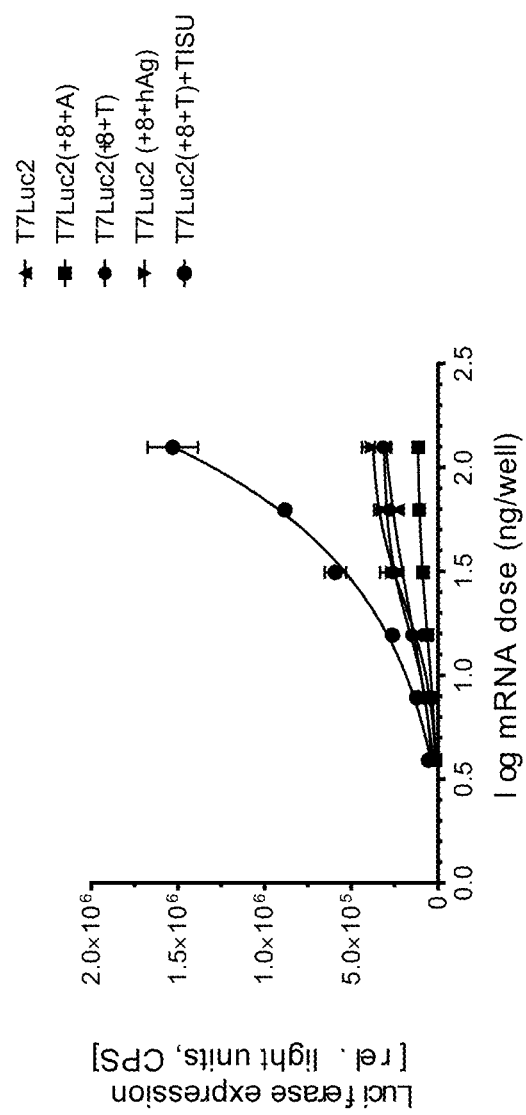
Figure 5C:
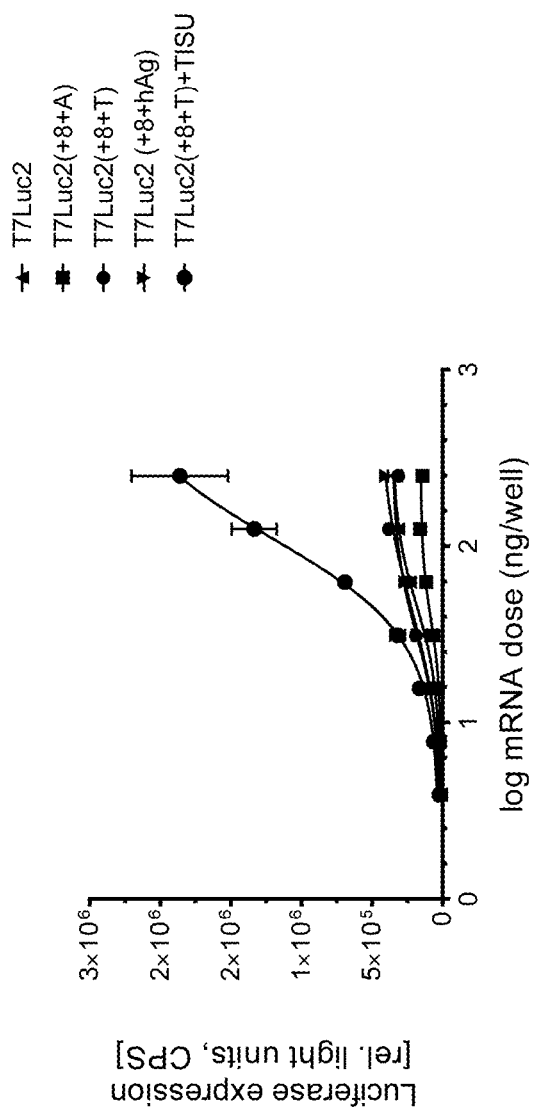
Figure 5D:
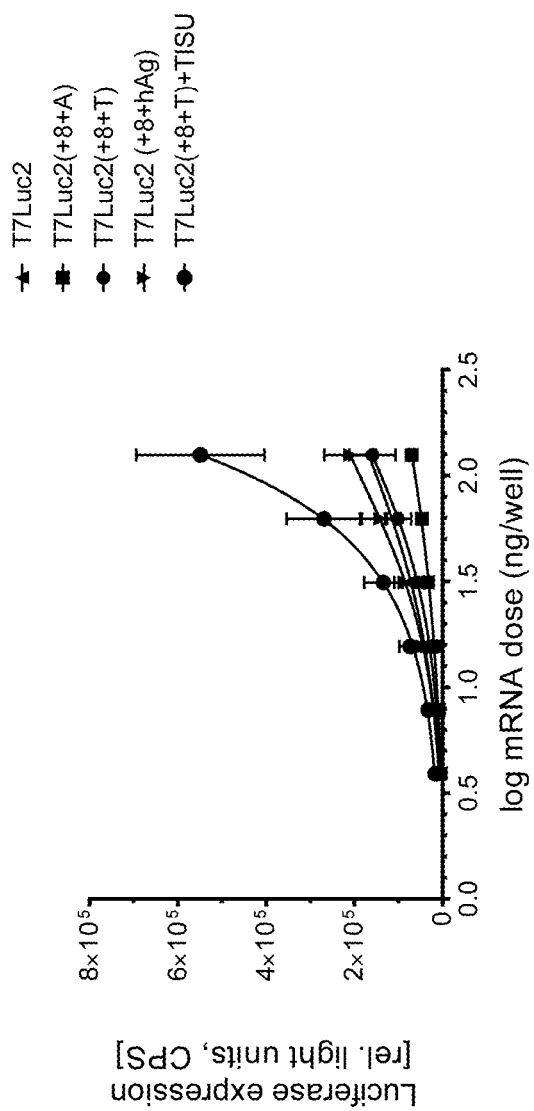

FIG. 4: shows the effect of individual nucleotides as indicated and demonstrates the effect of the distance between the extra "C" and the Kozak element in HepG2 transfected cells. Cells transfected and luciferase assay performed a described under Materials and Methods. As higher doses were out of the linear range, only dose response up to 62.5 ng/well is presented here. Transfection experiments were performed with sequences No. 3-8 from FIG. 1. Hepatocellular carcinoma cell line (HepG2) were seeded at the density of 40,000 cells/well in a 96 well plate. 24 hours post seeding, cells were transfected with different luciferase coding SNIM RNA constructs (sequences No. 3-8 from FIG. 1) using Lipofectamine2000. Luciferase expression was measured at 24 hours post transfection. Values plotted against the transfection dose and data analysed via GraphPad Prism. Values represent mean±SD of 3 replicates. In both cell lines (A549 cells (FIG. 3) and HepG2 (FIG. 4)), insertion of an extra "A" between C and Kozak element (sequence No. 3 from FIG. 1) resulted in significantly lower expression (FIGS. 3 and 4). In both cell types, insertion of a single "T" between C and Kozak element (sequence No. 4 from FIG. 1) resulted in expression levels comparable to that achieved with human alpha globin 5'UTR which was used as a positive control. In HepG2 cells, sequence No. 1 (FIG. 1) was also equally effective.

FIG. 5: shows the effect the TISU element on the expression of luciferase in A549 cells. Detailed dose response and curve fitting was performed for selected luciferase encoding constructs. Based on previous data from FIGS. 2-4, the TISU element was brought into the combination of sequence 4 (FIG. 1) which contained the two desirable attributes: (C between T7 Promoter and Kozak element and extra T between C and Kozak element to achieve sequence No. 9 from FIG. 1).

Human alveolar epithelial cell line (A549) (FIGS. 5 A and B) and human hepatocellular carcinoma cell line (HepG2) (FIGS. 5 C and D) were seeded at the density of 20,000 cells/well and 40,000 cells/well respectively in a 96 well plate. 24 hours post seeding, cells were transfected with different luciferase coding SNIM RNA constructs using Lipofectamine2000. Luciferase expression was measured at 24 and 48 hours post transfection (FIG. 5E). Values plotted against the transfection dose and data analysed via GraphPad Prism. Transfection of A459 (A, B) and HepG2 (C, D) cells with different luciferase coding mRNAs as indicated. Luciferase activity was measured at 24 (A, C) and 48 (B, D) hours post transfection. Values represent mean±SD of 3 replicates.

In both cell lines and at both measured time points, significantly higher expression was obtained with luciferase construct containing TISU element (FIGS. 5A-D).

Figure 6A:
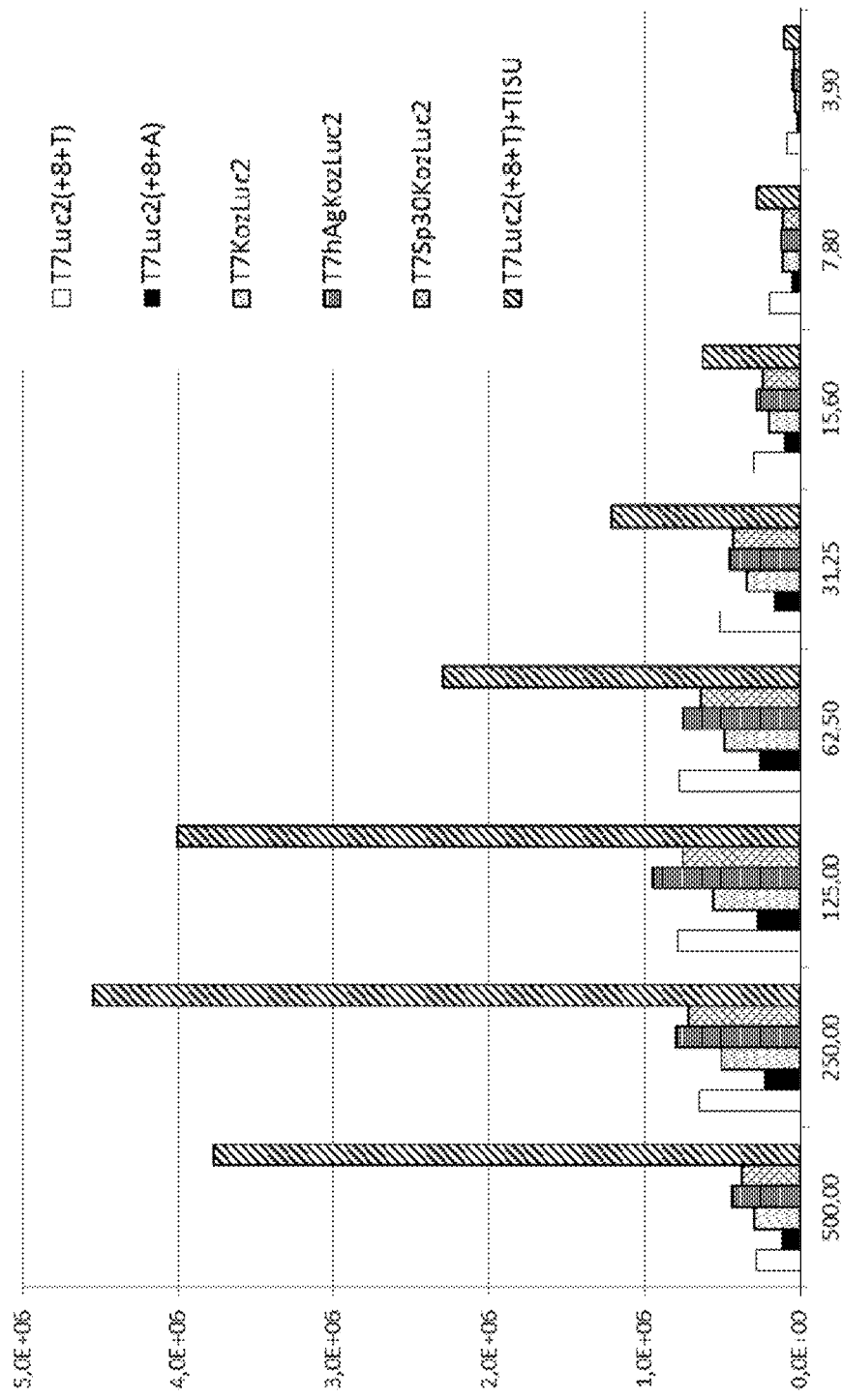
Figure 6B:
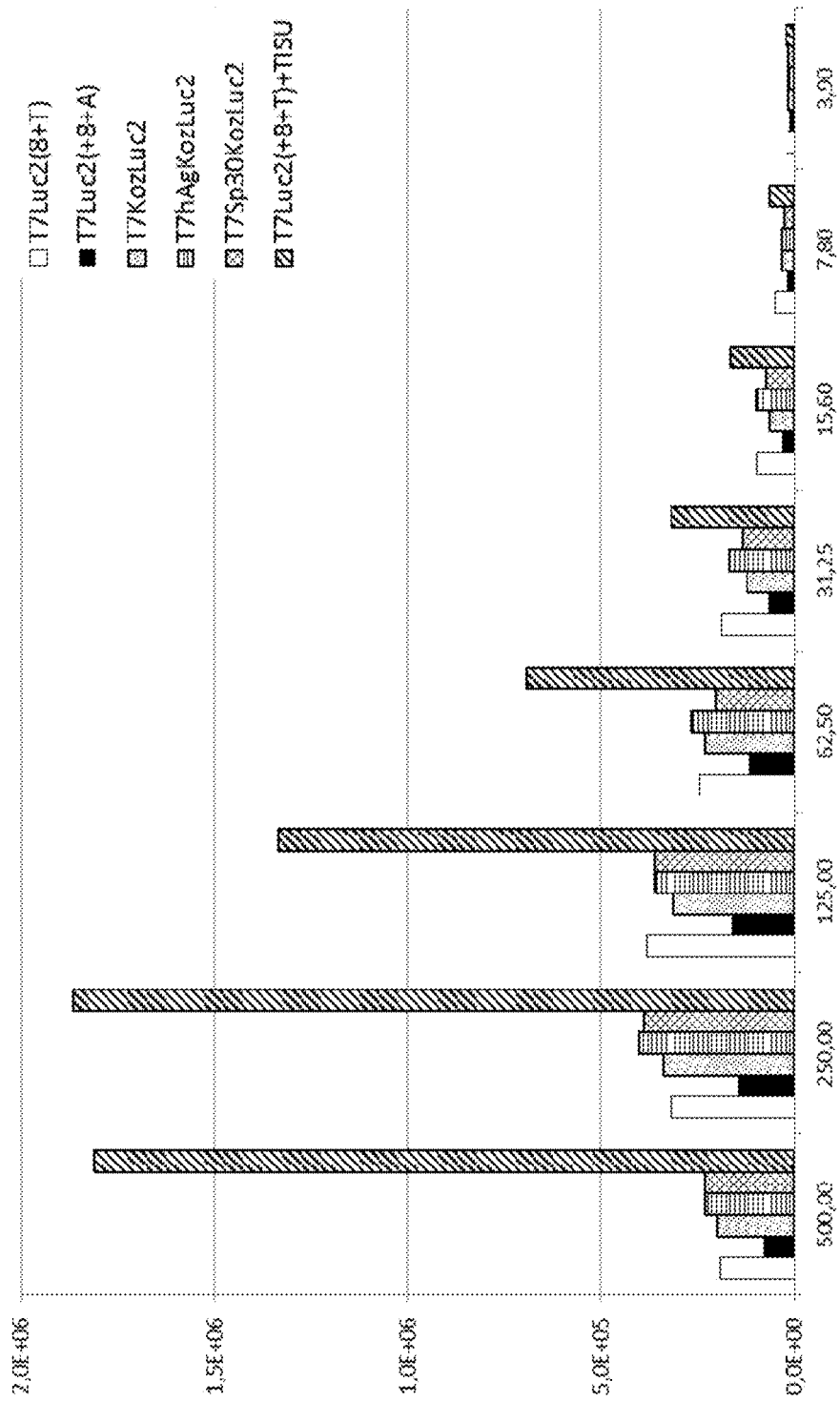

FIG. 6: shows the effect the TISU element on the expression of luciferase in A549 cells (FIG. 6A) and in HepG2 cells (FIG. 6B). Human alveolar epithelial cell line (A549) and human hepatocellular carcinoma cell line (HepG2) were seeded at the density of 20,000 cells/well and 40,000 cells/well respectively in a 96 well plate. 24 hours post seeding, cells were transfected with different luciferase coding SNIM RNA constructs using Lipofectamine2000 (X-axis shows ng amount of SNIM RNA per well of a 96 well plate). Luciferase expression was measured at 24 hours post transfection. Values plotted against the transfection dose and data analysed via GraphPad Prism. Transfection of A549 (A) and HepG2 (B) cells with different luciferase coding mRNAs as indicated.

FIG. 7: shows the results of the in vivo experiments in mice with different Luciferase coding mRNA constructs.

The luciferase constructs as indicated in FIG. 7 (for the respective UTR sequence element see FIG. 1) were tested in vivo in Balb/c mice (female, 6-8 week). For this set of experiment, an additional UTR element which has been shown to enhance transgene expression (International Publication Number WO 2012/170930 A1) was also tested for its efficiency. The Luciferase construct containing this UTR element has been designated as Luc2-SUSA. 20 μg of the respective SNIM-RNA was complexed with LF-44 and injected intravenously into Balb/c mice. In vivo Imaging was performed at 6 hours post injection employing an IVIS imaging system and values quantified as photons/sec/cm$^2$/sr have been plotted. Results from whole animal imaging are shown in FIG. 7A and the results from imaging the whole organ are shown in FIGS. 7B (liver), 7C (lung), 7D (spleen), respectively.

Figure 7A:
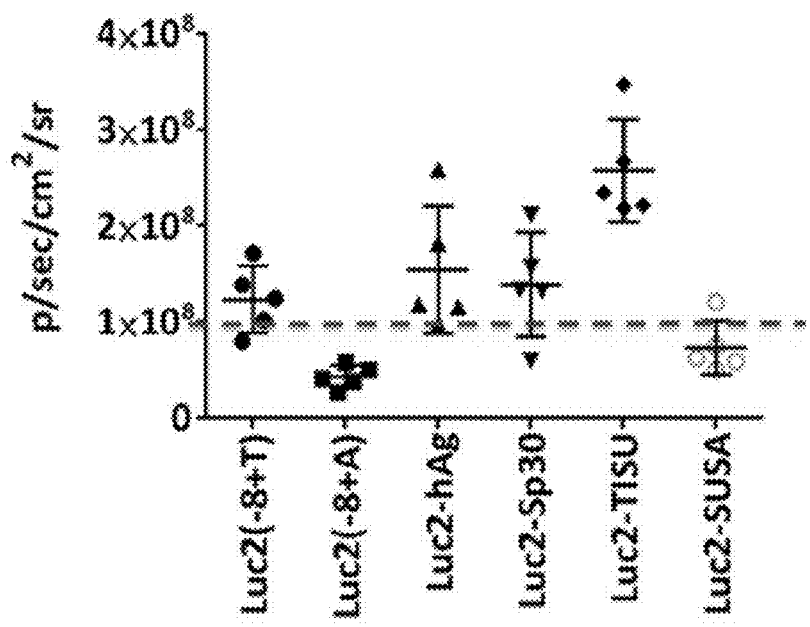
Figure 7B:
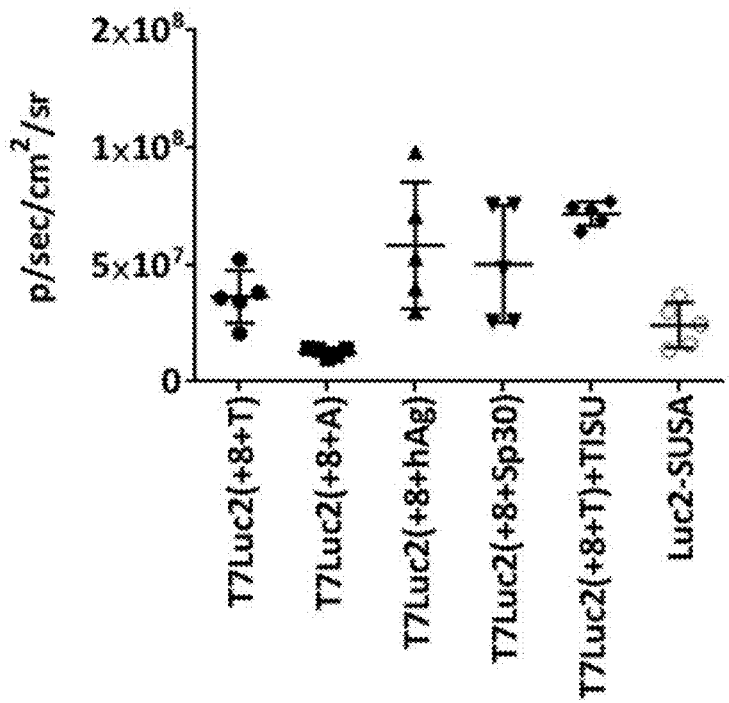
Figure 7C:
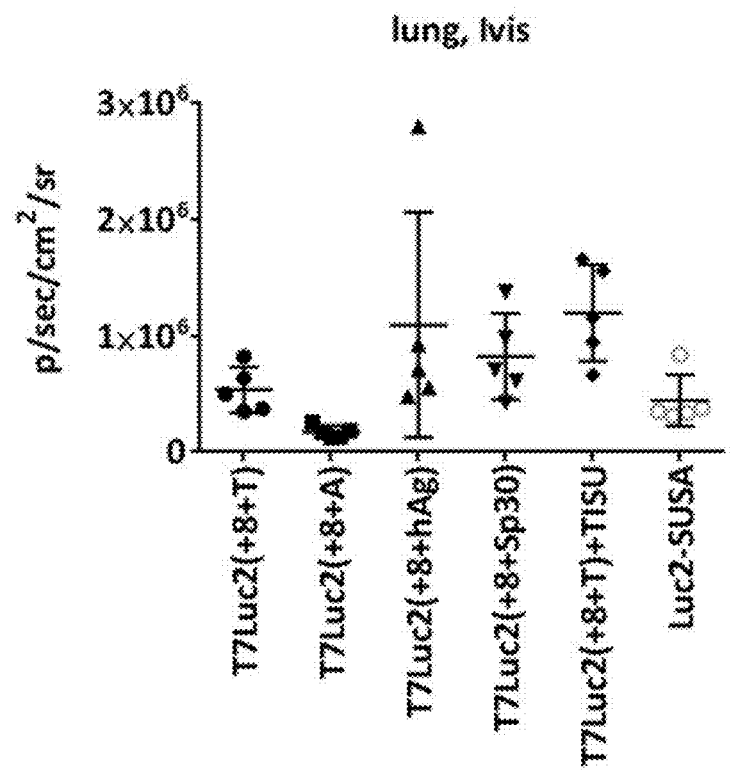
Figure 7D:
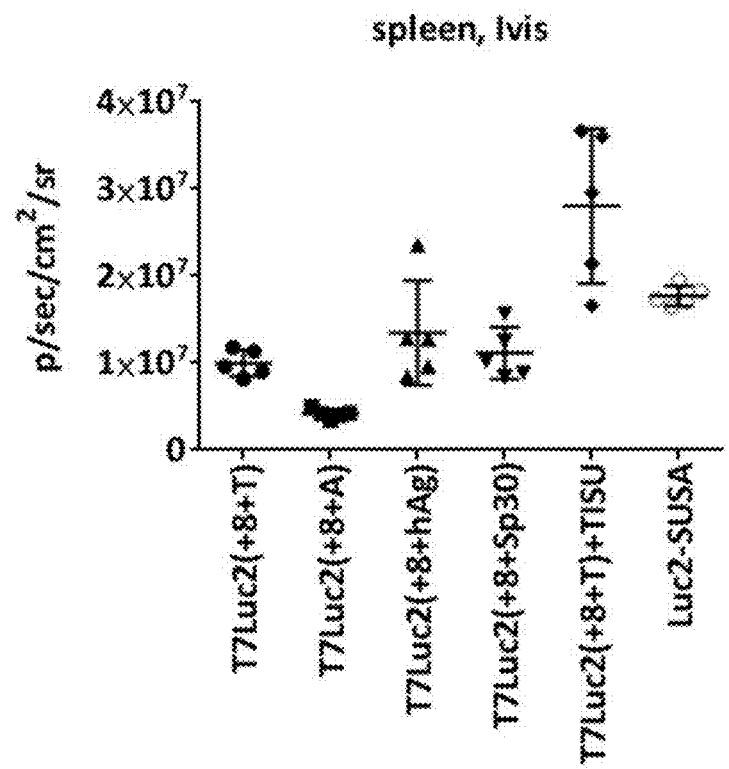
Figure 7E:
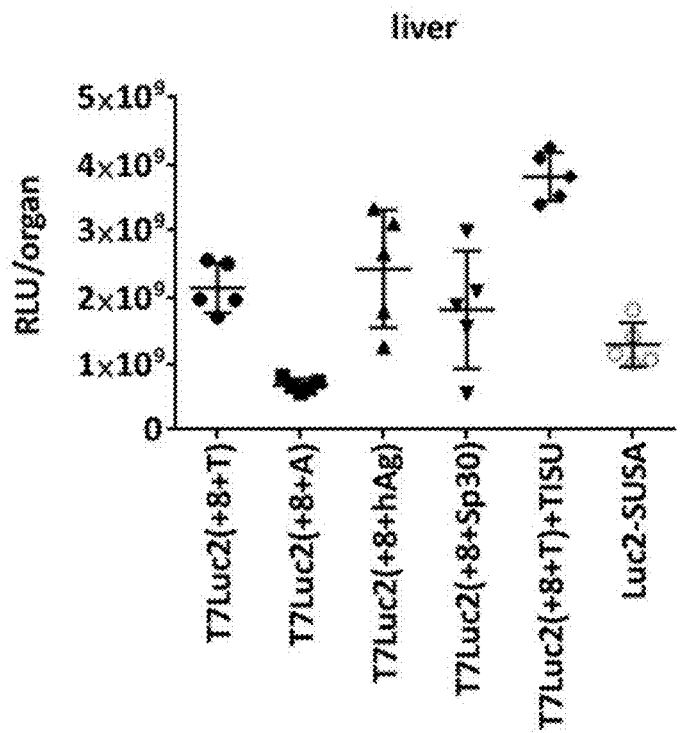
Figure 7F:
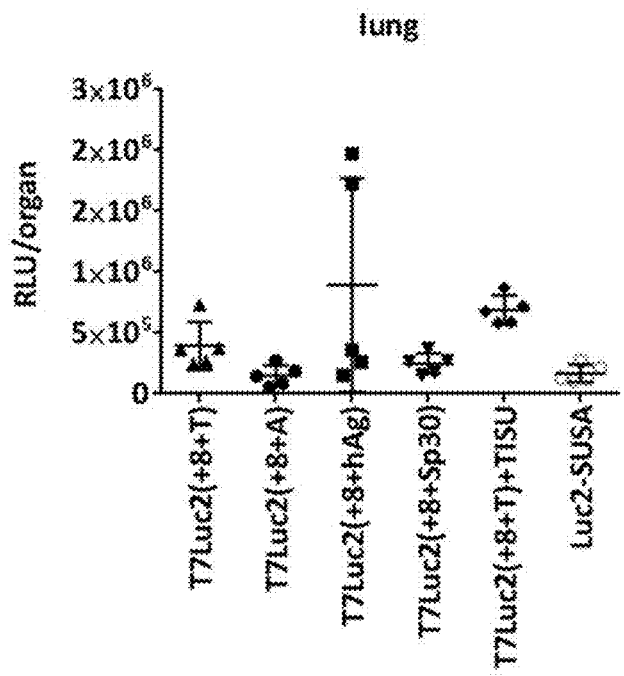
Figure 7G:
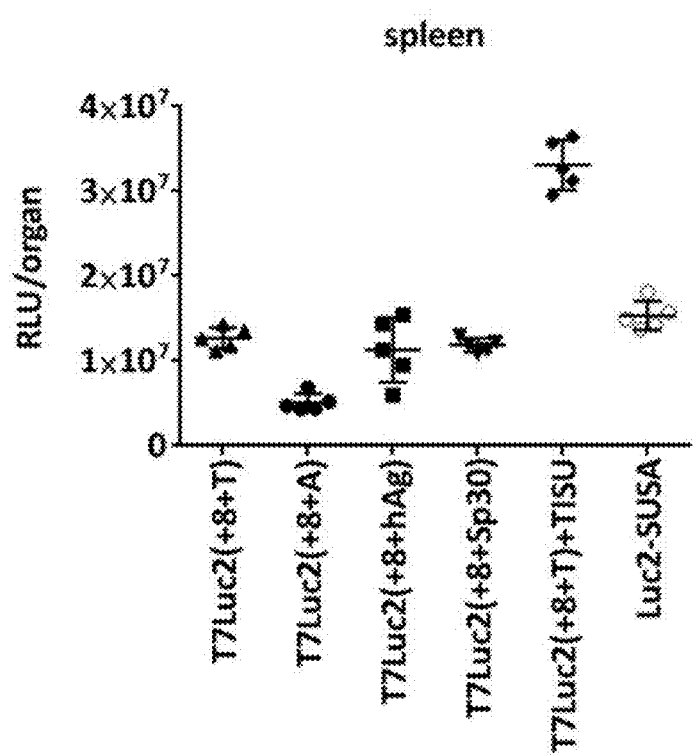
Figure 8A:
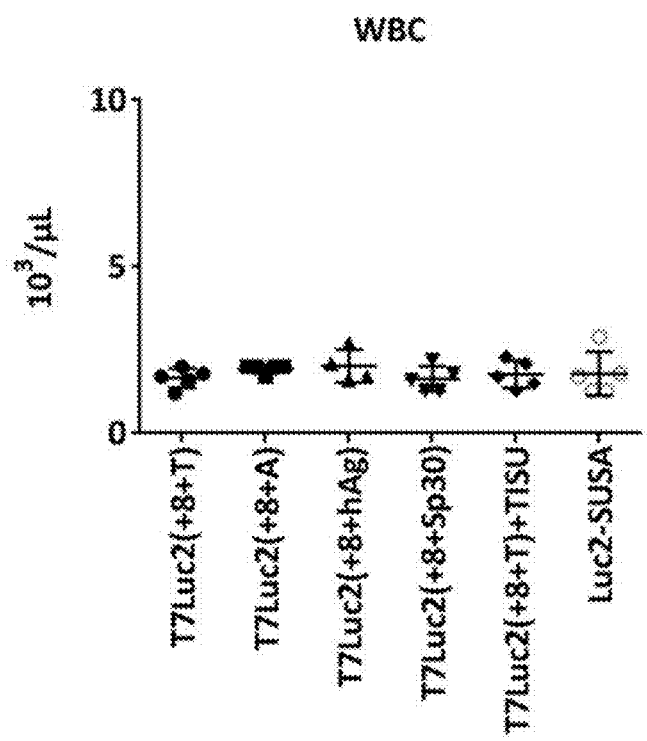
Figure 8B:
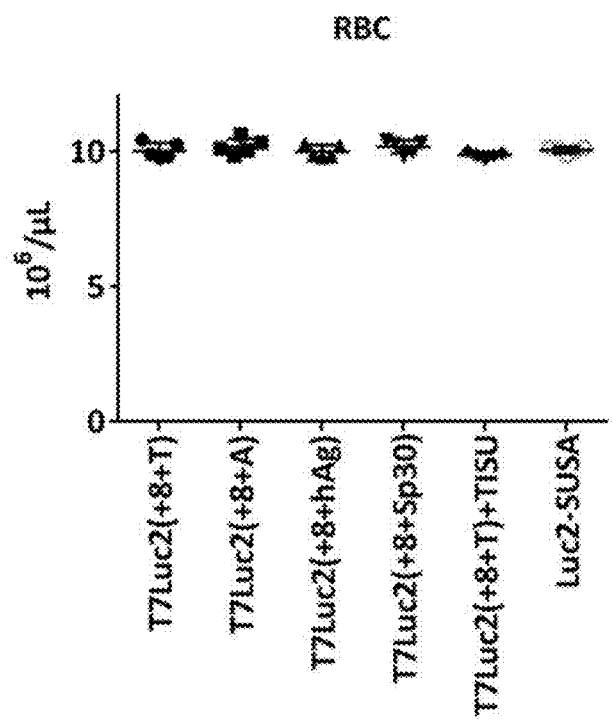
Figure 8C:
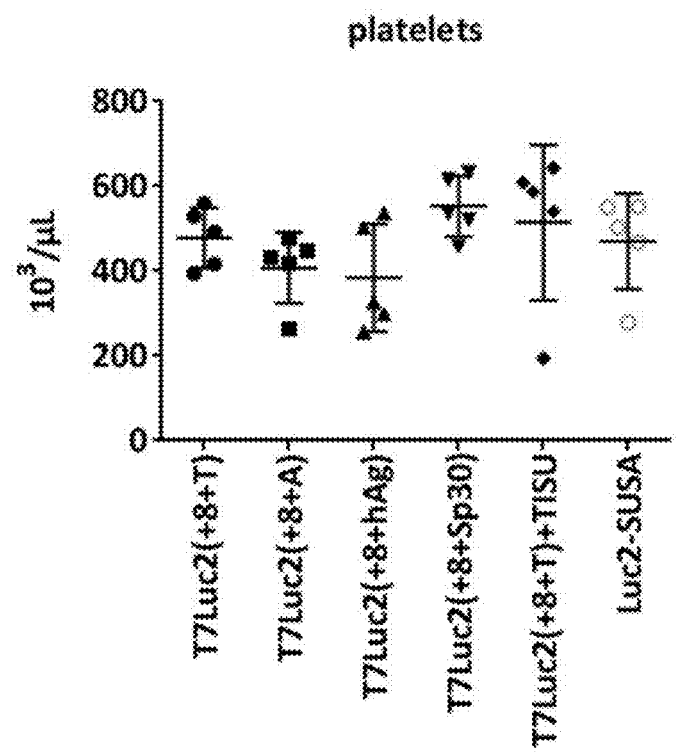
Figure 8D:
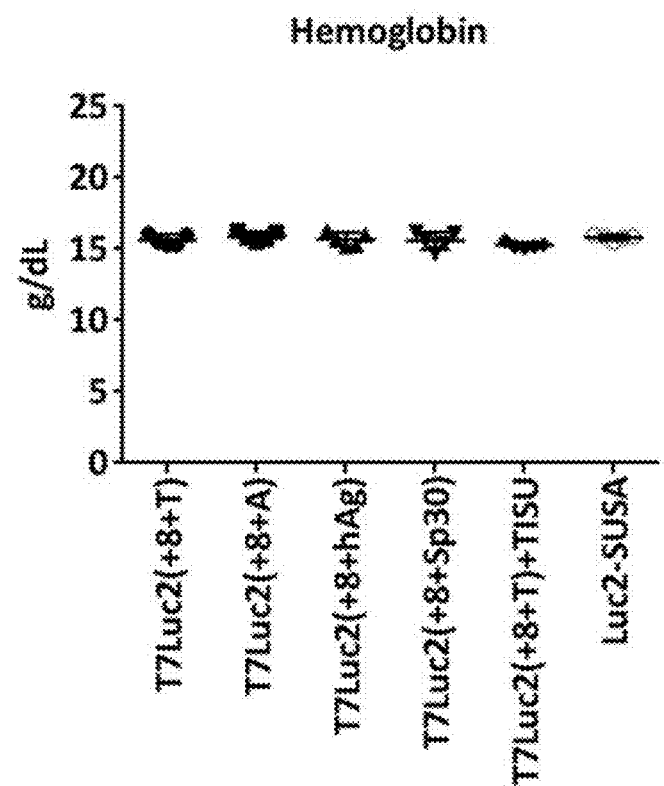
Figure 8E:
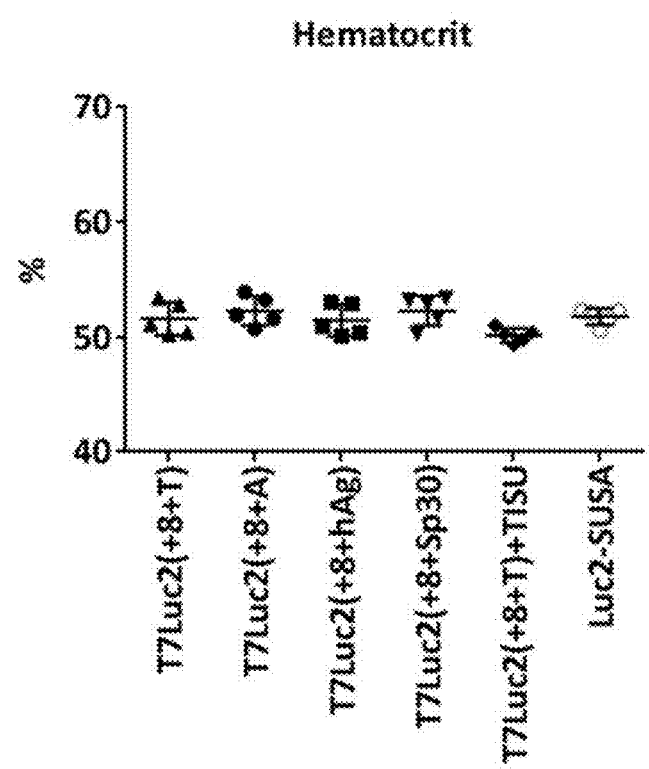

Organs taken from the animals were frozen in liquid nitrogen and homogenized. Cells were lysed in Tris-HCl lysis buffer and luciferase activity was measured. The results are shown in FIGS. 7E (liver), 7F (lung), 7G (spleen), respectively.

Insertion of TISU element resulted in higher expression compared to previously published 5' and 3' UTRs (International Publication Number WO 2012/170930 A1). Addition of a single T between C and Kozak (Sequence No. 4 from FIG. 1) leads to comparable levels of expression observed with human alpha globin UTR (Sequence No. 8 from FIG. 1). Addition of a TISU element, into sequence No. 4 (FIG. 1) further increased the expression (Sequence No. 9 form FIG. 1). It was surprisingly found that the effect of human alpha globin UTR was not found to be sequence specific. A random 30 nucleotide sequence supported similar level of expression as human alpha globin 5'UTR.

Based on in vitro results in cell lines and in vivo experiments in mice, sequences No. 1, 4, 7 and 9 (FIG. 1) are proposed as promising candidates for sequences harbouring "minimal UTRs" for transcript therapy. These minimal UTR sequences have no negative effects on RNA yield during in vitro transcription and the resulting mRNA is much more efficiently translated compared to the mRNAs containing state of the art UTRs.

FIG. 8: shows white blood cells count (WBC) (FIG. 8A), red blood cells (RBC) (FIG. 8B), platelets (FIG. 8C), hemoglobin (FIG. 8D) and hematicrit (FIG. 8E) values from mice with different Luciferase coding mRNA constructs. The experiment was performed essentially as described in FIG. 7 and the blood parameters were analysed by employing a Sysmex KX-21N™ Automated Hematology Analyzer (IL, USA).

Figure 2B:
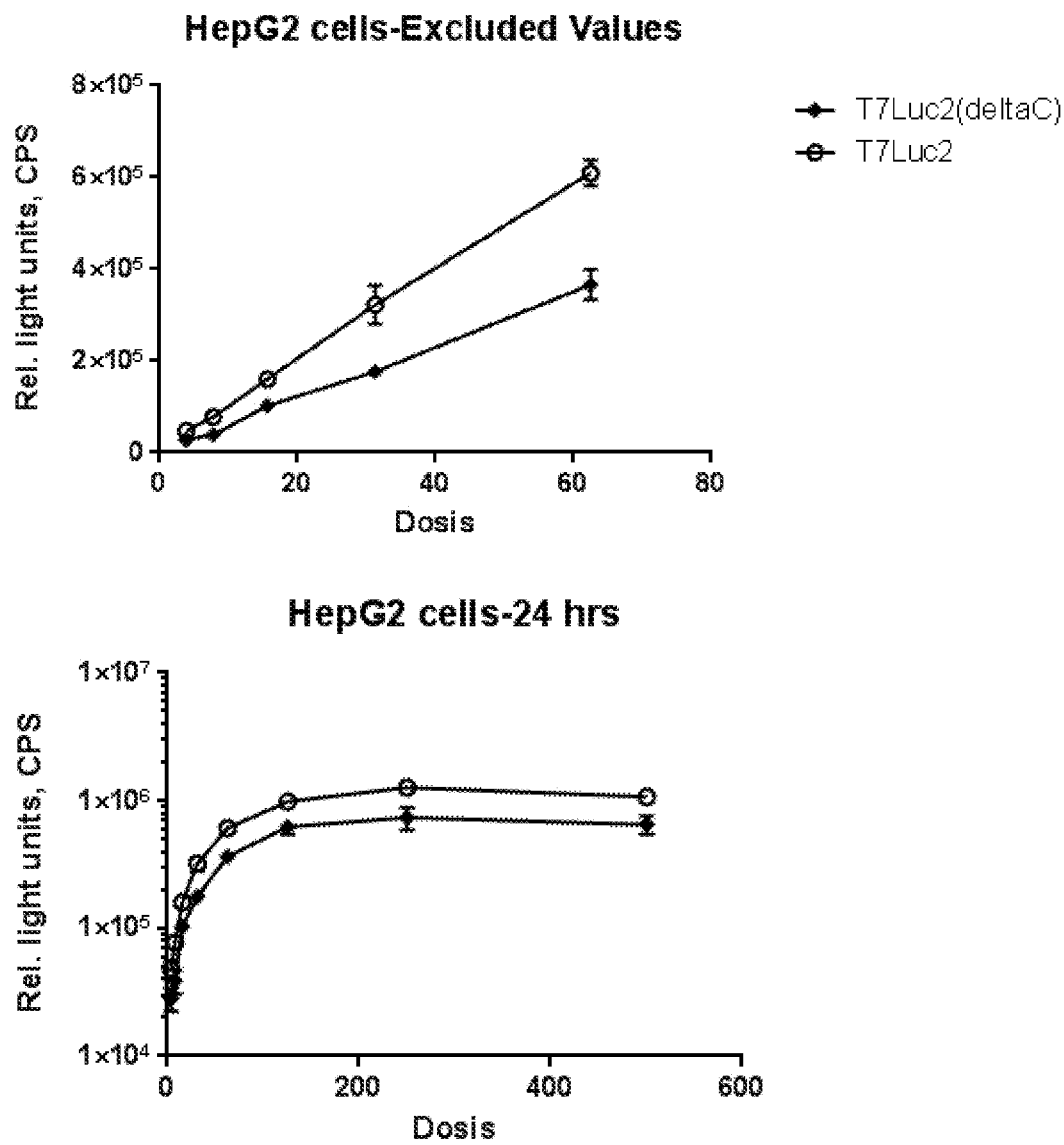

FIG. 9: shows expression experiments with TISU element containing human EPO encoding mRNA in comparison to that from human EPO encoding mRNA containing 5' and 3' UTRs from (International Publication Number WO 2012/170930 A1: FIGS. 1 and 2) (SUSA UTR) which is known to support very high EPO expression.

Human alveolar epithelial cell line (A549) and human hepatocellular carcinoma cell line (HepG2) were seeded at the density of 20,000 cells/well and 40,000 cells/well respectively in a 96 well plate. 24 hours post seeding, cells were transfected with 250 ng of different EPO coding SNIM RNA constructs using Lipofectamine2000. EPO amounts were quantified at 24 hours post transfection via ELISA (Human Erythropoietin Quantikine IVD ELISA Kit from R&D Systems (MN, USA)) and data analysed via GraphPad Prism. Values represent mean±SD of 3 replicates.

FIG. 10: shows expression experiments with human OTC. For human OTC, expression from TISU element containing hOTC encoding mRNA was compared to that from hOTC encoding mRNA containing 5' human alpha globin UTR which is known to yield highest expression compared to all other combinations known thus far.

Human hepatocellular carcinoma cell line (HepG2) were seeded in 96 well plates and 24 hours post seeding, cells were transfected with different hOTC encoding SNIM RNA constructs using Lipofectamine2000. 24 h after transfection, cells were lysed and OTC amounts quantified using Western Blot.

Figure 10A:
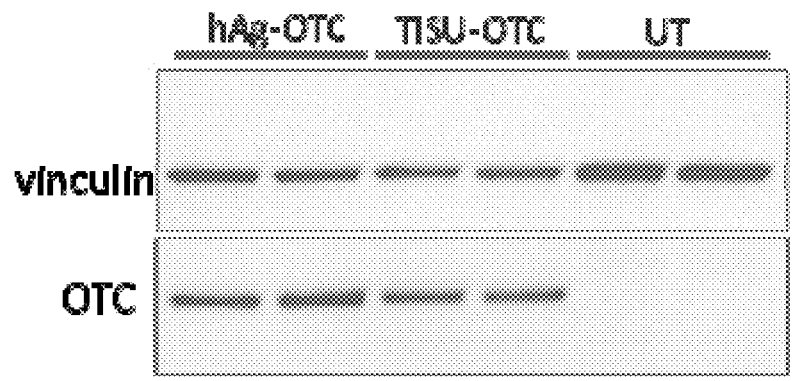
Figure 10B:
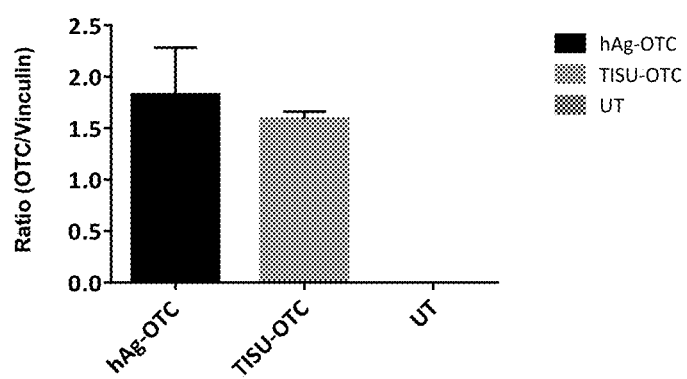

Both hAg and TISU element containing hOTC encoding SNIM RNAs resulted in similar level of hOTC expression (FIG. 10A). Vinculin was used as housekeeper and the band intensities were quantified and used as internal quantification standard (FIG. 10B).

Figure 11:
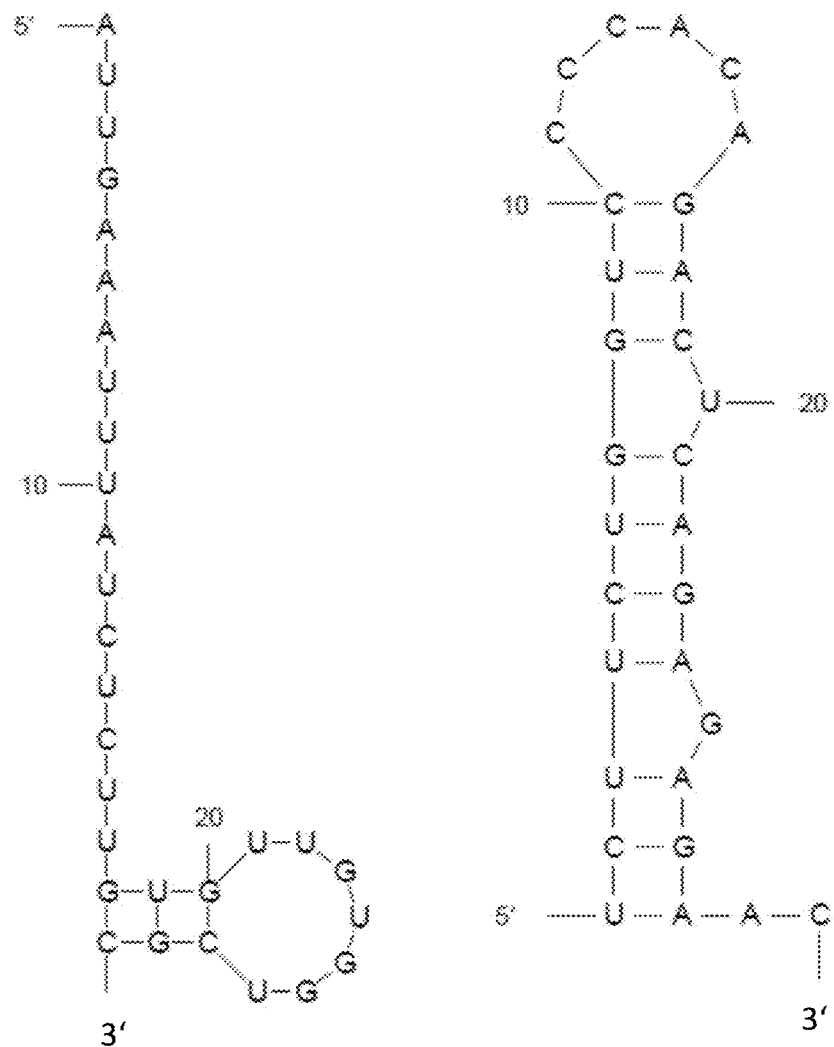

FIG. 11: Predicted secondary structures of a random 30 nucleotide long spacer present in sequence 7 (left) and 5'UTR of human alpha globin present in sequence 8 (right).

Other aspects and advantages of the invention will be described in the following examples, which are given for purposes of illustration and not by way of limitation. Each publication, patent, patent application or other document cited in this application is hereby incorporated by reference in its entirety.

EXAMPLES

I. Materials and Methods

Plasmid Vectors

The respective 5' UTR sequences together with a codon optimized luciferase sequence were synthesized by GeneScriptG (NJ, USA) and cloned in pUC57-Kan (GeneScript). In case of the EPO (codon optimized human erythropoietin) and OTC (codon optimized human ornithine transcarbamylase) the coding sequence luciferase gene was replaced by the coding sequence of the EPO (SEQ ID NO: 35) and the OTC (SEQ ID No: 36) gene, respectively. The UTR sequences used in the constructs together with the name of the respective luciferase reporter construct are shown in FIG. 1.

mRNA Production

To generate in vitro transcribed mRNA (IVT mRNA), plasmids were linearized by BstBI digestion and purified by chloroform extraction and ethanol precipitation. Purified linear plasmids were used as template for in vitro transcription using RiboMax Large Scale RNA production System-T7 (Promega, Germany). Anti-Reverse Cap Analog (ARCA) was added to the reaction mix to generate 5' capped mRNA and mRNA was polyadenylated (Thermo Scientific) to generate the 3' Poly-A tail.

Additionally for the production of SNIM mRNAs, chemically modified nucleotides namely methyl-CTP and thio-UTP (Jena Bioscience, Germany) were added to a final concentration of ATP:CTP:UTP:methyl-CTP:thio-UTP:GTP of 7.57 mM:5.68 mM:5.68 mM:1.89 mM:1.89 mM:1.21 mM. The complete IVT mix was incubated at 37° C. for 2 hours followed by a DNA digestion with DNaseI for 20 minutes at 37° C. RNA was precipitated with ammonium acetate (final concentration 2.5M) and washed with 70% EtOH. The washing step was performed twice. Finally, the RNA pellet was re-suspended in RNAse-free water. All mRNAs were verified on 1% agarose gels. The transcribed RNAs are chemically modified in that about 25% of the uridine residues are 2-thiouridine (s2U) and about 25% of the cytidine residues are 5-methylcytidine (m5C). The sequences of the UTRs are given in FIG. 1.

In Vitro Transfection

Human alveolar epithelial cell line (A549) and human hepatocellular carcinoma cell line (HepG2) were seeded at the density of 20,000 cells/well and 40,000 cells/well respectively in a 96 well plate. 24 hours post seeding, cells were transfected with different luciferase coding SNIM RNA constructs using the commercial transfection reagent Lipofectamine™2000 at a ratio of 2.5 μl Lipofectamine™2000 per 1 μg mRNA (X-axis in FIGS. 2-6 shows ng amount of SNIM RNA per well of a 96 well plate). The complex formation was prepared as follows: Lipofectamine™2000 and mRNA were separately diluted in OptiMEM transfection medium to add up to a total volume of 45 μl, each. These mixtures were incubated at room temperature for 5 minutes. The Lipofectamine™2000 solution was then mixed with the mRNA solution, followed by another 20 minutes of incubation at room temperature. The cells were incubated in a total transfection volume of 90 μl at 37° C. (5% CO2 level) for one hour. The transfection medium was thereafter removed and the cells were washed with PBS. Subsequently, the cells were re-incubated with Leibovitz's L-15 Medium containing 10% FBS.

Cell Culture

A human alveolar adenocarcinoma cell line (A549, ATCC CCL-185) was grown in Ham's F12K medium supplemented with 10% FBS. A human hepato cellular carcinoma cell line (HepG2, ATCC HB-8065) was cultured in DMEM medium, supplemented with 10% fetal bovine serum. All cell lines were grown in a humidified atmosphere at 5% CO2 level.

Bioluminescence Measurement

Firefly Luciferase (FFL) is a common reporter protein that is not endogenously present in mammals and can be detected easily by luminescent imaging. Luciferase catalyses the reaction of luciferin and oxygen which results in bioluminescence emission.

Human alveolar epithelial cell line (A549) and human hepatocellular carcinoma cell line (HepG2) were seeded at the density of 20,000 cells/well and 40,000 cells/well respectively in a 96 well plate. 24 hours post seeding, cells were transfected with different luciferase coding SNIM RNA constructs using Lipofectamine2000 (X-axis shows ng amount of SNIM RNA per well of a 96 well plate). Bioluminescence was measured at 24 hours post transfection. Values plotted against the transfection dose and data analysed via GraphPad Prism.

For quantifying the luciferase expersiion in homogenized tissue lysate, organs were taken from the animals, frozen in liquid nitrogen, homogenized and cells were lysed in lysis buffer (25 mM Tris-HCl pH 7.5 with 0.1% Tritron-X100).

Animals

Six to eight week-old female BALB/c mice were obtained from Janvier, Route Des Chênes SecsBP5, F-53940 Le Genest St. Isle, France, and maintained under specific pathogen-free conditions. Mice were acclimatized to the environment of the animal facility for at least seven days prior to the experiments. All animal procedures were approved and controlled by the local ethics committee and carried out according to the guidelines of the German law of protection of animal life.

Lipidoid Formulations

Lipidoids were formulated with mRNA as follows: C12-(2-3-2), DOPE, Chol and DSPE-PEG2k (3.6:0.18:0.76:1 weight ratio) were dissolved in ethanol and rapidly injected into a citrate-buffered solution (10 mM citric acid, 150 mM NaCl, pH=4.5) comprising chemically modified mRNA encoding firefly luciferase at an lipid/mRNA weight ratio of 10.5 to yield a final ethanol concentration of 20% and dialized against water. The resulting lipidoid/mRNA complexes resulted in positively charged nanoparticles (92.6±0.7 nm; 21.0±0.2 mV) and were injected intravenously into the tail vein of restrained mice. In a second experiment, the lipidoid/mRNA complexes were adjusted to PBS before intravenous injection which resulted in nearly uncharged nanoparticles (91.5±0.6 nm; −0.7±0.2 mV).

Measurement of Luc Activity in Mice Using In Vivo Bioluminescent Imaging

Twenty-four hours post administration mice were anaesthetized by intraperitoneal injection of medetomidine (11.5 µg/kg BW), midazolame (115 µg/kg BW) and fentanyl (1.15 µg/kg BW). D-luciferin substrate (3 mg/100 µl PBS per mouse) was applied via intravenous injection. Bioluminescence was measured 10 minutes later, using an IVIS 100 Imaging System (Xenogen, Alameda, USA) and the camera settings: Bin(HS), field of view 10, f1 f-stop, high-resolution binning and exposure-time of 5 min. The signal was quantified and analyzed using the Living Image Software version 2.50 (Xenogen, Alameda, USA).

Western Blot Analysis of OTC Protein

Frozen plates were thawed and direct cell lysis in the plate was performed. Proteins were lysed using lysis buffer (25 mM TRIS, 0.1% Triton-X 100, Sigma-Aldrich, Germany) complemented with protease inhibitor (cOmplete, EDTA-free, Roche Diagnostics, Germany) and DNase (DNase I Solution (2500 U/mL), (Thermo Fisher, USA). After lysis the samples were mixed with NuPage® LDS Sample Buffer and Sample Reducing Agent (Thermo Fisher, USA) and heated for 10 min at 70° C. Gel electrophoresis was conducted using 15 µL of the lysate on NuPAGE 10% Bis-Tris Midi Gels with the XCell4 SureLock™ Midi, Bio-Rad Criterion™ System (Thermo Fisher, USA). Proteins were transferred using the TransBlot® Turbo™ Transfer System (Biorad, Germany) for 30 min. After the transfer the membranes were blocked with NET-gelatine for 30 min before the membrane were incubated overnight at 4° C. with the primary antibody, diluted in NET-gelatine 1:2000 (OTC Polyclonal Antibody (Center), AP6928c-AB Biocat, Germany). After three washing steps with NET-gelatine, horseradish peroxidase-conjugated secondary antibody (goat anti-rabbit IgG-HRP, sc-2004, Santa Cruz Biotechnology, USA), diluted 1:10,000 in NET-gelatine, was added for 1 h at RT. The membrane was washed again three times with NET-gelatine until signals were visualized with a chemiluminescent substrate kit (Luminata Crescendo Western HRP substrate, Merck Millipore, Germany) and visualized using the ChemiDoc™ MP System (Biorad, Germany).

Materials

FBS, Leibovitz's L-15 Medium (Gibco), Lipofectamine™2000, and OptiMEM (Gibco) were purchased from Invitrogen, Germany. Sterile PBS was prepared in-house. Ham's F-12K, DMEM, and Trypsin-EDTA were purchased from c.c.pro GmbH, Germany.

II. Results

II.a Cell Culture Experiments

FIGS. 2A and B shows that the extra "C" between the T7 Promoter and Kozak element is essential. Deleting that base results in reduced expression in both of the compared cell types. For both constructs (Sequence No. 1 and 2 from FIG. 1), the entire dose range and linear range (excluded values: dosis higher than 62.5 ng/well excluded from analysis) are presented separately for convenience of comparison. In both A549 and HepG2 cells, deletion of C resulted in lower expression. Therefore this extra C was included in the design of all further constructs.

Based on the results obtained in A549 and HepG2 cells, further experiments were conducted with the construct containing the extra "C" (Sequence number 1: T7Luc2).

FIG. 3 and FIG. 4.

Sequence 1 was used as template and to this sequence, either a single nucleotide (A, T, G or C: sequence numbers 3-6 from FIG. 1, respectively), or a random sequence, 30 nucleotide long and devoid of any predictable secondary structure (sequence 7) or 5' UTR from human alpha globin (sequence 8) was incorporated between the investigated "C" and Kozak element.

Cells were transfected and luciferase assay has been performed a described under Materials and Methods. As higher doses were out of the linear range, only dose response up to 62.5 ng/well is presented here. 5'UTR from human alpha globin was used as positive control.

To summarize the above results, FIGS. 1 to 4 show that an extra "C" between the T7 Promoter and Kozak element is essential with respect to achieving high protein expression by employing a minimalistic 5'UTR. Deleting the nucleotide results in reduced expression. The addition of an extra "A" between the extra "C" and Kozak element negatively affects expression. When a pyrimidine base and most preferably a "T" is added at that position, levels comparable to those observed with 5'UTR from hAg are obtained.

Subsequently, additional Experiments were performed to:
  elucidate the effect of TISU element when combined with the best working sequence (Sequence 9), and
  determine whether the effect of 5' UTR from hAg is a sequence specific effect or whether is the distance between 5'Cap and start codon important.

FIG. 5 shows the effect of the TISU element on the expression of luciferase in A549 cells. The "TISU element" incorporates "AG" instead of "CC" in Sequence No. 9 as shown in FIG. 1 vis-à-vis Sequence No. 4 as shown in FIG. 1. A549 cells (FIGS. 5A and B) as well as HepG2 cells (FIGS. 5C and D) showed significantly higher luciferase expression with the luciferase construct containing TISU element together with the "C" from Sequence No 1 and the additional "T" between this "C" and the Kozak element at 24 (A, C) and 48 (B, D) hours post transfection.

FIG. 6 shows the results from the same experiment as from FIG. 5 but with the addition of a 5'UTR containing a 30 nucleotide random sequence, to allow a side by side comparison of the human alpha globin UTR (Sequence 8 from FIG. 1) with a random sequence of the same length (Sequence 7 from FIG. 1) Luciferase expression was measured in HepG2 (FIG. 6A and A549 cells (FIG. 6B) 24 hours after transfection with the SNIM RNAs as indicated.

FIG. 9 shows the results from expression experiments with TISU element containing hEPO encoding mRNA in comparison to that from hEPO encoding mRNA containing 5' and 3' UTRs from (International Publication Number WO 2012/170930 A1: FIGS. 1 and 2) (SUSA UTR) which was used as a standard after transfection of A549 and HepG2 cells with the respective SNIM RNA. EPO amounts were quantified at 24 hours post transfection via ELISA. Values represent mean±SD of 3 replicates.

Figure 9A:
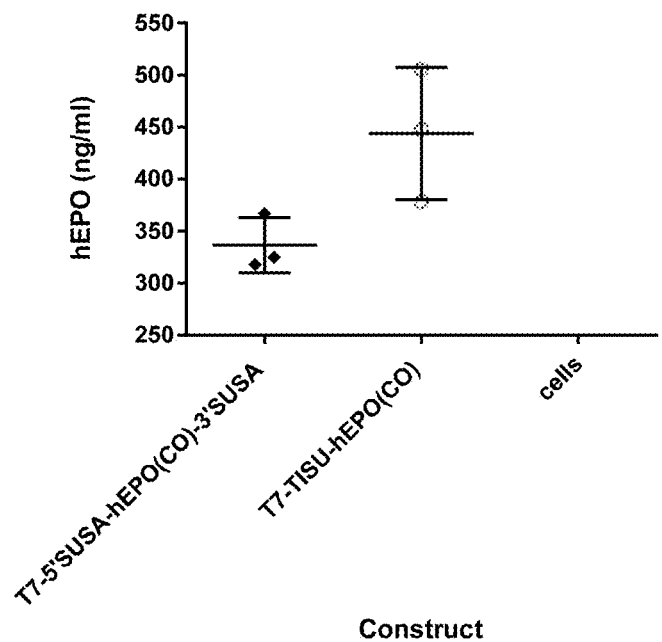
Figure 9B:
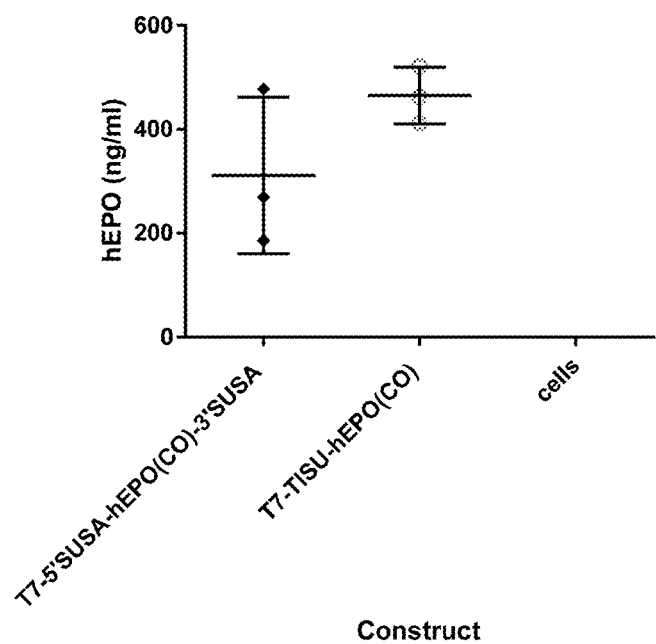

In human A549 cells, incorporation of the TISU element resulted in higher expression compared to that achieved with incorporation of 5' and 3' UTRs (FIG. 9A). Comparable levels of expression were observed in HepG2 cells (FIG. 9B). This is especially surprising as the incorporation of the SUSA 5' and 3' UTRs makes the RNAs about 200 nucleotides longer compared to the UTR according to the present invention.

FIG. 10 shows expression experiments with human OTC. For comparison TISU element containing hOTC encoding mRNA was compared to that from hOTC encoding mRNA containing 5' human alpha globin UTR which is known to yield highest expression compared to all other combinations known thus far. HepG2 cells were transfected with different hOTC encoding SNIM RNA constructs, lysed 24 hours later and OTC amounts quantified by Western blotting.

Both hAg and TISU element containing hOTC encoding SNIM RNAs resulted in similar level of hOTC expression (FIG. 10A). Vinculin was used as housekeeper and the band intensities were compared using densitometry (FIG. 10B).

II.b IV Application of Luc2 Constructs in Mice

The results are shown in FIG. 7 and FIG. 8.

The following constructs have been used in IV applications in mice:
Luc2 (+8+A)
Luc2 (+8+T)
Luc2 (+8+T)+TISU
Luc2-hAg
Luc2-Sp30
Luc2-SUSA UTRs 20 μg of the respective SNIM-RNA was complexed with LF-44 and injected IV into Balb/c mice. As an additional control, Luc2 sequence flanked by human CMV enhancer at Fend (Luc2-SUSA) and human growth hormone 3'UTR at the Tend was also produced. The sequences used as UTRs in this construct have been taken from the Shire Patent (WO 2012/170930 A1: Sequence ID 1/FIG. 1.)

In vivo Imaging was performed at 6 hours post injection employing an IVIS imaging system and values quantified as photons/sec/cm2/sr have been plotted. Results from whole animal imaging are shown in FIG. 7A and the results from imaging the whole organ are shown in FIGS. 7B (liver), 7C (lung), 7D (spleen), respectively.

Organs taken from the animals were frozen in liquid nitrogen, homogenized, lysed, and luciferase activity was measured. The results are shown in FIGS. 7E (liver), 7F (lung), 7G (spleen), respectively.

Blood parameters of the animals were analyzed by employing a Sysmex KX-21N™ Automated Hematology Analyzer: white blood cells count (WBC) (FIG. 8A), red blood cells (RBC) (FIG. 8B), platelets (FIG. 8C), hemoglobin (FIG. 8D) and hematocrit (FIG. 8E) values from mice with different Luciferase coding mRNA constructs do not show significant differences.

FIG. 11: Predicted secondary structures of a random 30 nucleotide long spacer present in sequence 7 (left) and 5'UTR of human alpha globin of the same length present in sequence 8 (right). Although the secondary structures of both sequences are not even similar, they resulted in similar expression levels (FIGS. 6A and 6B) which were both equally low in comparison to the T7Luc2(+8+T)–TISU.

---

The invention claimed is:

1. A DNA molecule, which can be transcribed into an mRNA, comprising one strand with the following elements:
   (a) a coding region, including a start codon at its 5' end, coding for a polypeptide; and
   (b) directly upstream of said coding region a sequence $R_1$ directly linked to CNGCCACC (SEQ ID NO:2), wherein the nucleotide N at position 2 of SEQ ID NO:2 is T, wherein $R_1$ is a promoter which is recognized by a DNA-dependent RNA-polymerase;
   or comprising a complementary strand of said DNA strand,
   wherein the promoter which is recognized by a DNA-dependent RNA polymerase is selected from the group consisting of:
   (i) TAATACGACTCACTATAGGGAGA (SEQ ID NO: 3) which is recognized by a T7 DNA-dependent RNA polymerase;
   (ii) AATTAACCCTCACTAAAGGGAGA (SEQ ID NO: 4) which is recognized by a T3 DNA-dependent RNA polymerase;
   (iii) ATTTAGGTGACACTATAGAAG (SEQ ID NO: 5) which is recognized by a SP6 DNA-dependent RNA polymerase; and
   (iv) AATTAGGGCACACTATAGGGA (SEQ ID NO: 6) which is recognized by a K11 DNA-dependent RNA polymerase.

2. A vector comprising the DNA molecule of claim 1.

3. A host cell comprising the vector of claim 2.

4. A composition comprising:
the DNA molecule of claim 1.

5. An RNA molecule comprising
(a) a coding region, including a start codon at its 5' end, coding for a polypeptide; and
(b) directly upstream of said coding region a UTR of the sequence $R_2$-CNGCCACC (SEQ ID NO:2), wherein the nucleotide N at position 2 of SEQ ID NO:2 is U, wherein $R_2$ is an RNA sequence corresponding to the part of a promoter region starting with the nucleotide where a DNA-dependent RNA-polymerase initiates RNA synthesis,
wherein $R_2$ is selected from the group consisting of:

(i)
GGGAGA;  (SEQ ID NO: 7)

(ii)
GGGAGA;  (SEQ ID NO: 8)

(iii)
GAAG;  (SEQ ID NO: 9)
and (iv)
GGGA;  (SEQ ID NO: 10)

and
wherein the RNA molecule comprises a poly-A tail at the 3' end having a length of at least 120 nucleotides;
wherein the UTR as defined in (b) has a maximal length of 14 nucleotides when $R_2$ is (i) or (ii); or
wherein the UTR as defined in (b) has a maximal length of 12 nucleotides when $R_2$ is (iii) or (iv).

6. A nucleic acid molecule encoding the RNA molecule of claim 5.

7. A vector comprising the nucleic acid molecule of claim 6.

8. A host cell comprising the vector of claim 7.

9. A pharmaceutical composition comprising the RNA molecule of claim 5.

10. The pharmaceutical composition of claim 9 for use in RNA-based therapies.

11. A kit comprising the DNA molecule of claim 1.

12. A method of translating a coding region of an RNA molecule into a polypeptide or a protein encoded by said coding region using an UTR as defined in claim 5.

* * * * *

SEQUENCE LISTING

```
<160> NUMBER OF SEQ ID NOS: 45

<210> SEQ ID NO 1
<211> LENGTH: 7
<212> TYPE: DNA
<213> ORGANISM: Artificial Sequence
<220> FEATURE:
<221> NAME/KEY: source
<222> LOCATION: 1..7
<223> OTHER INFORMATION: /mol_type="unassigned DNA"
      /note="Minmal UTR1"
      /organism="Artificial Sequence"

<400> SEQUENCE: 1 cgccacc                                                              7

<210> SEQ ID NO 2
<211> LENGTH: 8
<212> TYPE: DNA
<213> ORGANISM: Artificial Sequence
<220> FEATURE:
<221> NAME/KEY: source
<222> LOCATION: 1..8
<223> OTHER INFORMATION: /mol_type="unassigned DNA"
      /note="Minimal UTR2"
      /organism="Artificial Sequence"
<220> FEATURE:
<221> NAME/KEY: variation
<222> LOCATION: 2
<223> OTHER INFORMATION: /replace="A"
      /replace="T"
      /replace="C"
      /replace="G"

<400> SEQUENCE: 2 cngccacc                                                             8

<210> SEQ ID NO 3
```

```
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="T7 promoter"
      /organism="Artificial Sequence"

<400> SEQUENCE: 3
taatacgact cactataggg aga                                         23

<210> SEQ ID NO 4
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="T3 promoter"
      /organism="Artificial Sequence"

<400> SEQUENCE: 4
aattaaccct cactaaaggg aga                                         23

<210> SEQ ID NO 5
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="SP6 promoter"
      /organism="Artificial Sequence"

<400> SEQUENCE: 5
atttaggtga cactatagaa g                                           21

<210> SEQ ID NO 6
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="K11 promoter"
      /organism="Artificial Sequence"

<400> SEQUENCE: 6 aatagggca cactataggg a                                            21

<210> SEQ ID NO 7
<211> LENGTH: 6
<212> TYPE: DNA
<213> ORGANISM: Artificial Sequence
<220> FEATURE:
<221> NAME/KEY: source
<222> LOCATION: 1..6
<223> OTHER INFORMATION: /mol_type="unassigned DNA"
      /note="T7 promoter"
      /organism="Artificial Sequence"

<400> SEQUENCE: 7 gggaga                                                             6
```

-continued

```
<210> SEQ ID NO 8
<211> LENGTH: 6
<212> TYPE: DNA
<213> ORGANISM: Artificial Sequence
<220> FEATURE:
<221> NAME/KEY: source
<222> LOCATION: 1..6
<223> OTHER INFORMATION: /mol_type="unassigned DNA"
      /note="T3 promoter"
      /organism="Artificial Sequence"

<400> SEQUENCE: 8 gggaga                                                                    6

<210> SEQ ID NO 9
<211> LENGTH: 4
<212> TYPE: DNA
<213> ORGANISM: Artificial Sequence
<220> FEATURE:
<221> NAME/KEY: source
<222> LOCATION: 1..4
<223> OTHER INFORMATION: /mol_type="unassigned DNA"
      /note="SP6 promoter"
      /organism="Artificial Sequence"

<400> SEQUENCE: 9 gaag                                                                      4

<210> SEQ ID NO 10
<211> LENGTH: 4
<212> TYPE: DNA
<213> ORGANISM: Artificial Sequence
<220> FEATURE:
<221> NAME/KEY: source
<222> LOCATION: 1..4
<223> OTHER INFORMATION: /mol_type="unassigned DNA"
      /note="K11 promoter"
      /organism="Artificial Sequence"

<400> SEQUENCE: 10 ggga                                                                      4

<210> SEQ ID NO 11
<211> LENGTH: 16
<212> TYPE: RNA
<213> ORGANISM: Artificial Sequence
<220> FEATURE:
<221> NAME/KEY: source
<222> LOCATION: 1..16
<223> OTHER INFORMATION: /mol_type="unassigned RNA"
      /note="Reverse complementary sequence of minimal UTR1"
      /organism="Artificial Sequence"

<400> SEQUENCE: 11
caugguggcg ucuccc                                                        16

<210> SEQ ID NO 12
<211> LENGTH: 17
<212> TYPE: RNA
<213> ORGANISM: Artificial Sequence
<220> FEATURE:
<221> NAME/KEY: source
<222> LOCATION: 1..17
<223> OTHER INFORMATION: /mol_type="unassigned RNA"
      /note="Reverse complementary sequence of minimal UTR2"
      /organism="Artificial Sequence"
<220> FEATURE:
<221> NAME/KEY: variation
<222> LOCATION: 10
<223> OTHER INFORMATION: /replace="G"
      /replace="C"
```

/replace="U"
　　　/replace="A"

<400> SEQUENCE: 12
cauggugscn gucuccc                                               17

<210> SEQ ID NO 13
<211> LENGTH: 16
<212> TYPE: RNA
<213> ORGANISM: Artificial Sequence
<220> FEATURE:
<221> NAME/KEY: source
<222> LOCATION: 1..16
<223> OTHER INFORMATION: /mol_type="unassigned RNA"
　　　/note="Reverse complementary sequence of minimal UTR1 including
　　　TISU element"
　　　/organism="Artificial Sequence"

<400> SEQUENCE: 13
caucuuggcg ucuccc                                                16

<210> SEQ ID NO 14
<211> LENGTH: 17
<212> TYPE: RNA
<213> ORGANISM: Artificial Sequence
<220> FEATURE:
<221> NAME/KEY: source
<222> LOCATION: 1..17
<223> OTHER INFORMATION: /mol_type="unassigned RNA"
　　　/note="Reverse complementary sequence of minimal UTR2 including
　　　TISU element"
　　　/organism="Artificial Sequence"
<220> FEATURE:
<221> NAME/KEY: variation
<222> LOCATION: 10
<223> OTHER INFORMATION: /replace="G"
　　　/replace="C"
　　　/replace="A"
　　　/replace="U"

<400> SEQUENCE: 14
caucuuggcn gucuccc                                               17

<210> SEQ ID NO 15
<211> LENGTH: 16
<212> TYPE: RNA
<213> ORGANISM: Artificial Sequence
<220> FEATURE:
<221> NAME/KEY: source
<222> LOCATION: 1..16
<223> OTHER INFORMATION: /mol_type="unassigned RNA"
　　　/note="Reverse complementary sequence of the alternative minimal
　　　UTR1"
　　　/organism="Artificial Sequence"

<400> SEQUENCE: 15
cauggcggcg ucuccc                                                16

<210> SEQ ID NO 16
<211> LENGTH: 17
<212> TYPE: RNA
<213> ORGANISM: Artificial Sequence
<220> FEATURE:
<221> NAME/KEY: source
<222> LOCATION: 1..17
<223> OTHER INFORMATION: /mol_type="unassigned RNA"
　　　/note="Reverse complementary sequence of the alternative minimal
　　　UTR2"
　　　/organism="Artificial Sequence"
<220> FEATURE:
<221> NAME/KEY: variation

```
<222> LOCATION: 10
<223> OTHER INFORMATION: /replace="U"
      /replace="A"
      /replace="G"
      /replace="C"

<400> SEQUENCE: 16
cauggcggcn gucuccc                                                    17

<210> SEQ ID NO 17
<211> LENGTH: 16
<212> TYPE: RNA
<213> ORGANISM: Artificial Sequence
<220> FEATURE:
<221> NAME/KEY: source
<222> LOCATION: 1..16
<223> OTHER INFORMATION: /mol_type="unassigned RNA"
      /note="Reverse complementary sequence of the alternative minimal
      UTR1 including TISU element"
      /organism="Artificial Sequence"

<400> SEQUENCE: 17
caucucggcg ucuccc                                                     16

<210> SEQ ID NO 18
<211> LENGTH: 17
<212> TYPE: RNA
<213> ORGANISM: Artificial Sequence
<220> FEATURE:
<221> NAME/KEY: source
<222> LOCATION: 1..17
<223> OTHER INFORMATION: /mol_type="unassigned RNA"
      /note="Reverse complementary sequence of the alternative minimal
      UTR2 including TISU element"
      /organism="Artificial Sequence"
<220> FEATURE:
<221> NAME/KEY: variation
<222> LOCATION: 10
<223> OTHER INFORMATION: /replace="U"
      /replace="G"
      /replace="C"
      /replace="A"

<400> SEQUENCE: 18
caucucggcn gucuccc                                                    17

<210> SEQ ID NO 19
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
      /note="Reverse complementary sequence of minimal UTR1"
      /organism="Artificial Sequence"

<400> SEQUENCE: 19
caugguggcg uccc                                                       14

<210> SEQ ID NO 20
<211> LENGTH: 15
<212> TYPE: RNA
<213> ORGANISM: Artificial Sequence
<220> FEATURE:
<221> NAME/KEY: source
<222> LOCATION: 1..15
<223> OTHER INFORMATION: /mol_type="unassigned RNA"
      /note="Reverse complementary sequence of minimal UTR2"
      /organism="Artificial Sequence"
<220> FEATURE:
```

```
<221> NAME/KEY: variation
<222> LOCATION: 10
<223> OTHER INFORMATION: /replace="A"
      /replace="C"
      /replace="G"
      /replace="U"

<400> SEQUENCE: 20 cauggugggcn guccc                                                    15

<210> SEQ ID NO 21
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
      /note="Reverse complementary sequence of minimal UTR1 including
      TISU element"
      /organism="Artificial Sequence"

<400> SEQUENCE: 21
caucuuggcg uccc                                                      14

<210> SEQ ID NO 22
<211> LENGTH: 15
<212> TYPE: RNA
<213> ORGANISM: Artificial Sequence
<220> FEATURE:
<221> NAME/KEY: source
<222> LOCATION: 1..15
<223> OTHER INFORMATION: /mol_type="unassigned RNA"
      /note="Reverse complementary sequence of minimal UTR2 including
      TISU element"
      /organism="Artificial Sequence"
<220> FEATURE:
<221> NAME/KEY: variation
<222> LOCATION: 10
<223> OTHER INFORMATION: /replace="A"
      /replace="C"
      /replace="G"
      /replace="U"

<400> SEQUENCE: 22
caucuuggcn guccc                                                     15

<210> SEQ ID NO 23
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
      /note="Reverse complementary sequence of the alternative minimal
      UTR1"
      /organism="Artificial Sequence"

<400> SEQUENCE: 23
cauggcggcg uccc                                                      14

<210> SEQ ID NO 24
<211> LENGTH: 15
<212> TYPE: RNA
<213> ORGANISM: Artificial Sequence
<220> FEATURE:
<221> NAME/KEY: source
<222> LOCATION: 1..15
<223> OTHER INFORMATION: /mol_type="unassigned RNA"
      /note="Reverse complementary sequence of the alternative minimal
```

```
        UTR2"
        /organism="Artificial Sequence"
<220> FEATURE:
<221> NAME/KEY: variation
<222> LOCATION: 10
<223> OTHER INFORMATION: /replace="A"
        /replace="C"
        /replace="G"
        /replace="U"

<400> SEQUENCE: 24
cauggcggcn guccc                                                        15

<210> SEQ ID NO 25
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
        /note="Reverse complementary sequence of the alternative minimal
        UTR1 including TISU element"
        /organism="Artificial Sequence"

<400> SEQUENCE: 25
caucucggcg uccc                                                         14

<210> SEQ ID NO 26
<211> LENGTH: 15
<212> TYPE: RNA
<213> ORGANISM: Artificial Sequence
<220> FEATURE:
<221> NAME/KEY: source
<222> LOCATION: 1..15
<223> OTHER INFORMATION: /mol_type="unassigned RNA"
        /note="Reverse complementary sequence of the alternative minimal
        UTR2 including TISU element"
        /organism="Artificial Sequence"
<220> FEATURE:
<221> NAME/KEY: variation
<222> LOCATION: 10
<223> OTHER INFORMATION: /replace="A"
        /replace="C"
        /replace="G"
        /replace="U"

<400> SEQUENCE: 26
caucucggcn guccc                                                        15

<210> SEQ ID NO 27
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
        /note="Reverse complementary sequence of minimal UTR1"
        /organism="Artificial Sequence"

<400> SEQUENCE: 27
caugguggcg cuuc                                                         14

<210> SEQ ID NO 28
<211> LENGTH: 15
<212> TYPE: RNA
<213> ORGANISM: Artificial Sequence
<220> FEATURE:
<221> NAME/KEY: source
<222> LOCATION: 1..15
```

```
<223> OTHER INFORMATION: /mol_type="unassigned RNA"
      /note="Reverse complementary sequence of minimal UTR2"
      /organism="Artificial Sequence"
<220> FEATURE:
<221> NAME/KEY: variation
<222> LOCATION: 10
<223> OTHER INFORMATION: /replace="A"
      /replace="C"
      /replace="G"
      /replace="U"

<400> SEQUENCE: 28 cauggugcn gcuuc                                              15

<210> SEQ ID NO 29
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
      /note="Reverse complementary sequence of minimal UTR1 including
      TISU element"
      /organism="Artificial Sequence"

<400> SEQUENCE: 29
caucuuggcg cuuc                                              14

<210> SEQ ID NO 30
<211> LENGTH: 15
<212> TYPE: RNA
<213> ORGANISM: Artificial Sequence
<220> FEATURE:
<221> NAME/KEY: source
<222> LOCATION: 1..15
<223> OTHER INFORMATION: /mol_type="unassigned RNA"
      /note="Reverse complementary sequence of minimal UTR2 including
      TISU element"
      /organism="Artificial Sequence"
<220> FEATURE:
<221> NAME/KEY: variation
<222> LOCATION: 10
<223> OTHER INFORMATION: /replace="A"
      /replace="C"
      /replace="G"
      /replace="U"

<400> SEQUENCE: 30
caucuuggcn gcuuc                                             15

<210> SEQ ID NO 31
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
      /note="Reverse complementary sequence of the alternative minimal
      UTR1"
      /organism="Artificial Sequence"

<400> SEQUENCE: 31
cauggcggcg cuuc                                              14

<210> SEQ ID NO 32
<211> LENGTH: 15
<212> TYPE: RNA
<213> ORGANISM: Artificial Sequence
<220> FEATURE:
```

```
<221> NAME/KEY: source
<222> LOCATION: 1..15
<223> OTHER INFORMATION: /mol_type="unassigned RNA"
      /note="Reverse complementary sequence of the alternative minimal
      UTR2"
      /organism="Artificial Sequence"
<220> FEATURE:
<221> NAME/KEY: variation
<222> LOCATION: 10
<223> OTHER INFORMATION: /replace="A"
      /replace="C"
      /replace="G"
      /replace="U"

<400> SEQUENCE: 32
cauggcggcn gcuuc                                                   15

<210> SEQ ID NO 33
<211> LENGTH: 14
<212> TYPE: RNA
<213> ORGANISM: Artificial Sequence
<220> FEATURE:
<221> NAME/KEY: source
<222> LOCATION: 1..14
<223> OTHER INFORMATION: /mol_type="unassigned RNA"
      /note="Reverse complementary sequence of the alternative minimal
      UTR1 including TISU element"
      /organism="Artificial Sequence"

<400> SEQUENCE: 33
caucucggcg cuuc                                                    14

<210> SEQ ID NO 34
<211> LENGTH: 15
<212> TYPE: RNA
<213> ORGANISM: Artificial Sequence
<220> FEATURE:
<221> NAME/KEY: source
<222> LOCATION: 1..15
<223> OTHER INFORMATION: /mol_type="unassigned RNA"
      /note="Reverse complementary sequence of the alternative minimal
      UTR2 including TISU element"
      /organism="Artificial Sequence"
<220> FEATURE:
<221> NAME/KEY: variation
<222> LOCATION: 10
<223> OTHER INFORMATION: /replace="A"
      /replace="C"
      /replace="G"
      /replace="U"

<400> SEQUENCE: 34
caucucggcn gcuuc                                                   15

<210> SEQ ID NO 35
<211> LENGTH: 637
<212> TYPE: DNA
<213> ORGANISM: Artificial Sequence
<220> FEATURE:
<221> NAME/KEY: source
<222> LOCATION: 1..637
<223> OTHER INFORMATION: /mol_type="unassigned DNA"
      /note="T7-TISU-hEPO (codon optimized)"
      /organism="Artificial Sequence"

<400> SEQUENCE: 35
gtgactagat cttaatacga ctcactatag ggagactgcc aagatgggcg tgcacgaatg   60
tcctgcttgg ctgtggctgc tgctgagcct gctgtctctg cctctgggac tgcctgtgct  120
gggagcccct cctagactga tctgcgacag ccgggtgctg gaaagatacc tgctggaagc  180
```

| | |
|---|---|
| caaagaggcc gagaacatca ccaccggctg cgccgagcac tgcagcctga acgagaatat | 240 |
| caccgtgccc gacaccaaag tgaacttcta cgcctggaag cggatggaag tgggccagca | 300 |
| ggctgtggaa gtgtggcagg gactggccct gctgagcgaa gctgtgctga gaggacaggc | 360 |
| tctgctcgtg aacagcagcc agccttggga gcctctgcag ctgcacgtgg acaaggccgt | 420 |
| gtctggcctg agaagcctga ccacactgct gagagccctg ggggcccaga agaggccat | 480 |
| ctctccacct gatgccgcct ctgccgcccc tctgagaacc atcaccgccg acaccttcag | 540 |
| aaagctgttc cgggtgtaca gcaacttcct gcggggcaag ctgaagctgt acacaggcga | 600 |
| ggcctgccgg accggcgata gataattcga agtgact | 637 |

<210> SEQ ID NO 36
<211> LENGTH: 1120
<212> TYPE: DNA
<213> ORGANISM: Artificial Sequence
<220> FEATURE:
<221> NAME/KEY: source
<222> LOCATION: 1..1120
<223> OTHER INFORMATION: /mol_type="unassigned DNA"
    /note="T7-TISU-hOTC (codon optimized)"
    /organism="Artificial Sequence"

<400> SEQUENCE: 36

| | |
|---|---|
| gtgactgcta gctaatacga ctcactatag ggagactgcc aagatgctgt tcaacctgcg | 60 |
| gatcctgctg aacaacgccg ccttccggaa cggccacaac ttcatggtgc gcaacttcag | 120 |
| atgcggccag cccctgcaga acaaggtgca gctgaagggc agggacctgc tgaccctgaa | 180 |
| gaacttcacc ggcgaagaga tcaagtacat gctgtggctg agcgccgacc tgaagttccg | 240 |
| gatcaagcag aagggcgagt acctgccccct gctgcagggc aagtctctgg gcatgatctt | 300 |
| cgagaagcgg agcaccccga cccggctgtc taccgagaca ggatttgccc tgctgggcgg | 360 |
| ccacccttgc tttctgacca cccaggatat ccacctgggc gtgaacgaga gcctgaccga | 420 |
| cacagccaga gtgctgagca gcatggccga tgccgtgctg gccagagtgt acaagcagag | 480 |
| cgacctggac accctggcca agaggccag catccccatc atcaacggcc tgtccgacct | 540 |
| gtaccacccc atccagatcc tggccgacta cctgacccctg caggaacact acagctccct | 600 |
| gaagggcctg acactgagct ggatcggcga cggcaacaac atcctgcact ctatcatgat | 660 |
| gagcgccgcc aagttcggca tgcatctgca ggccgccacc cccaagggct atgagcctga | 720 |
| tgccagcgtg accaagctgg ccgagcagta cgccaaagag aacggcacca agctgctgct | 780 |
| gaccaacgac cctctggaag ccgcccacgg cggcaatgtg ctgatcaccg ataccctggat | 840 |
| cagcatgggc caggaagagg aaaagaagaa gcggctgcag gccttccagg ctaccaagt | 900 |
| gaccatgaag accgccaaag tggccgccag cgactggacc ttcctgcact gcctgcccag | 960 |
| aaagcccgaa gaggtggacg acgaggtgtt ctacagcccc cggtccctgg tgtttcccga | 1020 |
| ggccgagaac cggaagtgga ccatcatggc tgtgatggtg tctctgctga ccgactactc | 1080 |
| cccccagctg cagaagccca agttctgaag cgctgtgact | 1120 |

<210> SEQ ID NO 37
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
    /note="T7Luc2"
    /organism="Artificial Sequence"

```
<400> SEQUENCE: 37
tatagggaga cgccaccatg                                             20

<210> SEQ ID NO 38
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="T7Luc2 (?C)"
      /organism="Artificial Sequence"

<400> SEQUENCE: 38
tatagggaga gccaccatg                                              19

<210> SEQ ID NO 39
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="T7Luc2 (+8+A)"
      /organism="Artificial Sequence"

<400> SEQUENCE: 39
tatagggaga cagccaccat g                                           21

<210> SEQ ID NO 40
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="T7Luc2 (+8+T)"
      /organism="Artificial Sequence"

<400> SEQUENCE: 40
tatagggaga ctgccaccat g                                           21

<210> SEQ ID NO 41
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="T7Luc2 (+8+G)"
      /organism="Artificial Sequence"

<400> SEQUENCE: 41
tatagggaga cggccaccat g                                           21

<210> SEQ ID NO 42
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="T7Luc2 (+8+C)"
```

```
            /organism="Artificial Sequence"

<400> SEQUENCE: 42
tatagggaga ccgccaccat g                                              21

<210> SEQ ID NO 43
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="T7Luc2 (+8+Sp30)"
      /organism="Artificial Sequence"
<220> FEATURE:
<221> NAME/KEY: variation
<222> LOCATION: 12
<223> OTHER INFORMATION: /replace="sequence of a random sequence of 30
      nucleotides"

<400> SEQUENCE: 43
tatagggaga cngccaccat g                                              21

<210> SEQ ID NO 44
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="T7Luc2 (+8+hAg)"
      /organism="Artificial Sequence"

<400> SEQUENCE: 44
tatagggaga ctcttctggt ccccacagac tcagagagaa cgccaccatg              50

<210> SEQ ID NO 45
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="T7Luc2 (+8+T)+TISU"
      /organism="Artificial Sequence"

<400> SEQUENCE: 45
tatagggaga ctgccaagat g                                              21
```